(12) United States Patent
Carley et al.

(10) Patent No.: US 9,585,646 B2
(45) Date of Patent: Mar. 7, 2017

(54) CLOSURE DEVICE AND METHODS FOR MAKING AND USING THEM

(71) Applicant: Integrated Vascular Systems, Inc., Redwood City, CA (US)

(72) Inventors: Michael T. Carley, San Jose, CA (US); Javier Sagastegui, Castro Valley, CA (US); Richard S. Ginn, Gilroy, CA (US); William N. Aldrich, Napa, CA (US); W. Martin Belef, San Jose, CA (US); Steven N. Roe, San Mateo, CA (US); Ronald J. Jabba, Redwood City, CA (US)

(73) Assignee: Integrated Vascular Systems, Inc., Redwood City, CA (US)

( * ) Notice: Subject to any disclaimer, the term of this patent is extended or adjusted under 35 U.S.C. 154(b) by 0 days.

(21) Appl. No.: 14/246,973

(22) Filed: Apr. 7, 2014

(65) Prior Publication Data

US 2014/0222069 A1    Aug. 7, 2014

Related U.S. Application Data

(60) Continuation of application No. 11/396,141, filed on Mar. 31, 2006, now Pat. No. 8,690,910, which is a (Continued)

(51) Int. Cl.
*A61B 17/08* (2006.01)
*A61D 1/00* (2006.01)
(Continued)

(52) U.S. Cl.
CPC ........ *A61B 17/0057* (2013.01); *A61B 17/064* (2013.01); *A61B 17/068* (2013.01);
(Continued)

(58) Field of Classification Search
CPC .............. A61B 17/0057; A61B 17/064; A61B 17/0644; A61B 17/083; A61B 17/128;
(Continued)

(56) References Cited

U.S. PATENT DOCUMENTS 287,046 A    10/1883    Norton
438,400 A    10/1890    Brennen
(Continued)

FOREIGN PATENT DOCUMENTS

AU    2003297432    7/2004
CA    2 339 060    2/2000
(Continued)

OTHER PUBLICATIONS

U.S. Appl. No. 09/610,128, filed Jul. 5, 2000, Kerievsky.
(Continued)

*Primary Examiner* — Melanie Tyson
(74) *Attorney, Agent, or Firm* — Workman Nydegger; Randy Shen

(57) ABSTRACT

A method that includes locating an opening in tissue by advancing a member through the opening in tissue and following locating the opening, deploying a medical device to aid with sealing the opening. The medical device includes a plurality of strut members forming a plurality of generally diamond-shaped openings, the plurality of strut member being configured to form an annular shaped structure with the generally diamond-shaped openings extending generally longitudinally relative to a longitudinal axis of the medical device. The medical device further includes a plurality of tissue engaging portions associated with the plurality of struts, each tissue engaging portion being disposed between adjacently positioned generally diamond-shaped openings.

18 Claims, 21 Drawing Sheets

Related U.S. Application Data continuation-in-part of application No. 10/787,073, filed on Feb. 24, 2004, now Pat. No. 7,806,904, which is a continuation-in-part of application No. 10/435,104, filed on May 9, 2003, now Pat. No. 7,879,071, which is a division of application No. 10/081,726, filed on Feb. 21, 2002, now Pat. No. 6,623,510, which is a continuation-in-part of application No. 09/732,178, filed on Dec. 7, 2000, now Pat. No. 6,719,777, said application No. 11/396,141 is a continuation-in-part of application No. 10/335,075, filed on Dec. 31, 2002, now Pat. No. 7,211,101, which is a continuation-in-part of application No. 10/081,726, which is a continuation-in-part of application No. 09/732,178.

(51) Int. Cl.
  *A61B 17/00* (2006.01)
  *A61B 17/064* (2006.01)
  *A61B 17/068* (2006.01)

(52) U.S. Cl.
  CPC .......... *A61B 17/0644* (2013.01); *A61B 90/39* (2016.02); *A61B 2017/00004* (2013.01); *A61B 2017/0061* (2013.01); *A61B 2017/00579* (2013.01); *A61B 2017/00592* (2013.01); *A61B 2017/00659* (2013.01); *A61B 2017/00668* (2013.01); *A61B 2017/00867* (2013.01); *A61B 2017/0641* (2013.01)

(58) Field of Classification Search
  CPC ... A61B 17/10; A61B 17/115; A61B 17/1152; A61B 2017/00579; A61B 2017/00584; A61B 2017/00592; A61B 2017/0061; A61B 2017/00668; A61B 2017/0645; A61B 2017/00659; A61B 2017/00867; A61B 2017/00641; A61B 2017/081; A61B 2017/083; A61B 2017/1157
  See application file for complete search history.

(56) References Cited

U.S. PATENT DOCUMENTS

| | | |
|---|---|---|
| 1,088,393 A | 2/1914 | Backus |
| 1,123,290 A | 1/1915 | Von Herff |
| 1,331,401 A | 2/1920 | Summers |
| 1,596,004 A | 8/1926 | De Bengoa |
| 1,647,958 A | 11/1927 | Ciarlante |
| 1,880,569 A | 10/1932 | Weis |
| 2,087,074 A | 7/1937 | Tucker |
| 2,210,061 A | 8/1940 | Caminez |
| 2,254,620 A | 9/1941 | Miller |
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,684,070 A | 7/1954 | Kelsey |
| 2,755,699 A | 7/1956 | Forster |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,482,428 A | 12/1969 | Kapitanov et al. |
| 3,494,533 A | 2/1970 | Green et al. |
| 3,510,923 A | 5/1970 | Blake |
| 3,523,351 A | 8/1970 | Filia |
| 3,586,002 A | 6/1971 | Wood |
| 3,604,425 A | 9/1971 | Le Roy |
| 3,618,447 A | 11/1971 | Goins |
| 3,677,243 A | 7/1972 | Nerz |
| 3,757,629 A | 9/1973 | Schneider |
| 3,805,337 A | 4/1974 | Branstetter |
| 3,823,719 A | 7/1974 | Cummings |
| 3,828,791 A | 8/1974 | Santos |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,939,820 A | 2/1976 | Grayzel |
| 3,944,114 A | 3/1976 | Coppens |
| 3,960,147 A | 6/1976 | Murray |
| 3,985,138 A | 10/1976 | Jarvik |
| 4,007,743 A | 2/1977 | Blake |
| 4,014,492 A | 3/1977 | Rothfuss |
| 4,018,228 A | 4/1977 | Goosen |
| 4,047,533 A | 9/1977 | Perciaccante et al. |
| 4,064,881 A | 12/1977 | Meredith |
| 4,112,944 A | 9/1978 | Williams |
| 4,153,321 A | 5/1979 | Pombrol |
| 4,162,673 A | 7/1979 | Patel |
| 4,169,476 A | 10/1979 | Hiltebrandt |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,273,129 A | 6/1981 | Boebel |
| 4,274,415 A | 6/1981 | Kanamoto et al. |
| 4,278,091 A | 7/1981 | Borzone |
| 4,317,445 A | 3/1982 | Robinson |
| 4,317,451 A | 3/1982 | Cerwin et al. |
| 4,318,401 A | 3/1982 | Zimmerman |
| 4,327,485 A | 5/1982 | Rix |
| 4,345,606 A | 8/1982 | Littleford |
| 4,359,052 A | 11/1982 | Staub |
| 4,368,736 A | 1/1983 | Kaster |
| 4,396,139 A | 8/1983 | Hall et al. |
| 4,407,286 A | 10/1983 | Noiles et al. |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,449,531 A | 5/1984 | Cerwin et al. |
| 4,475,544 A | 10/1984 | Reis |
| 4,480,356 A | 11/1984 | Martin |
| 4,485,816 A | 12/1984 | Krumme |
| RE31,855 E | 3/1985 | Osborne |
| 4,505,273 A | 3/1985 | Braun et al. |
| 4,505,274 A | 3/1985 | Speelman |
| 4,523,591 A | 6/1985 | Kaplan et al. |
| 4,523,695 A | 6/1985 | Braun et al. |
| 4,525,157 A | 6/1985 | Vaillancourt |
| 4,526,174 A | 7/1985 | Froehlich |
| 4,570,633 A | 2/1986 | Golden |
| 556,082 A | 3/1986 | Boeddinghaus |
| 4,586,503 A | 5/1986 | Kirsch et al. |
| 4,592,498 A | 6/1986 | Braun et al. |
| 4,596,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,635,637 A | 1/1987 | Schreiber |
| 4,644,956 A | 2/1987 | Morgenstern |
| 4,651,737 A | 3/1987 | Deniega |
| 4,664,305 A | 5/1987 | Blake, III et al. |
| 4,665,906 A | 5/1987 | Jervis |
| 4,687,469 A | 8/1987 | Osypka |
| 4,693,249 A | 9/1987 | Schenck et al. |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |

(56) References Cited

U.S. PATENT DOCUMENTS

| | | |
|---|---|---|
| 4,759,364 A | 7/1988 | Boebel |
| 4,771,782 A | 9/1988 | Millar |
| 4,772,266 A | 9/1988 | Groshong |
| 4,777,950 A | 10/1988 | Kees, Jr. |
| 4,789,090 A | 12/1988 | Blake, III |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,874,122 A | 10/1989 | Froelich et al. |
| 4,878,915 A | 11/1989 | Brantigan |
| 4,885,003 A | 12/1989 | Hillstead |
| 4,886,067 A | 12/1989 | Palermo |
| 4,887,601 A | 12/1989 | Richards |
| 4,890,612 A | 1/1990 | Kensey |
| 4,900,303 A | 2/1990 | Lemelson |
| 4,902,508 A | 2/1990 | Badylak et al. |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,967,949 A | 11/1990 | Sandhaus |
| 4,976,721 A | 12/1990 | Blasnik et al. |
| 4,983,176 A | 1/1991 | Cushman et al. |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,011,487 A | 4/1991 | Shichman |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |
| 5,032,127 A | 7/1991 | Frazee et al. |
| 5,035,692 A | 7/1991 | Lyon et al. |
| 5,041,129 A | 8/1991 | Hayhurst et al. |
| 5,042,707 A | 8/1991 | Taheri |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,061,283 A | 10/1991 | Silvestrini |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,141,520 A | 8/1992 | Goble et al. |
| 5,147,381 A | 9/1992 | Heimerl et al. |
| 5,156,609 A | 10/1992 | Nakao et al. |
| 5,163,343 A | 11/1992 | Gish |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,171,259 A | 12/1992 | Inoue |
| 5,176,648 A | 1/1993 | Holmes et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,193,533 A | 3/1993 | Body et al. |
| 5,197,971 A | 3/1993 | Bonutti |
| 5,207,697 A | 5/1993 | Carusillo et al. |
| 5,209,756 A | 5/1993 | Seedhom et al. |
| 5,217,024 A | 6/1993 | Dorsey et al. |
| 5,222,974 A | 6/1993 | Kensey et al. |
| 5,226,908 A | 7/1993 | Yoon |
| 5,236,435 A | 8/1993 | Sewell, Jr. |
| 5,242,456 A | 9/1993 | Nash et al. |
| 5,242,457 A | 9/1993 | Akopov et al. |
| 5,242,459 A | 9/1993 | Buelna |
| 5,243,857 A | 9/1993 | Velez |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,255,679 A | 10/1993 | Imran |
| 5,269,792 A | 12/1993 | Kovac et al. |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |
| 5,284,488 A | 2/1994 | Sideris |
| 5,289,963 A | 3/1994 | McGarry et al. |
| 5,290,243 A | 3/1994 | Chodorow et al. |
| 5,290,310 A | 3/1994 | Makower et al. |
| 5,292,309 A | 3/1994 | Van Tassel et al. |
| 5,292,332 A | 3/1994 | Lee |
| 5,304,183 A | 4/1994 | Gourlay et al. |
| 5,304,184 A | 4/1994 | Hathaway et al. |
| 5,304,204 A | 4/1994 | Bregen |
| 5,306,254 A | 4/1994 | Nash et al. |
| 5,309,927 A | 5/1994 | Welch |
| 5,318,542 A | 6/1994 | Hirsch et al. |
| 5,320,639 A | 6/1994 | Rudnick |
| 5,322,694 A | 6/1994 | Sixsmith |
| 5,327,908 A | 7/1994 | Gerry |
| 5,330,445 A | 7/1994 | Haaga |
| 5,330,503 A | 7/1994 | Yoon |
| 5,334,216 A | 8/1994 | Vidal et al. |
| 5,334,217 A | 8/1994 | Das |
| 5,335,680 A | 8/1994 | Moore |
| 5,340,360 A | 8/1994 | Stefanchik |
| 5,342,393 A | 8/1994 | Stack |
| 5,344,439 A | 9/1994 | Otten |
| 5,350,399 A | 9/1994 | Erlebacher et al. |
| 5,352,229 A | 10/1994 | Goble et al. |
| 5,354,279 A | 10/1994 | Hofling |
| 5,364,406 A | 11/1994 | Sewell, Jr. |
| 5,364,408 A | 11/1994 | Gordon |
| 5,366,458 A | 11/1994 | Korthoff et al. |
| 5,366,479 A | 11/1994 | McGarry et al. |
| 5,383,896 A | 1/1995 | Gershony et al. |
| 5,383,897 A | 1/1995 | Wholey |
| RE34,866 E | 2/1995 | Kensey et al. |
| 5,392,978 A | 2/1995 | Velez et al. |
| 5,395,030 A | 3/1995 | Kuramoto et al. |
| 5,411,520 A | 5/1995 | Nash et al. |
| 5,413,571 A | 5/1995 | Katsaros et al. |
| 5,413,584 A | 5/1995 | Schulze |
| 5,416,584 A | 5/1995 | Kay |
| 5,417,699 A | 5/1995 | Klein et al. |
| 5,419,765 A | 5/1995 | Weldon et al. |
| 5,419,777 A | 5/1995 | Hofling |
| 5,421,832 A | 6/1995 | Lefebvre |
| 5,423,857 A | 6/1995 | Rosenman et al. |
| 5,425,489 A | 6/1995 | Shichman et al. |
| 5,425,740 A | 6/1995 | Hutchinson, Jr. |
| 5,431,639 A | 7/1995 | Shaw |
| 5,431,667 A | 7/1995 | Thompson et al. |
| 5,433,721 A | 7/1995 | Hooven et al. |
| 5,437,631 A | 8/1995 | Janzen |
| 5,439,479 A | 8/1995 | Shichman et al. |
| 5,443,477 A | 8/1995 | Marin et al. |
| 5,443,481 A | 8/1995 | Lee |
| 5,445,167 A | 8/1995 | Yoon et al. |
| 5,449,359 A | 9/1995 | Groiso |
| 5,451,235 A | 9/1995 | Lock et al. |
| 5,456,400 A | 10/1995 | Shichman et al. |
| 5,462,561 A | 10/1995 | Voda |
| 5,464,413 A | 11/1995 | Siska, Jr. et al. |

(56) References Cited

U.S. PATENT DOCUMENTS

| | | |
|---|---|---|
| 5,464,416 A | 11/1995 | Steckel |
| 5,466,241 A | 11/1995 | Leroy et al. |
| 5,470,010 A | 11/1995 | Rothfuss et al. |
| 5,471,982 A | 12/1995 | Edwards et al. |
| 5,474,557 A | 12/1995 | Mai |
| 5,474,569 A | 12/1995 | Zinreich et al. |
| 5,476,505 A | 12/1995 | Limon |
| 5,478,352 A | 12/1995 | Fowler |
| 5,478,353 A | 12/1995 | Yoon |
| 5,478,354 A | 12/1995 | Tovey et al. |
| 5,484,420 A | 1/1996 | Russo |
| 5,486,195 A | 1/1996 | Myers et al. |
| 5,496,332 A | 3/1996 | Sierra et al. |
| 5,497,933 A | 3/1996 | DeFonzo et al. |
| 5,507,744 A | 4/1996 | Tay et al. |
| 5,507,755 A | 4/1996 | Gresl et al. |
| 5,510,115 A | 4/1996 | Breillatt, Jr. et al. |
| 5,522,840 A | 6/1996 | Krajicek |
| 5,527,322 A | 6/1996 | Klein et al. |
| 5,536,251 A | 7/1996 | Evard et al. |
| 5,540,712 A | 7/1996 | Kleshinski et al. |
| 5,540,716 A | 7/1996 | Hlavacek |
| 5,544,802 A | 8/1996 | Crainich |
| 5,545,178 A | 8/1996 | Kensey et al. |
| 5,547,474 A | 8/1996 | Kloeckl et al. |
| 5,560,532 A | 10/1996 | DeFonzo et al. |
| 5,571,120 A | 11/1996 | Yoon |
| 5,573,784 A | 11/1996 | Badylak et al. |
| 5,575,771 A | 11/1996 | Walinsky |
| 5,582,616 A | 12/1996 | Bolduc et al. |
| 5,584,879 A | 12/1996 | Reimold et al. |
| 5,591,205 A | 1/1997 | Fowler |
| 5,593,412 A | 1/1997 | Martinez et al. |
| 5,601,602 A | 2/1997 | Fowler |
| 5,609,597 A | 3/1997 | Lehrer |
| 5,613,974 A | 3/1997 | Andreas et al. |
| 5,618,291 A | 4/1997 | Thompson et al. |
| 5,620,452 A | 4/1997 | Yoon |
| 5,620,461 A | 4/1997 | Muijs et al. |
| 5,626,614 A | 5/1997 | Hart |
| 5,634,936 A | 6/1997 | Linden et al. |
| 5,643,318 A | 7/1997 | Tsukernik et al. |
| 5,645,565 A | 7/1997 | Rudd et al. |
| 5,645,566 A | 7/1997 | Brenneman et al. |
| 5,645,567 A | 7/1997 | Crainich |
| 5,649,959 A | 7/1997 | Hannam et al. |
| D383,539 S | 9/1997 | Croley |
| 5,674,231 A | 10/1997 | Green et al. |
| 5,676,689 A | 10/1997 | Kensey et al. |
| 5,676,974 A | 10/1997 | Valdes et al. |
| 5,681,280 A | 10/1997 | Rusk et al. |
| 5,681,334 A | 10/1997 | Evans et al. |
| 5,683,405 A | 11/1997 | Yacoubian et al. |
| 5,690,674 A | 11/1997 | Diaz |
| 5,695,504 A | 12/1997 | Gifford, III et al. |
| 5,695,505 A | 12/1997 | Yoon |
| 5,695,524 A | 12/1997 | Kelley et al. |
| 5,697,943 A | 12/1997 | Sauer et al. |
| 5,700,273 A | 12/1997 | Buelna et al. |
| 5,709,224 A | 1/1998 | Behl et al. |
| 5,715,987 A | 2/1998 | Kelley et al. |
| 5,716,375 A | 2/1998 | Fowler |
| 5,720,755 A | 2/1998 | Dakov |
| 5,725,498 A | 3/1998 | Janzen et al. |
| 5,725,552 A | 3/1998 | Kotula et al. |
| 5,725,554 A | 3/1998 | Simon et al. |
| 5,728,110 A | 3/1998 | Vidal et al. |
| 5,728,114 A | 3/1998 | Evans et al. |
| 5,728,116 A | 3/1998 | Rosenman |
| 5,728,122 A | 3/1998 | Leschinsky et al. |
| 5,728,132 A | 3/1998 | Van Tassel et al. |
| 5,728,133 A | 3/1998 | Kontos |
| 5,732,872 A | 3/1998 | Bolduc et al. |
| 5,735,873 A | 4/1998 | MacLean |
| 5,749,826 A | 5/1998 | Faulkner |
| 5,752,966 A | 5/1998 | Chang |
| 5,755,726 A | 5/1998 | Pratt et al. |
| 5,755,727 A | 5/1998 | Kontos |
| 5,755,778 A | 5/1998 | Kleshinski |
| 5,766,217 A | 6/1998 | Christy |
| 5,766,246 A | 6/1998 | Mulhauser et al. |
| 5,769,870 A | 6/1998 | Salahieh et al. |
| 5,776,147 A | 7/1998 | Dolendo |
| 5,779,707 A | 7/1998 | Bertholet et al. |
| 5,780,807 A | 7/1998 | Saunders |
| 5,782,844 A | 7/1998 | Yoon et al. |
| 5,782,860 A | 7/1998 | Epstein et al. |
| 5,782,861 A | 7/1998 | Cragg et al. |
| 5,795,958 A | 8/1998 | Rao et al. |
| 5,797,928 A | 8/1998 | Kogasaka |
| 5,797,931 A | 8/1998 | Bito et al. |
| 5,797,933 A | 8/1998 | Snow et al. |
| 5,797,958 A | 8/1998 | Yoon |
| 5,797,960 A | 8/1998 | Stevens et al. |
| 5,810,776 A | 9/1998 | Bacich et al. |
| 5,810,846 A | 9/1998 | Virnich et al. |
| 5,810,851 A | 9/1998 | Yoon |
| 5,817,113 A | 10/1998 | Gifford, III et al. |
| 5,820,631 A | 10/1998 | Nobles |
| 5,827,298 A | 10/1998 | Hart et al. |
| 5,830,125 A | 11/1998 | Scribner et al. |
| 5,830,217 A | 11/1998 | Ryan |
| 5,830,221 A | 11/1998 | Stein et al. |
| 5,833,698 A | 11/1998 | Hinchliffe et al. |
| 5,843,164 A | 12/1998 | Frantzen et al. |
| 5,843,167 A | 12/1998 | Dwyer et al. |
| 5,853,421 A | 12/1998 | Leschinsky et al. |
| 5,853,422 A | 12/1998 | Huebsch et al. |
| 5,855,312 A | 1/1999 | Toledano |
| 5,858,082 A | 1/1999 | Cruz et al. |
| 5,860,991 A | 1/1999 | Klein et al. |
| 5,861,003 A | 1/1999 | Latson et al. |
| 5,861,005 A | 1/1999 | Kontos |
| 5,861,043 A | 1/1999 | Carn |
| 5,865,791 A | 2/1999 | Whayne et al. |
| 5,868,755 A | 2/1999 | Kanner et al. |
| 5,868,762 A | 2/1999 | Cragg et al. |
| 5,868,763 A | 2/1999 | Spence et al. |
| 5,871,474 A | 2/1999 | Hermann et al. |
| 5,871,501 A | 2/1999 | Leschinsky et al. |
| 5,871,525 A | 2/1999 | Edwards et al. |
| 5,873,876 A | 2/1999 | Christy |
| 5,873,891 A | 2/1999 | Sohn |
| 5,879,366 A | 3/1999 | Shaw et al. |
| 5,891,088 A | 4/1999 | Thompson et al. |
| 5,897,487 A | 4/1999 | Ouchi |
| 5,902,310 A | 5/1999 | Foerster et al. |
| 5,904,696 A | 5/1999 | Rosenman |
| 5,904,697 A | 5/1999 | Gifford, III et al. |
| 5,904,703 A | 5/1999 | Gilson |
| 5,906,631 A | 5/1999 | Imran |
| 5,907,893 A | 6/1999 | Zadno-Azizi et al. |
| 5,908,149 A | 6/1999 | Welch et al. |
| 5,910,155 A | 6/1999 | Ratcliff et al. |
| 5,919,207 A | 7/1999 | Taheri |
| 5,922,009 A | 7/1999 | Epstein et al. |
| 5,928,231 A | 7/1999 | Klein et al. |
| 5,928,251 A | 7/1999 | Aranyi et al. |
| 5,928,260 A | 7/1999 | Chin et al. |
| 5,935,147 A | 8/1999 | Kensey et al. |
| 5,938,667 A | 8/1999 | Peyser et al. |
| 5,941,890 A | 8/1999 | Voegele et al. |
| 5,947,999 A | 9/1999 | Groiso |
| 5,948,001 A | 9/1999 | Larsen |
| 5,951,518 A | 9/1999 | Licata et al. |
| 5,951,575 A | 9/1999 | Bolduc et al. |
| 5,951,576 A | 9/1999 | Wakabayashi |
| 5,951,589 A | 9/1999 | Epstein et al. |
| 5,954,732 A | 9/1999 | Hart et al. |
| 5,957,900 A | 9/1999 | Ouchi |
| 5,957,936 A | 9/1999 | Yoon et al. |
| 5,957,938 A | 9/1999 | Zhu et al. |
| 5,957,940 A | 9/1999 | Tanner et al. |
| 5,964,782 A | 10/1999 | Lafontaine et al. |

(56) References Cited

U.S. PATENT DOCUMENTS

| | | | |
|---|---|---|---|
| 5,972,023 A | 10/1999 | Tanner et al. |
| 5,972,034 A | 10/1999 | Hofmann et al. |
| 5,976,161 A | 11/1999 | Kirsch et al. |
| 5,976,174 A | 11/1999 | Ruiz |
| 5,984,934 A | 11/1999 | Ashby et al. |
| 5,984,948 A | 11/1999 | Hasson |
| 5,984,949 A | 11/1999 | Levin |
| 5,993,468 A | 11/1999 | Rygaard |
| 5,993,476 A | 11/1999 | Groiso |
| 6,001,110 A | 12/1999 | Adams |
| 6,004,341 A | 12/1999 | Zhu et al. |
| 6,007,563 A | 12/1999 | Nash et al. |
| 6,007,574 A | 12/1999 | Pulnev et al. |
| 6,010,517 A | 1/2000 | Baccaro |
| 6,013,084 A | 1/2000 | Ken et al. |
| 6,015,815 A | 1/2000 | Mollison |
| 6,019,779 A | 2/2000 | Thorud et al. |
| 6,022,372 A | 2/2000 | Kontos |
| 6,024,750 A | 2/2000 | Mastri |
| 6,024,756 A | 2/2000 | Huebsch et al. |
| 6,030,364 A | 2/2000 | Durgin et al. |
| 6,030,413 A | 2/2000 | Lazarus |
| 6,033,427 A | 3/2000 | Lee |
| 6,036,703 A | 3/2000 | Evans et al. |
| 6,036,720 A | 3/2000 | Abrams et al. |
| 6,045,570 A | 4/2000 | Epstein et al. |
| 6,048,358 A | 4/2000 | Barak |
| 6,056,768 A | 5/2000 | Cates et al. |
| 6,056,769 A | 5/2000 | Epstein et al. |
| 6,056,770 A | 5/2000 | Epstein et al. |
| 6,059,800 A | 5/2000 | Hart et al. |
| 6,059,825 A | 5/2000 | Hobbs et al. |
| 6,063,085 A | 5/2000 | Tay et al. |
| 6,063,114 A | 5/2000 | Nash et al. |
| 6,071,300 A | 6/2000 | Brenneman et al. |
| 6,074,395 A | 6/2000 | Trott et al. |
| 6,077,281 A | 6/2000 | Das |
| 6,077,291 A | 6/2000 | Das |
| 6,080,182 A | 6/2000 | Shaw et al. |
| 6,080,183 A | 6/2000 | Tsugita et al. |
| 6,090,130 A | 7/2000 | Nash et al. |
| 6,102,271 A | 8/2000 | Longo et al. |
| 6,110,184 A | 8/2000 | Weadock |
| 6,113,610 A | 9/2000 | Poncet |
| 6,113,611 A | 9/2000 | Allen et al. |
| 6,113,612 A * | 9/2000 | Swanson ............... A61F 2/88 623/1.15 |
| 6,117,125 A | 9/2000 | Rothbarth et al. |
| 6,117,144 A | 9/2000 | Nobles et al. |
| 6,117,148 A | 9/2000 | Ravo |
| 6,117,157 A | 9/2000 | Tekulve |
| 6,117,159 A | 9/2000 | Huebsch et al. |
| 6,120,524 A | 9/2000 | Taheri |
| 6,126,675 A | 10/2000 | Shchervinsky et al. |
| 6,136,010 A | 10/2000 | Modesitt et al. |
| 6,146,385 A | 11/2000 | Torrie et al. |
| 6,149,660 A | 11/2000 | Laufer et al. |
| 6,149,667 A | 11/2000 | Hovland et al. |
| 6,152,144 A | 11/2000 | Lesh et al. |
| 6,152,936 A | 11/2000 | Christy et al. |
| 6,152,937 A | 11/2000 | Peterson et al. |
| 6,165,204 A | 12/2000 | Levinson et al. |
| 6,171,277 B1 | 1/2001 | Ponzi |
| 6,171,329 B1 | 1/2001 | Shaw et al. |
| 6,174,322 B1 | 1/2001 | Schneidt |
| 6,179,849 B1 | 1/2001 | Yencho et al. |
| 6,179,860 B1 | 1/2001 | Fulton, III et al. |
| 6,183,775 B1 | 2/2001 | Ventouras |
| 6,193,708 B1 | 2/2001 | Ken et al. |
| 6,193,734 B1 | 2/2001 | Bolduc et al. |
| 6,197,042 B1 | 3/2001 | Ginn et al. |
| 6,198,974 B1 | 3/2001 | Webster, Jr. |
| 6,200,329 B1 | 3/2001 | Fung et al. |
| 6,200,330 B1 | 3/2001 | Benderev et al. |
| 6,206,895 B1 | 3/2001 | Levinson |
| 6,206,913 B1 | 3/2001 | Yencho et al. |
| 6,206,931 B1 | 3/2001 | Cook et al. |
| 6,210,407 B1 | 4/2001 | Webster |
| 6,210,418 B1 | 4/2001 | Storz et al. |
| 6,217,554 B1 | 4/2001 | Green |
| 6,220,248 B1 | 4/2001 | Voegele et al. |
| 6,221,102 B1 | 4/2001 | Baker et al. |
| 6,231,561 B1 | 5/2001 | Frazier et al. |
| 6,238,705 B1 | 5/2001 | Liu et al. |
| 6,241,740 B1 | 6/2001 | Davis et al. |
| 6,245,079 B1 | 6/2001 | Nobles et al. |
| 6,248,124 B1 | 6/2001 | Pedros et al. |
| 6,254,617 B1 | 7/2001 | Spence et al. |
| 6,254,642 B1 | 7/2001 | Taylor |
| 6,258,115 B1 | 7/2001 | Dubrul |
| 6,261,309 B1 | 7/2001 | Urbanski |
| 6,267,773 B1 | 7/2001 | Gadberry et al. |
| 6,273,903 B1 | 8/2001 | Wilk |
| 6,277,140 B2 | 8/2001 | Ginn et al. |
| 6,280,460 B1 | 8/2001 | Bolduc et al. |
| 6,287,322 B1 | 9/2001 | Zhu et al. |
| 6,287,335 B1 | 9/2001 | Drasler et al. |
| 6,290,674 B1 | 9/2001 | Roue et al. |
| 6,296,657 B1 | 10/2001 | Brucker |
| 6,302,870 B1 | 10/2001 | Jacobsen et al. |
| 6,302,898 B1 | 10/2001 | Edwards et al. |
| 6,305,891 B1 | 10/2001 | Burlingame |
| 6,309,416 B1 | 10/2001 | Swanson et al. |
| 6,319,258 B1 | 11/2001 | McAllen, III et al. |
| 6,322,580 B1 | 11/2001 | Kanner |
| 6,328,727 B1 | 12/2001 | Frazier et al. |
| 6,329,386 B1 | 12/2001 | Mollison |
| 6,334,865 B1 | 1/2002 | Redmond et al. |
| 6,348,064 B1 | 2/2002 | Kanner |
| 6,355,052 B1 | 3/2002 | Neuss et al. |
| 6,355,061 B1 * | 3/2002 | Quiachon ............... A61F 2/07 604/96.01 |
| 6,358,258 B1 | 3/2002 | Arcia et al. |
| 6,375,671 B1 | 4/2002 | Kobayashi et al. |
| D457,958 S | 5/2002 | Dycus |
| 6,383,208 B1 | 5/2002 | Sancoff et al. |
| 6,391,048 B1 | 5/2002 | Ginn et al. |
| 6,395,015 B1 | 5/2002 | Borst et al. |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,421,899 B1 | 7/2002 | Zitnay |
| 6,423,054 B1 | 7/2002 | Ouchi |
| 6,425,911 B1 | 7/2002 | Akerfeldt et al. |
| 6,428,472 B1 | 8/2002 | Haas |
| 6,428,548 B1 | 8/2002 | Durgin et al. |
| 6,443,158 B1 | 9/2002 | Lafontaine et al. |
| 6,443,963 B1 | 9/2002 | Baldwin et al. |
| 6,447,540 B1 | 9/2002 | Fontaine et al. |
| 6,450,391 B1 | 9/2002 | Kayan et al. |
| 6,455,053 B1 | 9/2002 | Okada et al. |
| 6,458,130 B1 | 10/2002 | Frazier et al. |
| 6,461,364 B1 | 10/2002 | Ginn et al. |
| 6,482,224 B1 | 11/2002 | Michler et al. |
| 6,488,692 B1 | 12/2002 | Spence et al. |
| 6,494,848 B1 | 12/2002 | Sommercorn et al. |
| 6,500,115 B2 | 12/2002 | Krattiger et al. |
| 6,506,210 B1 | 1/2003 | Kanner |
| 6,508,828 B1 | 1/2003 | Akerfeldt et al. |
| 6,514,280 B1 | 2/2003 | Gilson |
| 6,517,555 B1 | 2/2003 | Caro |
| 6,517,569 B2 | 2/2003 | Mikus et al. |
| 6,527,737 B2 | 3/2003 | Kaneshige |
| 6,533,762 B2 | 3/2003 | Kanner et al. |
| 6,533,812 B2 | 3/2003 | Swanson et al. |
| 6,537,288 B2 | 3/2003 | Vargas et al. |
| 6,544,230 B1 | 4/2003 | Flaherty et al. |
| 6,547,806 B1 | 4/2003 | Ding |
| 6,551,303 B1 | 4/2003 | Van Tassel et al. |
| 6,551,319 B2 | 4/2003 | Lieberman |
| 6,558,349 B1 | 5/2003 | Kirkman |
| 6,569,173 B1 | 5/2003 | Blatter et al. |
| 6,569,185 B2 | 5/2003 | Ungs |

(56) References Cited

U.S. PATENT DOCUMENTS

| | | |
|---|---|---|
| 6,572,629 B2 | 6/2003 | Kalloo et al. |
| 6,582,452 B2 | 6/2003 | Coleman et al. |
| 6,582,482 B2 | 6/2003 | Gillman et al. |
| 6,596,012 B2 | 7/2003 | Akerfeldt et al. |
| 6,596,013 B2 | 7/2003 | Yang et al. |
| 6,599,303 B1 | 7/2003 | Peterson et al. |
| 6,599,311 B1 | 7/2003 | Biggs et al. |
| 6,602,263 B1 | 8/2003 | Swanson et al. |
| 6,610,072 B1 | 8/2003 | Christy et al. |
| 6,613,059 B2 | 9/2003 | Schaller et al. |
| 6,616,686 B2 | 9/2003 | Coleman et al. |
| 6,620,165 B2 | 9/2003 | Wellisz |
| 6,623,509 B2 | 9/2003 | Ginn |
| 6,623,510 B2 | 9/2003 | Carley et al. |
| 6,626,918 B1 | 9/2003 | Ginn et al. |
| 6,626,919 B1 | 9/2003 | Swanstrom |
| 6,626,920 B2 | 9/2003 | Whayne |
| 6,626,930 B1 | 9/2003 | Allen et al. |
| 6,632,197 B2 | 10/2003 | Lyon |
| 6,632,238 B2 | 10/2003 | Ginn et al. |
| 6,634,537 B2 | 10/2003 | Chen |
| 6,645,205 B2 | 11/2003 | Ginn |
| 6,645,225 B1 | 11/2003 | Atkinson |
| 6,652,538 B2 | 11/2003 | Kayan et al. |
| 6,652,555 B1 | 11/2003 | VanTassel et al. |
| 6,652,556 B1 | 11/2003 | VanTassel et al. |
| 6,663,633 B1 | 12/2003 | Pierson, III |
| 6,663,655 B2 | 12/2003 | Ginn et al. |
| 6,669,714 B2 | 12/2003 | Coleman et al. |
| 6,673,083 B1 | 1/2004 | Kayan et al. |
| 6,676,665 B2 | 1/2004 | Foley et al. |
| 6,676,671 B2 | 1/2004 | Robertson et al. |
| 6,676,685 B2 | 1/2004 | Pedros et al. |
| 6,679,904 B2 | 1/2004 | Gleeson et al. |
| 6,685,707 B2 | 2/2004 | Roman et al. |
| 6,689,147 B1 | 2/2004 | Koster, Jr. |
| 6,689,150 B1 | 2/2004 | VanTassel et al. |
| 6,695,867 B2 | 2/2004 | Ginn et al. |
| 6,699,256 B1 | 3/2004 | Logan et al. |
| 6,702,825 B2 | 3/2004 | Frazier et al. |
| 6,702,826 B2 | 3/2004 | Liddicoat et al. |
| 6,712,836 B1 | 3/2004 | Berg et al. |
| 6,712,837 B2 | 3/2004 | Akerfeldt et al. |
| 6,719,777 B2 | 4/2004 | Ginn et al. |
| 6,726,704 B1 | 4/2004 | Loshakove et al. |
| 6,730,108 B2 | 5/2004 | Van Tassel et al. |
| 6,743,195 B2 | 6/2004 | Zucker |
| 6,743,243 B1 | 6/2004 | Roy et al. |
| 6,743,259 B2 | 6/2004 | Ginn |
| 6,746,472 B2 | 6/2004 | Frazier et al. |
| 6,749,621 B2 | 6/2004 | Pantages et al. |
| 6,749,622 B2 | 6/2004 | McGuckin et al. |
| 6,752,813 B2 | 6/2004 | Goldfarb et al. |
| 6,755,842 B2 | 6/2004 | Kanner et al. |
| 6,758,855 B2 | 7/2004 | Fulton, III et al. |
| 6,767,356 B2 | 7/2004 | Kanner et al. |
| 6,776,784 B2 * | 8/2004 | Ginn ............................ 606/151 |
| 6,780,197 B2 | 8/2004 | Roe et al. |
| 6,786,915 B2 | 9/2004 | Akerfeldt et al. |
| 6,790,218 B2 | 9/2004 | Jayaraman |
| 6,790,220 B2 | 9/2004 | Morris et al. |
| 6,837,893 B2 | 1/2005 | Miller |
| 6,837,906 B2 | 1/2005 | Ginn |
| 6,846,319 B2 | 1/2005 | Ginn et al. |
| 6,860,895 B1 | 3/2005 | Akerfeldt et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,913,607 B2 | 7/2005 | Ainsworth et al. |
| 6,926,723 B1 | 8/2005 | Mulhauser et al. |
| 6,926,731 B2 | 8/2005 | Coleman et al. |
| 6,929,634 B2 | 8/2005 | Dorros et al. |
| 6,942,641 B2 | 9/2005 | Seddon |
| 6,942,674 B2 | 9/2005 | Belef et al. |
| 6,942,691 B1 | 9/2005 | Chuter |
| 6,949,113 B2 | 9/2005 | Van Tassel et al. |
| 6,964,668 B2 | 11/2005 | Modesitt et al. |
| 6,969,391 B1 | 11/2005 | Gazzani |
| 6,969,397 B2 | 11/2005 | Ginn |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,011,671 B2 | 3/2006 | Welch |
| 7,025,776 B1 | 4/2006 | Houser et al. |
| 7,033,379 B2 | 4/2006 | Peterson |
| 7,060,084 B1 | 6/2006 | Loshakove et al. |
| 7,063,711 B1 | 6/2006 | Loshakove et al. |
| 7,074,232 B2 | 7/2006 | Kanner et al. |
| 7,076,305 B2 | 7/2006 | Imran et al. |
| 7,083,635 B2 | 8/2006 | Ginn |
| 7,087,064 B1 | 8/2006 | Hyde |
| 7,087,088 B2 | 8/2006 | Berg et al. |
| 7,108,709 B2 | 9/2006 | Cummins |
| 7,111,768 B2 | 9/2006 | Cummins et al. |
| 7,112,225 B2 | 9/2006 | Ginn |
| 7,144,411 B2 | 12/2006 | Ginn et al. |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,211,101 B2 | 5/2007 | Carley et al. |
| 7,220,268 B2 | 5/2007 | Blatter |
| 7,229,452 B2 | 6/2007 | Kayan |
| 7,261,716 B2 | 8/2007 | Strobel et al. |
| 7,306,614 B2 | 12/2007 | Weller et al. |
| 7,311,720 B2 | 12/2007 | Mueller et al. |
| 7,316,704 B2 | 1/2008 | Bagaoisan et al. |
| 7,316,706 B2 | 1/2008 | Bloom et al. |
| 7,322,995 B2 | 1/2008 | Buckman et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| D566,272 S | 4/2008 | Walburg et al. |
| 7,361,178 B2 | 4/2008 | Hearn et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,427,279 B2 | 9/2008 | Frazier et al. |
| 7,431,729 B2 | 10/2008 | Chanduszko |
| 7,445,596 B2 | 11/2008 | Kucklick et al. |
| 7,465,286 B2 | 12/2008 | Patterson et al. |
| 7,533,790 B1 | 5/2009 | Knodel et al. |
| 7,549,983 B2 | 6/2009 | Roue et al. |
| 7,556,632 B2 | 7/2009 | Zadno |
| 7,582,103 B2 | 9/2009 | Young et al. |
| 7,582,104 B2 | 9/2009 | Corcoran et al. |
| 7,597,704 B2 | 10/2009 | Frazier et al. |
| 7,597,706 B2 | 10/2009 | Kanner et al. |
| 7,618,427 B2 | 11/2009 | Ortiz et al. |
| 7,622,628 B2 | 11/2009 | Bergin et al. |
| D611,144 S | 3/2010 | Reynolds |
| 7,678,135 B2 | 3/2010 | Maahs et al. |
| 7,713,282 B2 | 5/2010 | Frazier et al. |
| 7,722,641 B2 | 5/2010 | van der Burg et al. |
| 7,727,189 B2 | 6/2010 | VanTassel et al. |
| 7,735,493 B2 | 6/2010 | van der Burg et al. |
| 7,780,696 B2 | 8/2010 | Daniel et al. |
| 7,806,904 B2 | 10/2010 | Carley et al. |
| 7,819,895 B2 | 10/2010 | Ginn et al. |
| 7,824,419 B2 | 11/2010 | Boraiah |
| 7,841,502 B2 | 11/2010 | Walberg et al. |
| 7,842,068 B2 | 11/2010 | Ginn |
| 7,850,709 B2 | 12/2010 | Cummins et al. |
| 7,850,710 B2 | 12/2010 | Huss |
| 7,850,797 B2 | 12/2010 | Carley et al. |
| 7,854,810 B2 | 12/2010 | Carley et al. |
| 7,857,828 B2 | 12/2010 | Jabba et al. |
| 7,867,249 B2 | 1/2011 | Palermo et al. |
| 7,875,054 B2 | 1/2011 | LaFontaine |
| 7,879,071 B2 | 2/2011 | Carley et al. |
| 7,887,555 B2 | 2/2011 | Carley et al. |

(56) References Cited

U.S. PATENT DOCUMENTS

| | | |
|---|---|---|
| 7,887,563 B2 | 2/2011 | Cummins et al. |
| 7,901,428 B2 | 3/2011 | Ginn et al. |
| 7,905,900 B2 | 3/2011 | Palermo |
| 7,918,873 B2 | 4/2011 | Cummins et al. |
| 7,931,669 B2 | 4/2011 | Ginn et al. |
| 7,931,671 B2 | 4/2011 | Tenerz |
| 7,967,842 B2 | 6/2011 | Bakos |
| 7,972,359 B2 | 7/2011 | Kreidler |
| 8,007,512 B2 | 8/2011 | Ginn et al. |
| 8,043,305 B2 | 10/2011 | Frazier et al. |
| 8,043,329 B2 | 10/2011 | Khairkhahan et al. |
| 8,052,715 B2 | 11/2011 | Quinn et al. |
| 8,080,032 B2 | 12/2011 | van der Burg et al. |
| 8,083,768 B2 | 12/2011 | Ginn et al. |
| 8,103,327 B2 | 1/2012 | Harlev et al. |
| 8,105,352 B2 | 1/2012 | Egnelöv |
| 8,128,644 B2 | 3/2012 | Carley et al. |
| 8,142,470 B2 | 3/2012 | Quinn et al. |
| 8,172,749 B2 | 5/2012 | Melsheimer |
| 8,182,497 B2 | 5/2012 | Carley et al. |
| 8,192,459 B2 | 6/2012 | Cummins et al. |
| 8,197,496 B2 | 6/2012 | Roue et al. |
| 8,197,527 B2 | 6/2012 | Borillo et al. |
| 8,202,283 B2 | 6/2012 | Carley et al. |
| 8,202,293 B2 | 6/2012 | Ellingwood et al. |
| 8,202,294 B2 | 6/2012 | Jabba et al. |
| 8,211,122 B2 | 7/2012 | McIntosh |
| 8,216,260 B2 | 7/2012 | Lam et al. |
| 8,221,384 B2 | 7/2012 | Frazier et al. |
| 8,221,445 B2 | 7/2012 | Van Tassel et al. |
| 8,226,681 B2 | 7/2012 | Clark et al. |
| 8,236,026 B2 | 8/2012 | Carley et al. |
| 8,257,390 B2 | 9/2012 | Carley et al. |
| 8,287,563 B2 | 10/2012 | Khairkhahan et al. |
| 8,303,624 B2 | 11/2012 | Fortson |
| 8,313,497 B2 | 11/2012 | Walberg et al. |
| 8,323,309 B2 | 12/2012 | Khairkhahan et al. |
| 8,323,312 B2 | 12/2012 | Clark |
| 8,398,656 B2 | 3/2013 | Palermo et al. |
| 8,398,676 B2 | 3/2013 | Roorda et al. |
| 8,403,929 B2 | 3/2013 | Weisshaupt et al. |
| 8,409,228 B2 | 4/2013 | Blatter et al. |
| 8,469,995 B2 | 6/2013 | Cummins et al. |
| 8,480,687 B2 | 7/2013 | Ducharme et al. |
| 8,486,092 B2 | 7/2013 | Carley et al. |
| 8,486,108 B2 | 7/2013 | Carley et al. |
| 8,518,057 B2 | 8/2013 | Walberg et al. |
| 8,523,897 B2 | 9/2013 | van der Burg et al. |
| 8,529,587 B2 | 9/2013 | Ellingwood et al. |
| 8,535,343 B2 | 9/2013 | van der Burg et al. |
| 8,556,930 B2 | 10/2013 | Ellingwood |
| 8,556,932 B2 | 10/2013 | Ziobro |
| 8,562,630 B2 | 10/2013 | Campbell |
| 8,574,244 B2 | 11/2013 | Reynolds |
| 8,579,932 B2 | 11/2013 | Pantages et al. |
| 8,585,836 B2 | 11/2013 | Carley et al. |
| 8,590,760 B2 | 11/2013 | Cummins et al. |
| 8,597,325 B2 | 12/2013 | Ginn |
| 8,603,108 B2 | 12/2013 | Roue et al. |
| 8,603,116 B2 | 12/2013 | Roorda |
| 8,603,136 B2 | 12/2013 | Ginn |
| 8,617,184 B2 | 12/2013 | Oepen |
| 8,647,361 B2 | 2/2014 | Borillo et al. |
| 8,657,852 B2 | 2/2014 | Roorda et al. |
| 8,663,268 B2 | 3/2014 | Quinn et al. |
| 8,663,273 B2 | 3/2014 | Khairkhahan et al. |
| 8,672,953 B2 | 3/2014 | Reyes et al. |
| 8,685,055 B2 | 4/2014 | VanTassel et al. |
| 8,834,494 B2 | 9/2014 | Schorr et al. |
| 8,992,549 B2 | 3/2015 | Bennett, III |
| 2001/0007077 A1 | 7/2001 | Ginn et al. |
| 2001/0021855 A1 | 9/2001 | Levinson |
| 2001/0031972 A1 | 10/2001 | Robertson et al. |
| 2001/0031973 A1 | 10/2001 | Nobles et al. |
| 2001/0044639 A1 | 11/2001 | Levinson |
| 2001/0046518 A1 | 11/2001 | Sawhney |
| 2001/0047180 A1 | 11/2001 | Grudem et al. |
| 2002/0022822 A1 | 2/2002 | Cragg et al. |
| 2002/0026215 A1 | 2/2002 | Redmond et al. |
| 2002/0026216 A1 | 2/2002 | Grimes |
| 2002/0029050 A1 | 3/2002 | Gifford, III et al. |
| 2002/0038127 A1 | 3/2002 | Blatter et al. |
| 2002/0042622 A1 | 4/2002 | Vargas et al. |
| 2002/0049427 A1 | 4/2002 | Wiener et al. |
| 2002/0049453 A1 | 4/2002 | Nobles et al. |
| 2002/0056460 A1 | 5/2002 | Boyd et al. |
| 2002/0058960 A1 | 5/2002 | Hudson et al. |
| 2002/0062104 A1 | 5/2002 | Ashby et al. |
| 2002/0077656 A1 | 6/2002 | Ginn et al. |
| 2002/0077657 A1 | 6/2002 | Ginn et al. |
| 2002/0077658 A1 | 6/2002 | Ginn |
| 2002/0082641 A1 | 6/2002 | Ginn et al. |
| 2002/0095164 A1 | 7/2002 | Andreas et al. |
| 2002/0095181 A1 | 7/2002 | Beyar |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0151921 A1 | 10/2002 | Kanner et al. |
| 2002/0151963 A1 | 10/2002 | Brown et al. |
| 2002/0169475 A1 | 11/2002 | Gainor et al. |
| 2002/0183786 A1 | 12/2002 | Girton |
| 2002/0183787 A1 | 12/2002 | Wahr et al. |
| 2002/0198562 A1 | 12/2002 | Akerfeldt et al. |
| 2002/0198589 A1 | 12/2002 | Leong |
| 2003/0004543 A1 | 1/2003 | Gleeson et al. |
| 2003/0009180 A1 | 1/2003 | Hinchliffe et al. |
| 2003/0018358 A1 | 1/2003 | Saadat |
| 2003/0018377 A1* | 1/2003 | Berg ............. A61B 17/064 623/1.11 |
| 2003/0023248 A1 | 1/2003 | Parodi |
| 2003/0032981 A1 | 2/2003 | Kanner et al. |
| 2003/0033006 A1 | 2/2003 | Phillips et al. |
| 2003/0045893 A1 | 3/2003 | Ginn |
| 2003/0055455 A1 | 3/2003 | Yang et al. |
| 2003/0060846 A1 | 3/2003 | Egnelov et al. |
| 2003/0065358 A1 | 4/2003 | Frecker et al. |
| 2003/0083679 A1 | 5/2003 | Grudem et al. |
| 2003/0093096 A1 | 5/2003 | McGuckin et al. |
| 2003/0093108 A1 | 5/2003 | Avellanet et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0139819 A1 | 7/2003 | Beer et al. |
| 2003/0144695 A1 | 7/2003 | McGuckin, Jr. et al. |
| 2003/0158578 A1 | 8/2003 | Pantages et al. |
| 2003/0167063 A1 | 9/2003 | Kerr |
| 2003/0195504 A1 | 10/2003 | Tallarida et al. |
| 2003/0208211 A1 | 11/2003 | Kortenbach |
| 2004/0002763 A1 | 1/2004 | Phillips et al. |
| 2004/0009205 A1 | 1/2004 | Sawhney |
| 2004/0044350 A1 | 3/2004 | Martin et al. |
| 2004/0049224 A1 | 3/2004 | Buehlmann et al. |
| 2004/0059376 A1 | 3/2004 | Breuniger |
| 2004/0068273 A1 | 4/2004 | Fariss et al. |
| 2004/0078053 A1 | 4/2004 | Berg et al. |
| 2004/0082906 A1 | 4/2004 | Tallarida et al. |
| 2004/0087985 A1 | 5/2004 | Loshakove et al. |
| 2004/0092962 A1 | 5/2004 | Thornton et al. |
| 2004/0092964 A1 | 5/2004 | Modesitt et al. |
| 2004/0092968 A1 | 5/2004 | Caro et al. |
| 2004/0092973 A1 | 5/2004 | Chanduszko et al. |
| 2004/0093024 A1 | 5/2004 | Lousararian et al. |
| 2004/0093027 A1 | 5/2004 | Fabisiak et al. |
| 2004/0097978 A1 | 5/2004 | Modesitt et al. |
| 2004/0106980 A1 | 6/2004 | Solovay et al. |
| 2004/0127940 A1 | 7/2004 | Ginn et al. |
| 2004/0143290 A1 | 7/2004 | Brightbill |
| 2004/0143291 A1 | 7/2004 | Corcoran et al. |
| 2004/0147957 A1 | 7/2004 | Pierson, III |
| 2004/0158127 A1 | 8/2004 | Okada |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0191277 A1 | 9/2004 | Sawhney et al. |

(56) References Cited

U.S. PATENT DOCUMENTS

| | | |
|---|---|---|
| 2004/0215232 A1 | 10/2004 | Belhe et al. |
| 2004/0225301 A1 | 11/2004 | Roop et al. |
| 2004/0243216 A1 | 12/2004 | Gregorich |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0038460 A1 | 2/2005 | Jayaraman |
| 2005/0038500 A1 | 2/2005 | Boylan et al. |
| 2005/0059982 A1 | 3/2005 | Zung et al. |
| 2005/0075654 A1 | 4/2005 | Kelleher |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravikumar |
| 2005/0119695 A1 | 6/2005 | Carley et al. |
| 2005/0121042 A1 | 6/2005 | Belhe et al. |
| 2005/0148818 A1 | 7/2005 | Mesallum |
| 2005/0149066 A1 | 7/2005 | Stafford |
| 2005/0149117 A1 | 7/2005 | Khosravi et al. |
| 2005/0152949 A1 | 7/2005 | Hotchkiss et al. |
| 2005/0154401 A1 | 7/2005 | Weldon et al. |
| 2005/0165357 A1 | 7/2005 | McGuckin et al. |
| 2005/0169974 A1 | 8/2005 | Tenerz et al. |
| 2005/0177189 A1 | 8/2005 | Ginn et al. |
| 2005/0187564 A1 | 8/2005 | Jayaraman |
| 2005/0203552 A1 | 9/2005 | Laufer et al. |
| 2005/0216057 A1 | 9/2005 | Coleman et al. |
| 2005/0222614 A1 | 10/2005 | Ginn et al. |
| 2005/0228405 A1 | 10/2005 | Maruyama et al. |
| 2005/0228443 A1 | 10/2005 | Yassinzadeh |
| 2005/0234508 A1* | 10/2005 | Cummins et al. ............ 606/213 |
| 2005/0245876 A1 | 11/2005 | Khosravi et al. |
| 2005/0256532 A1 | 11/2005 | Nayak et al. |
| 2005/0267495 A1 | 12/2005 | Ginn et al. |
| 2005/0267524 A1 | 12/2005 | Chanduszko |
| 2005/0273136 A1 | 12/2005 | Belef et al. |
| 2005/0273137 A1 | 12/2005 | Ginn |
| 2005/0283188 A1 | 12/2005 | Loshakove et al. |
| 2006/0030867 A1 | 2/2006 | Zadno |
| 2006/0034930 A1 | 2/2006 | Khosravi et al. |
| 2006/0047313 A1 | 3/2006 | Khanna et al. |
| 2006/0064115 A1 | 3/2006 | Allen et al. |
| 2006/0069397 A1 | 3/2006 | Nobles et al. |
| 2006/0100664 A1 | 5/2006 | Pai et al. |
| 2006/0142784 A1 | 6/2006 | Kontos |
| 2006/0190014 A1 | 8/2006 | Ginn et al. |
| 2006/0190036 A1 | 8/2006 | Wendel et al. |
| 2006/0190037 A1 | 8/2006 | Ginn et al. |
| 2006/0195123 A1 | 8/2006 | Ginn et al. |
| 2006/0195124 A1 | 8/2006 | Ginn et al. |
| 2006/0195125 A1 | 8/2006 | Sakakine et al. |
| 2006/0206146 A1 | 9/2006 | Tenerz |
| 2006/0217744 A1 | 9/2006 | Bender et al. |
| 2006/0229553 A1 | 10/2006 | Hammack et al. |
| 2006/0253037 A1 | 11/2006 | Ginn et al. |
| 2006/0253072 A1 | 11/2006 | Pai et al. |
| 2006/0287673 A1 | 12/2006 | Brett et al. |
| 2006/0287674 A1 | 12/2006 | Ginn et al. |
| 2006/0293698 A1 | 12/2006 | Douk |
| 2007/0005093 A1 | 1/2007 | Cox |
| 2007/0010851 A1 | 1/2007 | Chanduszko et al. |
| 2007/0010853 A1 | 1/2007 | Ginn et al. |
| 2007/0021778 A1 | 1/2007 | Carly |
| 2007/0027476 A1 | 2/2007 | Harris et al. |
| 2007/0027525 A1 | 2/2007 | Ben-Muvhar |
| 2007/0049968 A1 | 3/2007 | Sibbitt, Jr. et al. |
| 2007/0049970 A1 | 3/2007 | Belef et al. |
| 2007/0060858 A1 | 3/2007 | Sogard et al. |
| 2007/0060895 A1 | 3/2007 | Sibbitt, Jr. et al. |
| 2007/0060950 A1 | 3/2007 | Khosravi et al. |
| 2007/0073337 A1 | 3/2007 | Abbott et al. |
| 2007/0078302 A1 | 4/2007 | Ortiz et al. |
| 2007/0083230 A1 | 4/2007 | Javois |
| 2007/0083231 A1 | 4/2007 | Lee |
| 2007/0093869 A1 | 4/2007 | Bloom et al. |
| 2007/0112304 A1 | 5/2007 | Voss |
| 2007/0112365 A1 | 5/2007 | Hilal et al. |
| 2007/0112385 A1 | 5/2007 | Conlon |
| 2007/0123816 A1 | 5/2007 | Zhu et al. |
| 2007/0123817 A1 | 5/2007 | Khosravi et al. |
| 2007/0149996 A1 | 6/2007 | Coughlin |
| 2007/0167981 A1 | 7/2007 | Opolski et al. |
| 2007/0172430 A1 | 7/2007 | Brito et al. |
| 2007/0179527 A1 | 8/2007 | Eskuri et al. |
| 2007/0185529 A1 | 8/2007 | Coleman et al. |
| 2007/0185530 A1 | 8/2007 | Chin-Chen et al. |
| 2007/0203507 A1 | 8/2007 | McLaughlin et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0250080 A1 | 10/2007 | Jones et al. |
| 2007/0265658 A1 | 11/2007 | Nelson et al. |
| 2007/0275036 A1 | 11/2007 | Green, III et al. |
| 2007/0276488 A1 | 11/2007 | Wachter et al. |
| 2007/0282352 A1 | 12/2007 | Carley et al. |
| 2007/0282373 A1 | 12/2007 | Ashby et al. |
| 2008/0009794 A1 | 1/2008 | Bagaoisan et al. |
| 2008/0033459 A1 | 2/2008 | Shafi et al. |
| 2008/0045979 A1 | 2/2008 | Ma |
| 2008/0058839 A1 | 3/2008 | Nobles et al. |
| 2008/0065151 A1 | 3/2008 | Ginn |
| 2008/0065152 A1 | 3/2008 | Carley |
| 2008/0082123 A1 | 4/2008 | Forsberg et al. |
| 2008/0086075 A1 | 4/2008 | Isik et al. |
| 2008/0091235 A1 | 4/2008 | Sirota |
| 2008/0093414 A1 | 4/2008 | Bender et al. |
| 2008/0097509 A1 | 4/2008 | Beyar et al. |
| 2008/0114378 A1 | 5/2008 | Matsushita |
| 2008/0114395 A1 | 5/2008 | Mathisen et al. |
| 2008/0177288 A1 | 7/2008 | Carlson |
| 2008/0208225 A1 | 8/2008 | Seibold et al. |
| 2008/0210737 A1 | 9/2008 | Ginn et al. |
| 2008/0215089 A1 | 9/2008 | Williams et al. |
| 2008/0215090 A1 | 9/2008 | Gonzales et al. |
| 2008/0221616 A1 | 9/2008 | Ginn et al. |
| 2008/0243148 A1 | 10/2008 | Mikkaichi et al. |
| 2008/0243182 A1 | 10/2008 | Bates et al. |
| 2008/0249504 A1 | 10/2008 | Lattouf et al. |
| 2008/0269801 A1 | 10/2008 | Coleman et al. |
| 2008/0269802 A1 | 10/2008 | Coleman et al. |
| 2008/0272173 A1 | 11/2008 | Coleman et al. |
| 2008/0287988 A1 | 11/2008 | Smith et al. |
| 2008/0294001 A1 | 11/2008 | Surti |
| 2008/0300628 A1 | 12/2008 | Ellingwood |
| 2008/0312667 A1 | 12/2008 | Drasler et al. |
| 2008/0312686 A1 | 12/2008 | Ellingwood |
| 2008/0312740 A1 | 12/2008 | Wachter et al. |
| 2009/0054912 A1 | 2/2009 | Heanue et al. |
| 2009/0062846 A1 | 3/2009 | Ken |
| 2009/0112306 A1 | 4/2009 | Bonsignore et al. |
| 2009/0132031 A1 | 5/2009 | Cook et al. |
| 2009/0137900 A1 | 5/2009 | Bonner et al. |
| 2009/0157101 A1 | 6/2009 | Reyes et al. |
| 2009/0157102 A1 | 6/2009 | Reynolds et al. |
| 2009/0171388 A1 | 7/2009 | Dave et al. |
| 2009/0187215 A1 | 7/2009 | Mackiewicz et al. |
| 2009/0216267 A1 | 8/2009 | Willard et al. |
| 2009/0221960 A1 | 9/2009 | Albrecht et al. |
| 2009/0227938 A1 | 9/2009 | Fasching et al. |
| 2009/0230168 A1 | 9/2009 | Coleman et al. |
| 2009/0254119 A1 | 10/2009 | Sibbitt, Jr. et al. |
| 2009/0259233 A1 | 10/2009 | Bogart et al. |
| 2009/0281555 A1 | 11/2009 | Stone |
| 2009/0287244 A1 | 11/2009 | Kokish |
| 2009/0312789 A1 | 12/2009 | Kassab et al. |
| 2010/0042118 A1 | 2/2010 | Garrison et al. |
| 2010/0042144 A1 | 2/2010 | Bennett |
| 2010/0114119 A1 | 5/2010 | McLawhorn et al. |
| 2010/0114156 A1 | 5/2010 | Mehl |

(56) References Cited

U.S. PATENT DOCUMENTS

| | | |
|---|---|---|
| 2010/0130965 A1 | 5/2010 | Sibbitt, Jr. et al. |
| 2010/0168790 A1 | 7/2010 | Clark |
| 2010/0179567 A1 | 7/2010 | Voss et al. |
| 2010/0179571 A1 | 7/2010 | Voss |
| 2010/0179572 A1 | 7/2010 | Voss et al. |
| 2010/0179589 A1 | 7/2010 | Roorda et al. |
| 2010/0179590 A1 | 7/2010 | Fortson et al. |
| 2010/0185216 A1 | 7/2010 | Garrison et al. |
| 2010/0185234 A1 | 7/2010 | Fortson et al. |
| 2010/0217132 A1 | 8/2010 | Ellingwood et al. |
| 2010/0249828 A1 | 9/2010 | Mavani et al. |
| 2011/0054492 A1 | 3/2011 | Clark |
| 2011/0066164 A1 | 3/2011 | Walberg et al. |
| 2011/0082495 A1 | 4/2011 | Ruiz |
| 2011/0106148 A1 | 5/2011 | Ginn et al. |
| 2011/0137340 A1 | 6/2011 | Cummins |
| 2011/0144691 A1 | 6/2011 | Cummins |
| 2011/0166584 A1 | 7/2011 | Palermo et al. |
| 2011/0178548 A1 | 7/2011 | Tenerz |
| 2011/0190793 A1 | 8/2011 | Nobles et al. |
| 2011/0218568 A1 | 9/2011 | Voss |
| 2011/0270282 A1 | 11/2011 | Lemke |
| 2011/0288563 A1 | 11/2011 | Gianotti et al. |
| 2011/0313452 A1 | 12/2011 | Carley et al. |
| 2012/0029555 A1 | 2/2012 | Fortson et al. |
| 2012/0101520 A1 | 4/2012 | Ginn et al. |
| 2012/0143216 A1 | 6/2012 | Voss |
| 2012/0245623 A1 | 9/2012 | Kariniemi et al. |
| 2013/0053792 A1 | 2/2013 | Fischell et al. |
| 2013/0138144 A1 | 5/2013 | Yibarren |
| 2013/0190778 A1 | 7/2013 | Palermo |
| 2013/0253539 A1 | 9/2013 | Walberg et al. |
| 2013/0310853 A1 | 11/2013 | Zaugg et al. |
| 2013/0338708 A1 | 12/2013 | Cummins et al. |
| 2014/0005692 A1 | 1/2014 | Ellingwood et al. |
| 2014/0018850 A1 | 1/2014 | Ellingwood |
| 2014/0081318 A1 | 3/2014 | Houser et al. |
| 2014/0142624 A1 | 5/2014 | Pantages et al. |
| 2014/0180311 A1 | 6/2014 | Voss |
| 2014/0309686 A1 | 10/2014 | Ginn et al. |
| 2014/0364900 A1 | 12/2014 | Fortson et al. |
| 2014/0364903 A1 | 12/2014 | Roorda et al. |
| 2015/0073471 A1 | 3/2015 | Clark |
| 2015/0190071 A1 | 7/2015 | Ellingwood et al. |
| 2015/0265279 A1 | 9/2015 | Walberg et al. |

FOREIGN PATENT DOCUMENTS

| | | |
|---|---|---|
| DE | 197 11 288 | 10/1998 |
| DE | 29723736 U1 | 4/1999 |
| DE | 19859952 | 2/2000 |
| DE | 102006056283 | 6/2008 |
| EP | 0 386 361 | 9/1990 |
| EP | 0 534 696 | 3/1993 |
| EP | 0 621 032 | 10/1994 |
| EP | 0 756 851 | 2/1997 |
| EP | 0 774 237 | 5/1997 |
| EP | 0 858 776 | 8/1998 |
| EP | 0 941 697 | 9/1999 |
| EP | 1 867 287 | 12/2007 |
| FR | 2 443 238 | 7/1980 |
| FR | 2 715 290 | 7/1995 |
| FR | 2 722 975 | 2/1996 |
| FR | 2 768 324 | 3/1999 |
| GB | 1 358 466 | 7/1974 |
| GB | 2 075 144 | 11/1981 |
| GB | 2 397 240 | 7/2004 |
| IE | S2000/0722 | 10/2001 |
| IE | S2000/0724 | 10/2001 |
| IE | S2001/0547 | 7/2002 |
| IE | S2001/0815 | 7/2002 |
| IE | S2001/0748 | 8/2002 |
| IE | S2001/0749 | 8/2002 |
| IE | S2002/0452 | 12/2002 |
| IE | S2002/0664 | 2/2003 |
| IE | S2002/0665 | 2/2003 |
| IE | S2002/0451 | 7/2003 |
| IE | S2002/0552 | 7/2003 |
| IE | S2003/0424 | 12/2003 |
| IE | S2003/0490 | 1/2004 |
| IE | S2004/0368 | 11/2005 |
| IE | S2005/0342 | 11/2005 |
| JP | 58-181006 | 12/1983 |
| JP | 12 74750 | 11/1989 |
| JP | 11500642 | 8/1997 |
| JP | 2000102546 | 4/2000 |
| NL | 9302140 | 7/1995 |
| PL | 171425 | 4/1997 |
| RU | 2086192 | 8/1997 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 96/24291 | 8/1996 |
| WO | WO 97/00046 | 1/1997 |
| WO | WO 97/07741 | 3/1997 |
| WO | WO 97/20505 | 6/1997 |
| WO | WO 97/27897 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/40849 | 8/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/62234 | 8/2002 |
| WO | WO 02/98302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/094748 | 11/2003 |
| WO | WO 03/101310 | 12/2003 |
| WO | WO 2004/004578 | 1/2004 |
| WO | WO 2004/012602 | 2/2004 |
| WO | WO 2004/060169 | 7/2004 |
| WO | WO 2004/069054 | 8/2004 |
| WO | WO 2005/000126 | 1/2005 |
| WO | WO 2005/006990 | 1/2005 |
| WO | WO 2005/041782 | 5/2005 |
| WO | WO 2005/063129 | 7/2005 |

(56) References Cited

FOREIGN PATENT DOCUMENTS

| | | |
|---|---|---|
| WO | WO 2005/082256 | 9/2005 |
| WO | WO 2005/092204 | 10/2005 |
| WO | WO 2005/110240 | 11/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/081836 | 7/2007 |
| WO | WO 2007/088069 | 8/2007 |
| WO | WO 2008/031102 | 3/2008 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 200100527 | 1/2001 |
| ZA | 200100528 | 1/2001 |

OTHER PUBLICATIONS

U.S. Appl. No. 09/866,551, filed May 25, 2001, Ginn.
U.S. Appl. No. 12/113,092, filed Apr. 30, 2008, Ginn et al.
U.S. Appl. No. 13/017,636, filed Jan. 31, 2011, Carley et al.
U.S. Appl. No. 60/693,531, filed Jun. 24, 2005, Carly.
U.S. Appl. No. 60/696,069, filed Jul. 1, 2005, Pantages et al.
U.S. Appl. No. 60/793,444, filed Apr. 20, 2006, Jones et al.
U.S. Appl. No. 60/946,026, filed Jun. 25, 2007, Ellingwood.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 61/015,144, filed Dec. 19, 2007, Mackiewicz et al.
U.S. Appl. No. 61/109,822, filed Oct. 30, 2008, Mehl et al.
U.S. Appl. No. 61/139,995, filed Dec. 22, 2008, Clark.
U.S. Appl. No. 61/141,597, filed Dec. 30, 2008, Clark.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
U.S. Appl. No. 14/246,926, filed Apr. 7, 2014, Carley et al.
"Hand tool for forming telephone connections—comprises pliers with reciprocably driven ram crimping clip around conductors against anvil", Derwent-ACC-No. 1978-B8090A. (Jan. 10, 1978).
Database WPI; Section PQ, Week 200120; Derwent Publications Ltd., London GB; Class P31, AN 2001-203165; XP002199926 & ZA 200 100 528 A (Anthony T), Feb. 28, 2001 abstract.
Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 71—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert PHD, Wound Closure Biomaterials and Devices, Shock., Mar. 1999, p. 226, vol. 11—No. 3, Institution Northwestern University (editorial review).
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
Marshall A.C., Lock J.E., Structural and Compliant Anatomy of the Patent Foramen Ovale in Patients Undergoing Transcatheter Closure, Am Heart J Aug. 2000; 140(2); pp. 303-307.
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.
Michael Gianturco, A Play on Catheterization, Forbes, Dec. 1996, p. 146, vol. 158—No. 15.
Inlet Medical Inc. Brochure, pp. 1-2, referencing Om Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.
P M N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.
ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.
SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).

(56) References Cited

OTHER PUBLICATIONS

Scott Hensley, Closing Wounds. New Devices seal arterial punctures in double time, Modern Healthcare (United States), Mar. 23, 2008, p. 48.
Sigmund Silber et al, A novel vascular device for closure of percutaneous arterial access sites, The American Journal of Cardiology, Apr. 1999, pp. 1248-1252, vol. 83—No. 8.
Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.
Stretch Comb by Scunci, retrieved via internet at www.scunci.com/productdetail by examiner on Oct. 9, 2007, publication date unavailable.
Swee Lian Tan, MD, PHD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.
SY Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.
Taber's Cyclopedic Medical Dictionary, 18th Ed. 1997, pp. 747 and 1420.
Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.
Tomoaki Hinohara, Percutaneous vascular surgery (Prostar® Plus and Techstar® for femoral artery site closure), Interventional Cardiology Newsletter, May-Jul. 1997, pp. 19-22, pp. 24-28, vol. 5—No. 3-4.
UT Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.
Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.
William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.
Turn—macmillandictionary.com/dictionary.american/turn.
Turn—Merriam-webster.com/dictionary/turn.
U.S. Appl. No. 09/478,179, Nov. 6, 2000, Notice of Allowance.
U.S. Appl. No. 09/546,998, May 6, 2002, Notice of Allowance.
U.S. Appl. No. 09/610,238, Mar. 26, 2001, Notice of Allowance.
U.S. Appl. No. 09/610,238, Sep. 5, 2001, Office Action.
U.S. Appl. No. 09/610,238, Feb. 11, 2002, Notice of Allowance.
U.S. Appl. No. 09/680,837, Jul. 9, 2002, Office Action.
U.S. Appl. No. 09/680,837, Nov. 6, 2002, Office Action.
U.S. Appl. No. 09/680,837, Mar. 25, 2003, Office Action.
U.S. Appl. No. 09/680,837, Jun. 16, 2003, Notice of Allowance.
U.S. Appl. No. 09/732,178, Aug. 1, 2002, Office Action.
U.S. Appl. No. 09/732,178, Dec. 24, 2002, Office Action.
U.S. Appl. No. 09/732,178, Jun. 10, 2003, Office Action.
U.S. Appl. No. 09/732,178, Jul. 3, 2003, Office Action.
U.S. Appl. No. 09/732,178, Nov. 17, 2003, Notice of Allowance.
U.S. Appl. No. 09/732,835, Sep. 11, 2003, Office Action.
U.S. Appl. No. 09/732,835, Feb. 9, 2004, Office Action.
U.S. Appl. No. 09/732,835, Mar. 17, 2004, Notice of Allowance.
U.S. Appl. No. 09/764,813, Mar. 26, 2001, Office Action.
U.S. Appl. No. 09/764,813, Jun. 4, 2001, Notice of Allowance.
U.S. Appl. No. 09/933,299, Feb. 26, 2003, Office Action.
U.S. Appl. No. 09/933,299, Jun. 16, 2003, Notice of Allowance.
U.S. Appl. No. 09/948,813, Jan. 31, 2003, Notice of Allowance.
U.S. Appl. No. 09/949,398, Mar. 4, 2003, Office Action.
U.S. Appl. No. 09/949,398, Jul. 28, 2003, Notice of Allowance.
U.S. Appl. No. 09/949,438, Dec. 17, 2002, Office Action.
U.S. Appl. No. 09/949,438, Apr. 21, 2003, Notice of Allowance.
U.S. Appl. No. 10/006,400, Aug. 27, 2004, Office Action.
U.S. Appl. No. 10/006,400, Feb. 23, 2005, Office Action.
U.S. Appl. No. 10/006,400, Apr. 11, 2005, Office Action.
U.S. Appl. No. 10/006,400, Jul. 27, 2005, Office Action.
U.S. Appl. No. 10/006,400, Mar. 6, 2006, Office Action.
U.S. Appl. No. 10/006,400, May 24, 2006, Office Action.
U.S. Appl. No. 10/006,400, Oct. 26, 2006, Office Action.
U.S. Appl. No. 10/006,400, Apr. 19, 2007, Office Action.
U.S. Appl. No. 10/006,400, Apr. 2, 2008, Office Action.
U.S. Appl. No. 10/006,400, Jan. 2, 2009, Office Action.
U.S. Appl. No. 10/006,400, Jul. 9, 2009, Notice of Allowance.
U.S. Appl. No. 10/006,400, Jan. 13, 2010, Notice of Allowance.
U.S. Appl. No. 10/006,400, Apr. 27, 2010, Notice of Allowance.
U.S. Appl. No. 10/006,400, Aug. 2, 2010, Notice of Allowance.
U.S. Appl. No. 10/081,717, Sep. 29, 2003, Notice of Allowance.
U.S. Appl. No. 10/081,723, Sep. 29, 2004, Office Action.
U.S. Appl. No. 10/081,723, May 13, 2005, Notice of Allowance.
U.S. Appl. No. 10/081,725, Feb. 9, 2004, Notice of Allowance.
U.S. Appl. No. 10/081,725, Apr. 13, 2004, Office Action.
U.S. Appl. No. 10/081,726, Apr. 11, 2003, Notice of Allowance.
U.S. Appl. No. 10/081,726, Jun. 9, 2003, Notice of Allowance.
U.S. Appl. No. 10/147,774, Nov. 4, 2004, Office Action.
U.S. Appl. No. 10/147,774, May 4, 2005, Office Action.
U.S. Appl. No. 10/147,774, Oct. 18, 2005, Office Action.
U.S. Appl. No. 10/147,774, Apr. 18, 2007, Notice of Allowance.
U.S. Appl. No. 10/147,774, Sep. 27, 2007, Notice of Allowance.
U.S. Appl. No. 10/147,774, Feb. 4, 2008 Notice of Allowance.
U.S. Appl. No. 10/147,774, Jun. 30, 2008, Office Action.
U.S. Appl. No. 10/147,774, Mar. 18, 2009, Office Action.
U.S. Appl. No. 10/147,774, Oct. 26, 2009, Office Action.
U.S. Appl. No. 10/147,774, Jun. 8, 2010, Office Action.
U.S. Appl. No. 10/147,774, Dec. 2, 2010, Notice of Allowance.
U.S. Appl. No. 10/240,183, Jul. 27, 2004, Office Action.
U.S. Appl. No. 10/240,183, Dec. 17, 2004, Office Action.
U.S. Appl. No. 10/240,183, Mar. 9, 2005, Notice of Allowance.
U.S. Appl. No. 10/240,183, Aug. 11, 2006, Office Action.
U.S. Appl. No. 10/264,306, Feb. 9, 2005, Office Action.
U.S. Appl. No. 10/264,306, Oct. 4, 2005, Office Action.
U.S. Appl. No. 10/264,306, May 10, 2006, Notice of Allowance.
U.S. Appl. No. 10/264,306, Jul. 2, 2007, Notice of Allowance.
U.S. Appl. No. 10/264,306, Feb. 4, 2008, Notice of Allowance.
U.S. Appl. No. 10/264,306, Jun. 27, 2008, Office Action.
U.S. Appl. No. 10/264,306, Feb. 26, 2009, Office Action.
U.S. Appl. No. 10/264,306, Aug. 13, 2009, Office Action.
U.S. Appl. No. 10/264,306, Jan. 27, 2010, Office Action.
U.S. Appl. No. 10/264,306, Jun. 15, 2010, Office Action.
U.S. Appl. No. 10/264,306, Oct. 29, 2010, Notice of Allowance.
U.S. Appl. No. 10/335,075, Aug. 10, 2005, Office Action.
U.S. Appl. No. 10/335,075, Dec. 19, 2005, Office Action.
U.S. Appl. No. 10/335,075, Apr. 21, 2006, Office Action.
U.S. Appl. No. 10/335,075, Dec. 27, 2006, Notice of Allowance.
U.S. Appl. No. 10/356,214, Nov. 30, 2005, Office Action.
U.S. Appl. No. 10/356,214, Aug. 23, 2006, Office Action.
U.S. Appl. No. 10/356,214, Feb. 13, 2007, Office Action.
U.S. Appl. No. 10/356,214, Sep. 12, 2007, Office Action.
U.S. Appl. No. 10/356,214, Mar. 6, 2008, Office Action.
U.S. Appl. No. 10/356,214, Nov. 4, 2008, Office Action.
U.S. Appl. No. 10/356,214, Apr. 29, 2009, Office Action.
U.S. Appl. No. 10/356,214, Jan. 13, 2010, Notice of Allowance.
U.S. Appl. No. 10/356,214, May 13, 2010, Notice of Allowance.
U.S. Appl. No. 10/356,214, Sep. 3, 2010, Notice of Allowance.
U.S. Appl. No. 10/435,104, Jun. 10, 2004, Office Action.
U.S. Appl. No. 10/435,104, Sep. 21, 2004, Notice of Allowance.
U.S. Appl. No. 10/435,104, Jan. 3, 2006, Examiner's Amendment.
U.S. Appl. No. 10/435,104, May 16, 2006, Office Action.
U.S. Appl. No. 10/435,104, Dec. 28, 2006, Notice of Allowance.
U.S. Appl. No. 10/435,104, Jul. 10, 2007, Notice of Allowance.

(56) References Cited

OTHER PUBLICATIONS

U.S. Appl. No. 10/435,104, Aug. 2, 2007, Notice of Allowance.
U.S. Appl. No. 10/435,104, Oct. 26, 2007, Notice of Allowance.
U.S. Appl. No. 10/435,104, Nov. 14, 2007, Notice of Allowance.
U.S. Appl. No. 10/435,104, Apr. 4, 2008, Notice of Allowance.
U.S. Appl. No. 10/435,104, Sep. 26, 2008, Notice of Allowance.
U.S. Appl. No. 10/435,104, Dec. 22, 2008, Notice of Allowance.
U.S. Appl. No. 10/435,104, Jul. 23, 2009, Notice of Allowance.
U.S. Appl. No. 10/435,104, Jan. 20, 2010, Notice of Allowance.
U.S. Appl. No. 10/435,104, Jun. 2, 2010, Office Action.
U.S. Appl. No. 10/435,104, Oct. 5, 2010, Notice of Allowance.
U.S. Appl. No. 10/455,768, Nov. 16, 2004, Office Action.
U.S. Appl. No. 10/455,768, Apr. 6, 2005, Notice of Allowance.
U.S. Appl. No. 10/486,067, Jan. 10, 2006, Office Action.
U.S. Appl. No. 10/486,067, Sep. 20, 2006, Notice of Allowance.
U.S. Appl. No. 10/486,070, Apr. 20, 2005, Office Action.
U.S. Appl. No. 10/486,070, Aug. 10, 2005, Office Action.
U.S. Appl. No. 10/486,070, Oct. 18, 2005, Notice of Allowance.
U.S. Appl. No. 10/517,004, Aug. 13, 2007, Office Action.
U.S. Appl. No. 10/517,004, Jan. 30, 2008, Office Action.
U.S. Appl. No. 10/517,004, Aug. 13, 2008, Notice of Allowance.
U.S. Appl. No. 10/517,004, Feb. 10, 2009, Notice of Allowance.
U.S. Appl. No. 10/517,004, Mar. 24, 2009, Notice of Allowance.
U.S. Appl. No. 10/517,004, Jun. 26, 2009, Notice of Allowance.
U.S. Appl. No. 10/517,004, Jan. 11, 2010, Notice of Allowance.
U.S. Appl. No. 10/517,004, Apr. 23, 2010, Notice of Allowance.
U.S. Appl. No. 10/517,004, Aug. 3, 2010, Notice of Allowance.
U.S. Appl. No. 10/519,778, Feb. 23, 2006, Office Action.
U.S. Appl. No. 10/519,778, May 31, 2006, Notice of Allowance.
U.S. Appl. No. 10/541,083, Oct. 16, 2007, Office Action.
U.S. Appl. No. 10/541,083, Oct. 31, 2007, Office Action.
U.S. Appl. No. 10/541,083, May 5, 2008, Office Action.
U.S. Appl. No. 10/541,083, Sep. 19, 2008, Notice of Allowance.
U.S. Appl. No. 10/541,083, Dec. 29, 2008, Notice of Allowance.
U.S. Appl. No. 10/541,083, Apr. 16, 2009, Notice of Allowance.
U.S. Appl. No. 10/541,083, Sep. 30, 2009, Notice of Allowance.
U.S. Appl. No. 10/541,083, Feb. 5, 2010, Notice of Allowance.
U.S. Appl. No. 10/541,083, May 10, 2010, Notice of Allowance.
U.S. Appl. No. 10/541,083, Aug. 17, 2010, Notice of Allowance.
U.S. Appl. No. 10/616,832, Jun. 30, 2006, Office Action.
U.S. Appl. No. 10/616,832, Oct. 20, 2006, Office Action.
U.S. Appl. No. 10/616,832, May 29, 2007, Office Action.
U.S. Appl. No. 10/616,832, Jan. 22, 2008, Office Action.
U.S. Appl. No. 10/616,832, Sep. 17, 2008, Office Action.
U.S. Appl. No. 10/616,832, Jul. 21, 2009, Office Action.
U.S. Appl. No. 10/616,832, Jan. 11, 2010, Notice of Allowance.
U.S. Appl. No. 10/616,832, May 12, 2010, Notice of Allowance.
U.S. Appl. No. 10/616,832, Sep. 20, 2010, Notice of Allowance.
U.S. Appl. No. 10/617,090, Mar. 22, 2005, Office Action.
U.S. Appl. No. 10/617,090, Jul. 6, 2005, Notice of Allowance.
U.S. Appl. No. 10/617,090, Oct. 5, 2005, Notice of Allowance.
U.S. Appl. No. 10/638,115, Sep. 22, 2006, Office Action.
U.S. Appl. No. 10/638,115, Jan. 31, 2007, Office Action.
U.S. Appl. No. 10/638,115, Sep. 18, 2007, Office Action.
U.S. Appl. No. 10/638,115, Feb. 7, 2008, Office Action.
U.S. Appl. No. 10/638,115, Oct. 29, 2008, Office Action.
U.S. Appl. No. 10/638,115, May 7, 2009, Notice of Allowance.
U.S. Appl. No. 10/638,115, Dec. 1, 2009, Notice of Allowance.
U.S. Appl. No. 10/638,115 Apr. 2, 2010, Notice of Allowance.
U.S. Appl. No. 10/638,115, Aug. 13, 2010, Notice of Allowance.
U.S. Appl. No. 10/667,144, Sep. 19, 2006, Office Action.
U.S. Appl. No. 10/667,144, May 2, 2007, Office Action.
U.S. Appl. No. 10/667,144, Nov. 19, 2007, Office Action.
U.S. Appl. No. 10/667,144, Dec. 5, 2007, Office Action.
U.S. Appl. No. 10/667,144, May 12, 2008, Office Action.
U.S. Appl. No. 10/667,144, Mar. 24, 2009, Office Action.
U.S. Appl. No. 10/667,144, Nov. 23, 2009, Office Action.
U.S. Appl. No. 10/667,144, Jun. 22, 2010, Office Action.
U.S. Appl. No. 10/667,144, Jun. 6, 2011, Office Action.
U.S. Appl. No. 10/667,144, Oct. 28, 2011, Notice of Allowance.
U.S. Appl. No. 10/669,313, Oct. 31, 2005, Office Action.
U.S. Appl. No. 10/669,313, Jan. 11, 2006, Notice of Allowance.
U.S. Appl. No. 10/669,313, Jun. 28, 2006, Notice of Allowance.
U.S. Appl. No. 10/682,459, Sep. 15, 2006, Office Action.
U.S. Appl. No. 10/682,459, Apr. 18, 2007, Office Action.
U.S. Appl. No. 10/682,459, Apr. 2, 2008, Office Action.
U.S. Appl. No. 10/682,459, Dec. 4, 2008, Office Action.
U.S. Appl. No. 10/682,459, Jun. 10, 2009, Office Action.
U.S. Appl. No. 10/682,459, Dec. 23, 2009, Office Action.
U.S. Appl. No. 10/682,459, Apr. 28, 2010, Office Action.
U.S. Appl. No. 10/682,459, Oct. 12, 2010, Office Action.
U.S. Appl. No. 10/682,459, Apr. 1, 2011, Notice of Allowance.
U.S. Appl. No. 10/786,444, Oct. 30, 2006, Office Action.
U.S. Appl. No. 10/786,444, Apr. 17, 2007, Office Action.
U.S. Appl. No. 10/786,444, Aug. 31, 2007, Office Action.
U.S. Appl. No. 10/786,444, Apr. 24, 2008, Office Action.
U.S. Appl. No. 10/786,444, Oct. 17, 2008, Office Action.
U.S. Appl. No. 10/786,444, Jun. 18, 2009, Office Action.
U.S. Appl. No. 10/786,444, Jan. 14, 2010, Office Action.
U.S. Appl. No. 10/786,444, Jul. 11, 2013, Notice of Allowance.
U.S. Appl. No. 10/787,073, Nov. 30, 2006, Office Action.
U.S. Appl. No. 10/787,073, Sep. 5, 2007, Office Action.
U.S. Appl. No. 10/787,073, Feb. 22, 2008, Office Action.
U.S. Appl. No. 10/787,073, Nov. 12, 2008, Office Action.
U.S. Appl. No. 10/787,073, Aug. 13, 2009, Office Action.
U.S. Appl. No. 10/787,073, Feb. 17, 2010, Notice of Allowance.
U.S. Appl. No. 10/787,073, Aug. 25, 2010, Notice of Allowance.
U.S. Appl. No. 10/908,721, Oct. 19, 2006, Office Action.
U.S. Appl. No. 10/908,721, Aug. 10, 2007, Office Action.
U.S. Appl. No. 10/908,721, Jan. 25, 2008, Office Action.
U.S. Appl. No. 10/908,721, Nov. 25, 2008, Office Action.
U.S. Appl. No. 10/908,721, Jun. 23, 2009, Office Action.
U.S. Appl. No. 10/908,721, Feb. 2, 2010, Office Action.
U.S. Appl. No. 10/908,721, Jul. 18, 2013, Notice of Allowance.
U.S. Appl. No. 11/048,503, Mar. 13, 2009, Office Action.
U.S. Appl. No. 11/048,503, Jun. 26, 2009, Office Action.
U.S. Appl. No. 11/048,503, Jan. 11, 2010, Notice of Allowance.
U.S. Appl. No. 11/048,503, Apr. 26, 2010, Notice of Allowance.
U.S. Appl. No. 11/048,503, Jul. 30, 2010, Notice of Allowance.
U.S. Appl. No. 11/113,549, Feb. 6, 2007, Office Action.
U.S. Appl. No. 11/113,549, May 30, 2007, Office Action.
U.S. Appl. No. 11/113,549, Nov. 9, 2007, Office Action.
U.S. Appl. No. 11/113,549, Apr. 16, 2008, Office Action.
U.S. Appl. No. 11/113,549, Jul. 21, 2009, Office Action.
U.S. Appl. No. 11/113,549, Jul. 6, 2010, Office Action.
U.S. Appl. No. 11/113,549, Jan. 4, 2011, Office Action.
U.S. Appl. No. 11/113,549, Mar. 14, 2014, Notice of Allowance.
U.S. Appl. No. 11/152,562, May 13, 2008, Office Action.
U.S. Appl. No. 11/152,562, Feb. 13, 2009, Office Action.
U.S. Appl. No. 11/152,562, Jul. 6, 2009, Office Action.
U.S. Appl. No. 11/152,562, Mar. 31, 2010, Office Action.
U.S. Appl. No. 11/152,562, Sep. 16, 2010, Notice of Allowance.
U.S. Appl. No. 11/198,811, Aug. 26, 2008, Office Action.
U.S. Appl. No. 11/198,811, Apr. 6, 2009, Office Action.
U.S. Appl. No. 11/198,811, Sep. 22, 2009, Office Action.
U.S. Appl. No. 11/198,811, Jun. 29, 2010, Notice of Allowance.
U.S. Appl. No. 11/344,793, Jan. 22, 2009, Office Action.
U.S. Appl. No. 11/344,868, Mar. 25, 2009, Office Action.
U.S. Appl. No. 11/344,891, Apr. 29, 2008, Office Action.
U.S. Appl. No. 11/344,891, Dec. 8, 2008, Office Action.
U.S. Appl. No. 11/344,891, Feb. 26, 2009, Office Action.
U.S. Appl. No. 11/344,891, Oct. 7, 2009, Office Action.
U.S. Appl. No. 11/344,891, May 7, 2010, Office Action.
U.S. Appl. No. 11/344,891, Jan. 22, 2013, Notice of Allowance.
U.S. Appl. No. 11/390,586, Jun. 24, 2009, Office Action.
U.S. Appl. No. 11/390,586, Jul. 6, 2010, Office Action.
U.S. Appl. No. 11/390,586, May 3, 2012, Notice of Allowance.
U.S. Appl. No. 11/396,141, May 22, 2009 Office Action.
U.S. Appl. No. 11/396,141, Aug. 26, 2009, Office Action.
U.S. Appl. No. 11/396,141, May 4, 2010, Office Action.
U.S. Appl. No. 11/396,141, Apr. 30, 2013, Office Action.
U.S. Appl. No. 11/396,141, Aug. 21, 2013, Office Action.
U.S. Appl. No. 11/396,141, Nov. 4, 2013, Notice of Allowance.

(56) References Cited

OTHER PUBLICATIONS

U.S. Appl. No. 11/396,141, Mar. 19, 2014, Issue Notifiaction.
U.S. Appl. No. 11/396,731, Feb. 13, 2009, Office Action.
U.S. Appl. No. 11/396,731, May 22, 2009, Office Action.
U.S. Appl. No. 11/396,731, Jun. 29, 2010, Office Action.
U.S. Appl. No. 11/396,731, Mar. 22, 2011, Office Action.
U.S. Appl. No. 11/396,731, Sep. 1, 2011, Office Action.
U.S. Appl. No. 11/406,203, May 14, 2007, Office Action.
U.S. Appl. No. 11/406,203, Jan. 29, 2008, Notice of Allowance.
U.S. Appl. No. 11/406,203, May 23, 2008, Notice of Allowance.
U.S. Appl. No. 11/406,203, Sep. 22, 2008, Notice of Allowance.
U.S. Appl. No. 11/406,203, Mar. 3, 2009, Office Action.
U.S. Appl. No. 11/406,203, Sep. 16, 2009, Office Action.
U.S. Appl. No. 11/406,203, Jun. 18, 2010, Notice of Allowance.
U.S. Appl. No. 11/411,925, Jun. 6, 2007, Office Action.
U.S. Appl. No. 11/411,925, Feb. 5, 2008, Office Action.
U.S. Appl. No. 11/411,925, Jan. 12, 2009, Office Action.
U.S. Appl. No. 11/411,925, Sep. 10, 2009, Office Action.
U.S. Appl. No. 11/411,925, Oct. 1, 2013, Office Action.
U.S. Appl. No. 11/411,925, Feb. 5, 2014, Notice of Allowance.
U.S. Appl. No. 11/427,297, Jan. 30, 2009, Office Action.
U.S. Appl. No. 11/427,297, Sep. 15, 2009, Office Action.
U.S. Appl. No. 11/427,297, Sep. 15, 2010, Office Action.
U.S. Appl. No. 11/427,297, Mar. 21, 2011, Office Action.
U.S. Appl. No. 11/427,297, Jun. 26, 2012, Notice of Allowance.
U.S. Appl. No. 11/427,309, May 28, 2008, Office Action.
U.S. Appl. No. 11/427,309, Jan. 2, 2009, Office Action.
U.S. Appl. No. 11/427,309, Apr. 20, 2009, Office Action.
U.S. Appl. No. 11/427,309, Nov. 6, 2009, Office Action.
U.S. Appl. No. 11/427,309, Apr. 26, 2010, Office Action.
U.S. Appl. No. 11/427,309, Nov. 15, 2010, Office Action.
U.S. Appl. No. 11/427,309, Jun. 7, 2013, Notice of Allowance.
U.S. Appl. No. 11/455,993, Feb. 17, 2009, Office Action.
U.S. Appl. No. 11/455,993, Dec. 16, 2009, Office Action.
U.S. Appl. No. 11/455,993, Jan. 29, 2014, Office Action.
U.S. Appl. No. 11/532,325, Feb. 23, 2009, Office Action.
U.S. Appl. No. 11/532,325, Jun. 17, 2009, Office Action.
U.S. Appl. No. 11/532,325, Jan. 5, 2010, Office Action.
U.S. Appl. No. 11/532,325, Jul. 17, 2013, Office Action.
U.S. Appl. No. 11/532,325, Dec. 2, 2013, Office Action.
U.S. Appl. No. 11/532,576, Mar. 1, 2010, Office Action.
U.S. Appl. No. 11/532,576, Apr. 23, 2010, Office Action.
U.S. Appl. No. 11/532,576, Oct. 13, 2010, Notice of Allowance.
U.S. Appl. No. 11/674,930, Jan. 8, 2009, Office Action.
U.S. Appl. No. 11/674,930, Jun. 4, 2009, Office Action.
U.S. Appl. No. 11/674,930, Jan. 8, 2010, Office Action.
U.S. Appl. No. 11/674,930, Apr. 3, 2014, Notice of Allowance.
U.S. Appl. No. 11/675,462, Dec. 10, 2009, Office Action.
U.S. Appl. No. 11/675,462, Aug. 31, 2010, Office Action.
U.S. Appl. No. 11/675,462, Aug. 3, 2011, Office Action.
U.S. Appl. No. 11/675,462, Dec. 22, 2011, Notice of Allowance.
U.S. Appl. No. 11/744,089, Nov. 26, 2008, Office Action.
U.S. Appl. No. 11/744,089, Aug. 14, 2009, Office Action.
U.S. Appl. No. 11/744,089, Aug. 8, 2012, Office Action.
U.S. Appl. No. 11/744,089, Apr. 15, 2013, Office Action.
U.S. Appl. No. 11/744,089, Aug. 8, 2013, Notice of Allowance.
U.S. Appl. No. 11/757,108, Nov. 25, 2009, Office Action.
U.S. Appl. No. 11/767,818, Dec. 24, 2009, Office Action.
U.S. Appl. No. 11/767,818, Mar. 22, 2010, Office Action.
U.S. Appl. No. 11/767,818, Sep. 30, 2010, Office Action.
U.S. Appl. No. 11/767,818, Feb. 16, 2011, Office Action.
U.S. Appl. No. 11/767,818, Feb. 3, 2012, Notice of Allowance.
U.S. Appl. No. 11/852,190, Jun. 24, 2010, Office Action.
U.S. Appl. No. 11/852,190, Nov. 1, 2010, Office Action.
U.S. Appl. No. 11/852,190, Mar. 2, 2011, Office Action.
U.S. Appl. No. 11/852,190, Apr. 24, 2013, Office Action.
U.S. Appl. No. 11/852,190, Nov. 26, 2013, Office Action.
U.S. Appl. No. 11/852,190, Feb. 12, 2014, Notice of Allowance.
U.S. Appl. No. 11/958,281, Sep. 2, 2010, Office Action.
U.S. Appl. No. 11/958,281, Oct. 8, 2010, Office Action.
U.S. Appl. No. 11/958,281, Mar. 10, 2011, Office Action.
U.S. Appl. No. 11/958,295, Aug. 27, 2009, Office Action.
U.S. Appl. No. 11/958,295, May 25, 2010, Office Action.
U.S. Appl. No. 11/959,334, Aug. 19, 2009, Office Action.
U.S. Appl. No. 11/959,334, Jan. 12, 2010, Notice of Allowance.
U.S. Appl. No. 11/959,334, Apr. 14, 2010, Notice of Allowance.
U.S. Appl. No. 11/959,334, Jul. 23, 2010, Notice of Allowance.
U.S. Appl. No. 12/106,928, Jan. 23, 2009, Office Action.
U.S. Appl. No. 12/106,928, Oct. 5, 2009, Office Action.
U.S. Appl. No. 12/106,928, May 10, 2010, Office Action.
U.S. Appl. No. 12/106,928, Oct. 25, 2010, Office Action.
U.S. Appl. No. 12/106,928, Jun. 28, 2013, Office Action.
U.S. Appl. No. 12/106,928, Dec. 2, 2013, Office Action.
U.S. Appl. No. 12/106,928, Mar. 25, 2014, Advisory Action.
U.S. Appl. No. 12/106,937, Mar. 30, 2009, Office Action.
U.S. Appl. No. 12/106,937, Nov. 18, 2009, Office Action.
U.S. Appl. No. 12/106,937, Jun. 28, 2013, Office Action.
U.S. Appl. No. 12/106,937, Jan. 22, 2014, Office Action.
U.S. Appl. No. 12/113,851, Apr. 27, 2010, Office Action.
U.S. Appl. No. 12/113,851, Jun. 24, 2010, Office Action.
U.S. Appl. No. 12/113,851, Dec. 16, 2010, Office Action.
U.S. Appl. No. 12/113,851, Apr. 27, 2011, Office Action.
U.S. Appl. No. 12/113,851, Mar. 29, 2012, Office Action.
U.S. Appl. No. 12/113,851, Mar. 17, 2014, Office Action.
U.S. Appl. No. 12/114,031, Oct. 5, 2010, Office Action.
U.S. Appl. No. 12/114,031, Nov. 22, 2010, Office Action.
U.S. Appl. No. 12/114,031, May 11, 2011, Office Action.
U.S. Appl. No. 12/114,031, Aug. 2, 2011, Office Action.
U.S. Appl. No. 12/114,031, Mar. 6, 2012, Office Action.
U.S. Appl. No. 12/114,031, Mar. 10, 2014, Office Action.
U.S. Appl. No. 12/114,091, Oct. 27, 2010, Office Action.
U.S. Appl. No. 12/114,091, Dec. 17, 2010, Office Action.
U.S. Appl. No. 12/114,091, Jul. 7, 2011, Office Action.
U.S. Appl. No. 12/114,091, Apr. 5, 2012, Office Action.
U.S. Appl. No. 12/114,091, Nov. 8, 2012, Office Action.
U.S. Appl. No. 12/122,603, Mar. 3, 2011, Office Action.
U.S. Appl. No. 12/122,603, Apr. 22, 2011, Office Action.
U.S. Appl. No. 12/122,603, Sep. 23, 2011, Office Action.
U.S. Appl. No. 12/122,603, Nov. 20, 2013, Office Action.
U.S. Appl. No. 12/135,858, Jul. 13, 2011, Office Action.
U.S. Appl. No. 12/135,858, Feb. 16, 2012, Office Action.
U.S. Appl. No. 12/143,020, May 11, 2011, Office Action.
U.S. Appl. No. 12/143,020, Aug. 31, 2011, Office Action.
U.S. Appl. No. 12/143,020, Feb. 23, 2012, Notice of Allowance.
U.S. Appl. No. 12/338,977, Jan. 19, 2012, Office Action.
U.S. Appl. No. 12/338,977, Jul. 11, 2012, Office Action.
U.S. Appl. No. 12/338,977, Nov. 28, 2012, Office Action.
U.S. Appl. No. 12/338,977, Jun. 19, 2013, Office Action.
U.S. Appl. No. 12/393,877, Sep. 29, 2011, Office Action.
U.S. Appl. No. 12/393,877, Dec. 13, 2011, Office Action.
U.S. Appl. No. 12/393,877, May 21, 2012, Office Action.
U.S. Appl. No. 12/402,398, Mar. 9, 2010, Office Action.
U.S. Appl. No. 12/402,398, May 20, 2010, Office Action.
U.S. Appl. No. 12/402,398, Jan. 24, 2011, Office Action.
U.S. Appl. No. 12/402,398, Sep. 20, 2012, Office Action.
U.S. Appl. No. 12/402,398, Mar. 13, 2013, Notice of Allowance.
U.S. Appl. No. 12/403,256, Dec. 16, 2009, Office Action.
U.S. Appl. No. 12/403,256, Mar. 30, 2010, Office Action.
U.S. Appl. No. 12/403,256, Aug. 19, 2010, Notice of Allowance.
U.S. Appl. No. 12/403,277, Jul. 8, 2010, Office Action.
U.S. Appl. No. 12/403,277, Oct. 12, 2010, Office Action.
U.S. Appl. No. 12/403,277, Mar. 31, 2011, Office Action.
U.S. Appl. No. 12/403,277, Apr. 3, 2012, Office Action.
U.S. Appl. No. 12/403,277, Nov. 5, 2012, Office Action.
U.S. Appl. No. 12/403,277, Jan. 27, 2014, Office Action.
U.S. Appl. No. 12/481,377, Apr. 28, 2011, Office Action.
U.S. Appl. No. 12/481,377, Jun. 21, 2011, Office Action.
U.S. Appl. No. 12/481,377, Jan. 3, 2012, Office Action.
U.S. Appl. No. 12/481,377, Aug. 10, 2012, Notice of Allowance.
U.S. Appl. No. 12/548,274, Dec. 28, 2011, Office Action.
U.S. Appl. No. 12/548,274, Mar. 2, 2012, Office Action.
U.S. Appl. No. 12/548,274, Sep. 10, 2012, Office Action.
U.S. Appl. No. 12/608,769, Feb. 10, 2012, Office Action.

(56) References Cited

OTHER PUBLICATIONS

U.S. Appl. No. 12/608,769, Aug. 22, 2012, Office Action.
U.S. Appl. No. 12/608,769, Nov. 5, 2012, Notice of Allowance.
U.S. Appl. No. 12/608,773, Jun. 7, 2012, Office Action.
U.S. Appl. No. 12/608,773, Jul. 20, 2012, Office Action.
U.S. Appl. No. 12/608,773, Jan. 7, 2013, Office Action.
U.S. Appl. No. 12/642,319, Feb. 27, 2012, Office Action.
U.S. Appl. No. 12/642,319, Aug. 28, 2012, Office Action.
U.S. Appl. No. 12/642,319, Dec. 16, 2013, Office Action.
U.S. Appl. No. 12/684,400, Feb. 13, 2012, Office Action.
U.S. Appl. No. 12/684,400, May 9, 2012, Office Action.
U.S. Appl. No. 12/684,400, Oct. 16, 2012, Office Action.
U.S. Appl. No. 12/684,470, Dec. 20, 2011, Office Action.
U.S. Appl. No. 12/684,470, Mar. 23, 2012, Office Action.
U.S. Appl. No. 12/684,470, Aug. 30, 2012, Office Action.
U.S. Appl. No. 12/684,542, Jan. 30, 2012, Office Action.
U.S. Appl. No. 12/684,542, Apr. 16, 2012, Office Action.
U.S. Appl. No. 12/684,542, Sep. 13, 2012, Office Action.
U.S. Appl. No. 12/684,562, Dec. 28, 2011, Office Action.
U.S. Appl. No. 12/684,562, Feb. 16, 2012, Office Action.
U.S. Appl. No. 12/684,562, Aug. 21, 2012, Office Action.
U.S. Appl. No. 12/684,569, Dec. 20, 2011, Office Action.
U.S. Appl. No. 12/684,569, Jan. 27, 2012, Office Action.
U.S. Appl. No. 12/684,569, Jul. 30, 2012, Office Action.
U.S. Appl. No. 12/688,065, Mar. 13, 2012, Office Action.
U.S. Appl. No. 12/688,065, Apr. 26, 2012, Office Action.
U.S. Appl. No. 12/688,065, Oct. 12, 2012, Office Action.
U.S. Appl. No. 12/688,065, Oct. 18, 2013, Office Action.
U.S. Appl. No. 12/688,065, Apr. 8, 2014, Office Action.
U.S. Appl. No. 12/724,304, Feb. 10, 2012, Office Action.
U.S. Appl. No. 12/848,642, Sep. 20, 2012, Office Action.
U.S. Appl. No. 12/848,642, Nov. 9, 2012, Office Action.
U.S. Appl. No. 12/848,642, Apr. 26, 2013, Office Action.
U.S. Appl. No. 12/848,642, Feb. 3, 2014, Notice of Allowance.
U.S. Appl. No. 12/850,242, Aug. 6, 2012, Office Action.
U.S. Appl. No. 12/850,242, Oct. 17, 2012, Office Action.
U.S. Appl. No. 12/850,242, Apr. 18, 2013, Office Action.
U.S. Appl. No. 12/850,242, Aug. 6, 2013, Notice of Allowance.
U.S. Appl. No. 12/897,358, Aug. 22, 2011, Office Action.
U.S. Appl. No. 12/897,358, Jan. 12, 2012, Notice of Allowance.
U.S. Appl. No. 12/897,358, Mar. 5, 2012, Notice of Allowance.
U.S. Appl. No. 12/941,809, Dec. 13, 2011, Office Action.
U.S. Appl. No. 12/941,809, Jan. 30, 2012, Office Action.
U.S. Appl. No. 12/941,809, Jun. 1, 2012, Office Action.
U.S. Appl. No. 12/941,809, Jul. 3, 2013, Office Action.
U.S. Appl. No. 12/941,809, Nov. 8, 2013, Office Action.
U.S. Appl. No. 12/941,809, Feb. 3, 2014, Notice of Allowance.
U.S. Appl. No. 12/945,646, Jan. 20, 2011, Office Action.
U.S. Appl. No. 12/945,646, Jul. 6, 2011, Office Action.
U.S. Appl. No. 12/945,646, Oct. 26, 2011, Office Action.
U.S. Appl. No. 12/945,646, Feb. 21, 2012, Notice of Allowance.
U.S. Appl. No. 12/955,859, May 26, 2011, Office Action.
U.S. Appl. No. 12/955,859, Jul. 21, 2011, Office Action.
U.S. Appl. No. 12/955,859, Dec. 15, 2011, Office Action.
U.S. Appl. No. 12/955,859, Aug. 6, 2012, Office Action.
U.S. Appl. No. 12/955,859, May 16, 2013, Office Action.
U.S. Appl. No. 12/955,859, Aug. 1, 2013, Notice of Allowance.
U.S. Appl. No. 12/961,331, Dec. 4, 2012, Office Action.
U.S. Appl. No. 12/961,331, Feb. 1, 2013, Office Action.
U.S. Appl. No. 12/961,331, Jul. 3, 2013, Office Action.
U.S. Appl. No. 12/961,331, Sep. 20, 2013, Advisory Action.
U.S. Appl. No. 12/966,923, Feb. 3, 2012, Notice of Allowance.
U.S. Appl. No. 12/973,204, Mar. 7, 2012, Notice of Allowance.
U.S. Appl. No. 12/987,792, Mar. 13, 2012, Office Action.
U.S. Appl. No. 12/987,792, Sep. 17, 2012, Office Action.
U.S. Appl. No. 12/987,792, Jan. 21, 2014, Office Action.
U.S. Appl. No. 13/026,989, Sep. 16, 2011, Office Action.
U.S. Appl. No. 13/026,989, Jun. 8, 2012, Office Action.
U.S. Appl. No. 13/026,989, Aug. 23, 2013, Office Action.
U.S. Appl. No. 13/030,922, Dec. 18, 2012, Office Action.
U.S. Appl. No. 13/030,922, Jan. 31, 2013, Office Action.
U.S. Appl. No. 13/030,922, Jul. 18, 2013, Office Action.
U.S. Appl. No. 13/030,922, Jan. 8, 2014, Notice of Allowance.
U.S. Appl. No. 13/039,087, Jul. 17, 2012, Office Action.
U.S. Appl. No. 13/039,087, Nov. 6, 2012, Notice of Allowance.
U.S. Appl. No. 13/112,618, Mar. 29, 2013, Office Action.
U.S. Appl. No. 13/112,618, Jun. 7, 2013, Office Action.
U.S. Appl. No. 13/112,618, Nov. 20, 2013, Office Action.
U.S. Appl. No. 13/112,631, Mar. 29, 2013, Office Action.
U.S. Appl. No. 13/112,631, Jun. 26, 2013, Office Action.
U.S. Appl. No. 13/112,631, Dec. 2, 2013, Office Action.
U.S. Appl. No. 13/153,594, Jan. 29, 2013, Office Action.
U.S. Appl. No. 13/153,594, May 29, 2013, Office Action.
U.S. Appl. No. 13/153,594, Oct. 16, 2013, Notice of Allowance.
U.S. Appl. No. 13/222,899, Jan. 10, 2014, Office Action.
U.S. Appl. No. 13/308,227, Apr. 10, 2013, Office Action.
U.S. Appl. No. 13/308,227, Sep. 11, 2013, Office Action.
U.S. Appl. No. 13/488,233, Feb. 5, 2013, Notice of Allowance.
U.S. Appl. No. 13/490,143, Jan. 4, 2013, Office Action.
U.S. Appl. No. 13/490,143, Apr. 29, 2013, Notice of Allowance.
U.S. Appl. No. 13/525,839, Apr. 1, 2013, Office Action.
U.S. Appl. No. 13/525,839, Jul. 15, 2013, Notice of Allowance.
U.S. Appl. No. 13/615,547, Jan. 18, 2013, Office Action.
U.S. Appl. No. 13/615,547, Apr. 12, 2013, Notice of Allowance.
U.S. Appl. No. 13/791,829, May 29, 2013, Office Action.
U.S. Appl. No. 13/791,829, Oct. 8, 2013, Notice of Allowance.
U.S. Appl. No. 13/898,202, Jan. 3, 2014, Office Action.
U.S. Appl. No. 29/296,370, Aug. 18, 2008, Office Action.
U.S. Appl. No. 29/296,370, Dec. 2, 2008, Notice of Allowance.
U.S. Appl. No. 29/296,370, Apr. 1, 2009, Notice of Allowance.
U.S. Appl. No. 14/839,658, filed Aug. 31, 2015, Cummins et al.
U.S. Appl. No. 14/855,080, filed Sep. 15, 2015, Voss et al.
U.S. Appl. No. 12/122,603, Sep. 23, 2015, Notice of Allowance.
U.S. Appl. No. 12/608,773, Sep. 17, 2015, Notice of Allowance.
U.S. Appl. No. 12/684,400, Jul. 28, 2015, Notice of Allowance.
U.S. Appl. No. 12/684,470, Aug. 26, 2015, Office Action.
U.S. Appl. No. 13/222,899, Aug. 5, 2015, Office Action.
U.S. Appl. No. 13/791,846, Oct. 27, 2015, Notice of Allowance.
U.S. Appl. No. 14/017,039, filed Oct. 27, 2015, Office Action.
U.S. Appl. No. 14/246,926, Aug. 5, 2015, Office Acion.
U.S. Appl. No. 11/396,731, Feb. 12, 2015, Office Action.
U.S. Appl. No. 11/396,731, Jul. 9, 2015, Notice of Allowance.
U.S. Appl. No. 11/455,993, Aug. 11, 2014, Notice of Allowance.
U.S. Appl. No. 11/532,325, Jan. 16, 2015, Notice of Allowance.
U.S. Appl. No. 11/532,325, Jul. 8, 2015, Issue Notification.
U.S. Appl. No. 11/958,295, Jun. 13, 2014, Notice of Allowance.
U.S. Appl. No. 12/106,928, Oct. 3, 2014, Notice of Allowance.
U.S. Appl. No. 12/106,937, Mar. 5, 2015, Notice of Allowance.
U.S. Appl. No. 12/113,851, Aug. 21, 2014, Office Action.
U.S. Appl. No. 12/113,851, Feb. 20, 2015, Notice of Allowance.
U.S. Appl. No. 12/114,091, Feb. 12, 2015, Office Action.
U.S. Appl. No. 12/114,091, Jul. 23, 2015, Office Action.
U.S. Appl. No. 12/122,603, Apr. 30, 2014, Office Action.
U.S. Appl. No. 12/122,603, Apr. 9, 2015, Office Action.
U.S. Appl. No. 12/393,877, Aug. 4, 2014, Notice of Allowance.
U.S. Appl. No. 12/403,277, Aug. 15, 2014, Office Action.
U.S. Appl. No. 12/548,274, Aug. 14, 2014, Office Action.
U.S. Appl. No. 12/608,773, Jul. 17, 2014, Office Action.
U.S. Appl. No. 12/608,773, Mar. 12, 2015, Office Action.
U.S. Appl. No. 12/642,319, May 27, 2014, Notice of Allowance.
U.S. Appl. No. 12/684,400, Feb. 23, 2015, Office Action.
U.S. Appl. No. 12/684,470, Jun. 4, 2014, Office Action.
U.S. Appl. No. 12/684,470, Nov. 14, 2014, Office Action.
U.S. Appl. No. 12/684,542, Jun. 18, 2014, Office Action.
U.S. Appl. No. 12/684,542, Dec. 1, 2014, Office Action.
U.S. Appl. No. 12/684,562, Sep. 10, 2014, Office Action.
U.S. Appl. No. 12/684,562, Feb. 17, 2015, Notice of Allowance.
U.S. Appl. No. 12/684,562, Jul. 8, 2015, Issue Notification.
U.S. Appl. No. 12/684,569, Apr. 23, 2014, Office Action.
U.S. Appl. No. 12/950,628, Apr. 25, 2014, Notice of Allowance.
U.S. Appl. No. 12/961,331, Apr. 25, 2014, Notice of Allowance.
U.S. Appl. No. 12/987,792, Jun. 11, 2014, Office Action.
U.S. Appl. No. 12/987,792, Aug. 25, 2014, Notice of Allowance.

(56) References Cited

OTHER PUBLICATIONS

U.S. Appl. No. 13/112,618, Dec. 15, 2014, Office Action.
U.S. Appl. No. 13/112,618, May 18, 2015, Office Action.
U.S. Appl. No. 13/112,631, Nov. 20, 2014, Office Action.
U.S. Appl. No. 13/112,631, Apr. 15, 2015, Office Action.
U.S. Appl. No. 13/222,899, Jul. 31, 2014, Office Action.
U.S. Appl. No. 13/222,899, Apr. 1, 2015, Office Action.
U.S. Appl. No. 13/308,227, Jul. 14, 2015, Office Action.
U.S. Appl. No. 13/791,846, Jun. 4, 2015, Office Action.
U.S. Appl. No. 13/898,202, Aug. 21, 2014, Office Action.
U.S. Appl. No. 13/898,202, Feb. 10, 2015, Notice of Allowance.
U.S. Appl. No. 13/908,796, Jul. 21, 2015, Office Action.
U.S. Appl. No. 14/017,039, Jan. 23, 2015, Office Action.
U.S. Appl. No. 14/017,039, Jun. 10, 2015, Office Action.
U.S. Appl. No. 14/023,428, Jul. 27, 2015, Office Action.
U.S. Appl. No. 14/077,007, Jul. 27, 2015, Office Action.
U.S. Appl. No. 14/466,576, Jul. 8, 2015, Office Action.
U.S. Appl. No. 13/908,796, Nov. 6, 2015, Notice of Allowance.
U.S. Appl. No. 14/323,753, Nov. 3, 2015, Office Action.
U.S. Appl. No. 14/928,950, filed Oct. 30, 2015, Voss.
U.S. Appl. No. 15/056,281, filed Feb. 29, 2016, Palermo et al.
U.S. Appl. No. 15/069,230, filed Mar. 14, 2016, Kokish.
Carpenter et al, Midterm results of the multicenter trial of the Powerlink bifurcated system for endovascular aortic aneurysm repair, Journal of Vascular Surgery, vol. 40, No. 5, Nov. 2004, p. 849-859.e5.
Eisenack et al, Percutaneous Endovascular Aortic Aneurysm Repair: A Prospective Evaluation of Safety, Efficiency, and Risk Factors, Journal of Endovascular Ther., 2009, vol. 16, p. 708-713.
Greenhalgh et al, Endovascular versus open repair of abdominal aortic aneurysm, The New England journal of medicine, vol. 362, No. 20, 2010, p. 1863-1871.
Grossman, W., Cardiac Catheterization and Angiography, 3rd Ed., Lea & Febiger, Philadelphia, pp. 1-49, 52-247. 1986.
Howell et al, Percutaneous Repair of Abdominal Aortic Aneurysms Using the aneuRx Stent Graft and the Percutaneous Vascular Surgery Device, Catheterization and cardiovascular interventions, vol. 55, No. 3, 2002, p. 281-287.
Jean-Baptiste et al., Percutaneous closure devices for endovascular repair of infrarenal abdominal aortic aneurysms: a prospective, non-randomized comparative study, European Journal of Vascular and Endovascular Surgery, vol. 35, No. 4, 2008, p. 422-428.
Krajcer and Gregoric, Totally percutaneous aortic aneurysm repair: methods and outcomes using the fully integrated IntuiTrak endovascular system, The Journal of cardiovascular surgery, vol. 51, No. 4, 2010, p. 493-501.
Lederle et al, Outcomes following endovascular vs open repair of abdominal aortic aneurysm: a randomized trial, Jama, vol. 302, No. 14, 2009, p. 1535-1542.
Lee et al, Total percutaneous access for endovascular aortic aneurysm repair ("Preclose" technique), Journal of vascular surgery, vol. 45, No. 6, 2007, p. 1095-1101.
Malkawi et al, Percutaneous access for endovascular aneurysm repair: a systematic review, European Journal of Vascular and Endovascular Surgery, vol. 39, No. 6, 2010, p. 676-682.
Morasch et al, Percutaneous repair of abdominal aortic aneurysm, Journal of vascular surgery, vol. 40, No. 1, 2004, p. 12-16.
Rachel et al, Percutaneous endovascular abdominal aortic aneurysm repair, Annals of vascular surgery, vol. 16, No. 1, 2002, p. 43-49.
Starnes et al, Totally percutaneous aortic aneurysm repair: experience and prudence, Journal of vascuiar surgery, vol. 43, No. 2, 2006, p. 270-276.
Teh et al, Use of the percutaneous vascular surgery device for closure of femoral access sites during endovascular aneurysm repair: lessons from our experience, European Journal of Vascular and Endovascular Surgery, vol. 22, No. 5, 2001, p. 418-423.
Torsello et al, Endovascular sutureversus cutdown for endovascular aneurysm repair. A prospective randomized pilot study, Journal of vascular surgery, vol. 38, No. 1, 2003, p. 78-82.
Traul et al, Percutaneous endovascular repair of infrarenal abdominal aortic aneurysms: a feasibility study, Journal of vascular surgery, vol. 32, No, 4, 2000, p. 770-776.
Watelet et al, Percutaneous repair of aortic aneurysms: a prospective study of suture-mediated closure devices, European journal of vascular and endovascular surgery, vol. 32, No. 3, 2006, p. 261-265.
U.S. Appl. No. 12/684,470, Jan. 21, 2016, Office Action.
U.S. Appl. No. 13/112,618, Jan. 29, 2016, Office Action.
U.S. Appl. No. 13/222,899, Jan. 7, 2016, Notice of Allowance.
U.S. Appl. No. 13/308,227, Feb. 1, 2016, Notice of Allowance.
U.S. Appl. No. 13/725,589, Sep. 17, 2015, Office Action.
U.S. Appl. No. 13/725,589, Mar. 18, 2016, Notice of Allowance.
U.S. Appl. No. 13/837,801, Dec. 16, 2015, Office Action.
U.S. Appl. No. 13/908,796, Mar. 9, 2016, Issue Notification.
U.S. Appl. No. 14/023,428, Feb. 9, 2016, Office Action.
U.S. Appl. No. 14/077,007, Jan. 29, 2016, Office Action.
U.S. Appl. No. 14/246,926, Nov. 23, 2015, Office Action.
U.S. Appl. No. 14/312,339, Jan. 22, 2016, Office Action.
U.S. Appl. No. 14/466,576, Dec. 15, 2015, Notice of Allowance.
U.S. Appl. No. 14/539,830, Jan. 29, 2016, Office Action.
U.S. Appl. No. 15/131,786, filed Apr. 18, 2016, Roorda et al.
U.S. Appl. No. 15/149,784, filed May 9, 2016, Yribarren.
U.S. Appl. No. 13/112,618, Jul. 6, 2016, Notice of Allowance.
U.S. Appl. No. 14/077,007, Aug. 12, 2016, Notice of Allowance.
U.S. Appl. No. 14/246,926, Oct. 3, 2016, Notice of Allowance.
U.S. Appl. No. 14/539,830, Jul. 26, 2016, Office Action.
U.S. Appl. No. 15/005,780, filed Jan. 25, 2016, Mehl.
U.S. Appl. No. 15/142,106, filed Apr. 29, 2016, Voss.
U.S. Appl. No. 12/114,091, Apr. 6, 2016, Notice of Allowance.
U.S. Appl. No. 12/684,470, Apr. 22, 2016, Notice of Allowance.
U.S. Appl. No. 13/837,801, Jun. 9, 2016, Office Action.
U.S. Appl. No. 14/017,039, Apr. 4, 2016, Notice of Allowance.
U.S. Appl. No. 14/023,428, Jun. 13, 2016, Office Action.
U.S. Appl. No. 14/246,926, Jun. 15, 2016, Office Action.
U.S. Appl. No. 14/312,339, May 3, 2016, Office Action.
U.S. Appl. No. 14/323,753, Apr. 15, 2016, Notice of Allowance.

* cited by examiner

CLOSURE DEVICE AND METHODS FOR MAKING AND USING THEM

CROSS-REFERENCE TO RELATED APPLICATIONS

This a continuation application of U.S. patnent application Ser. No. 11/396,141, filed 31 Mar. 2006, now U.S. Pat. No. 8,690,910, which is (i) a continuation-in-part application of U.S. patent application Ser. No. 10/787,073, filed Feb. 24, 2004, now U.S. Pat. No. 7,806,904, which is a continuation-in-part application of U.S. patent application Ser. No. 10/435,104, filed May 9, 2003, now U.S. Pat. No. 7,879,071, which is a divisional application of U.S. patent application Ser. No. 10/081,726, filed Feb. 21, 2002, now U.S. Pat. No. 6,623,510, which is a continuation-in-part application of U.S. patent application Ser. No. 09/732,178, filed Dec. 7, 2000, now U.S. Pat. No. 6,719,777, and (ii) is also a continuation-in-part application of U.S. patent application Ser. No. 10/335,075, filed Dec. 31, 2002, now U.S. Pat. No. 7,211,101, which is a continuation-in-part application of U.S. patent application Ser. No. 10/081,726, filed Feb. 21, 2002, now U.S. Pat. No. 6,623,510, which is a continuation-in-part application of U.S. patent application Ser. No. 09/732,178, filed Dec. 7, 2000, now U.S. Pat. No. 6,719,777, each of the disclosures of which, and any references therein, are incorporated herein in their entirety by this reference.

This continuation application also relates to U.S. application Ser. No. 09/732,178, filed Dec. 7, 2000, now U.S. Pat. No. 6,719,777; Ser. No. 10/081,726, filed Feb. 21, 2002, now U.S. Pat. No. 6,623,510; Ser. No. 10/335,075, filed Dec. 31, 2002; Ser. No. 10/081,723, filed Feb. 21, 2002, now U.S. Pat. No. 6,942,674; Ser. No. 10/081,717, filed Feb. 21, 2002; Ser. No. 10/356,214, filed Jan. 30, 2003 and Ser. No. 10/638,115, filed Aug. 8, 2003, the disclosures of which, and any references therein, are incorporated herein in their entirety by this reference.

BACKGROUND OF THE INVENTION

1. The Field of the Invention

The present invention relates generally to apparatus and methods for engaging tissue and/or closing openings through tissue, and more particularly to devices for closing a puncture in a blood vessel or other body lumen formed during a diagnostic or therapeutic procedure, and to methods for making and using such devices.

2. The Relevant Technology

Catheterization and interventional procedures, such as angioplasty or stenting, generally are performed by inserting a hollow needle through a patient's skin and intervening tissue into the vascular system. A guide wire may then be passed through the needle lumen into the patient's blood vessel accessed by the needle. The needle may be removed, and an introducer sheath may be advanced over the guide wire into the vessel, e.g., in conjunction with or subsequent to a dilator. A catheter or other device may then be advanced through a lumen of the introducer sheath and over the guide wire into a position for performing a medical procedure. Thus, the introducer sheath may facilitate introduction of various devices into the vessel, while minimizing trauma to the vessel wall and/or minimizing blood loss during a procedure.

Upon completion of the procedure, the devices and introducer sheath may be removed, leaving a puncture site in the vessel wall. External pressure may be applied to the puncture site until clotting and wound sealing occur. This procedure, however, may be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. When deployed, the plug may seal the vessel and provide hemostasis. Such devices, however, may be difficult to position properly with respect to the vessel, which may be particularly significant since it is generally undesirable to expose the plug material, e.g., collagen, within the bloodstream, where it may float downstream and risk causing an embolism.

Another technique has been suggested that involves percutaneously suturing the puncture site, such as that disclosed in U.S. Pat. No. 5,304,184, issued to Hathaway et al. Percutaneous suturing devices, however, may require significant skill by the user, and may be mechanically complex and expensive to manufacture.

U.S. Pat. No. 5,478,354, issued to Tovey et al., discloses a surgical fastener including an annular base having legs that, in a relaxed state, extend in a direction substantially perpendicular to a plane defined by the base and slightly inwards toward one another. During use, the fastener is fit around the outside of a cannula, thereby deflecting the legs outward. The cannula is placed in an incision, and the fastener is slid along the cannula until the legs pierce into skin tissue. When the cannula is withdrawn, the legs move towards one another back to the relaxed state to close the incision.

U.S. Pat. Nos. 5,007,921 and 5,026,390, issued to Brown, disclose staples that may be used to close a wound or incision. In one embodiment, an "S" shaped staple is disclosed that includes barbs that may be engaged into tissue on either side of the wound. In another embodiment, a ring-shaped staple is disclosed that includes barbs that project from the ring. Sides of the ring may be squeezed to separate the barbs further, and the barbs may be engaged into tissue on either side of a wound. The sides may then be released, causing the barbs to return closer together, and thereby pulling the tissue closed over the wound. These staples, however, have a large cross-sectional profile and therefore may not be easy to deliver through a percutaneous site to close an opening in a vessel wall.

Accordingly, devices for engaging tissue, e.g., to close a vascular puncture site, would be considered useful.

BRIEF SUMMARY OF THE INVENTION

The present invention is directed to devices and methods for engaging tissue, e.g., to connect tissue segments together or to close and/or seal openings through tissue, such as in a wall of a body lumen. More particularly, the present invention is directed to vascular closure devices or clips for closing a puncture in a wall of a blood vessel formed during a diagnostic or therapeutic procedure, and to methods for making and using such devices.

In accordance with one aspect of the present invention, a device for closing an opening in a body lumen is provided that includes a generally annular-shaped body defining a plane, and a plurality of tissue engaging portions extending from the annular-shaped body substantially transversely with respect to the plane. In this embodiment, opposing tissue engaging portions, e.g., tines, are biased towards a substantially planar configuration lying in the plane. In one embodiment, the tissue engaging portions are biased towards one another, e.g., to close a puncture site or other opening through tissue. Alternatively, the tissue engaging portions may be biased away from one another.

In accordance with one aspect, the tissue engaging portions are integrally formed with the annular-shaped body, e.g., from a sheet of material, such as Nitinol or other superelastic alloy. The tissue engaging portions may be formed with the sheet of material in the substantially planar configuration. The tissue engaging portions may be deflected substantially transversely with respect to the plane to define a substantially transverse configuration. Alternatively, the device may be formed from an elongate wire or tube that may be wound to form an enclosed body.

In accordance with another aspect, the tissue engaging portions, e.g., tines, optionally including barbs, for penetrating tissue, may be disposed substantially symmetrically about a central axis. Alternatively, the tissue engaging portions may be disposed in opposing sets along a linear axis.

In accordance with another aspect of the present invention, a device for engaging tissue, e.g., to close an opening in a body lumen, is provided that includes a generally annular-shaped body defining a plane. A plurality of tissue engaging portions extend from the annular-shaped body substantially transversely with respect to the plane. In one embodiment, opposing tissue engaging portions of the device are biased towards a substantially planar configuration lying in the plane, as described above.

One or more expandable elements are disposed along a periphery of the annular-shaped body. The expandable elements are expandable between expanded and compressed states for increasing and reducing a peripheral dimension of the annular-shaped body, respectively. In one embodiment, the expandable elements may be an enclosed cell, e.g. a diamond-shaped cell, having a first width in the expanded state and a second width in the compressed state that is smaller than the first width. Alternatively, the expandable elements may be a zig-zag element or an arcuate element. The expandable elements can be biased to the expanded state, e.g., by appropriate heat treating of the expandable elements. Alternatively, the expandable elements may be biased to the compressed state.

In accordance with yet another aspect of the present invention, a clip, such as those described above, may be loaded on a delivery apparatus and used to close and/or seal an opening in a wall of a body lumen. The apparatus generally includes a sheath including proximal and distal ends defining a longitudinal axis there between. A housing is slidably disposed on the sheath, the housing including an annular cavity therein. A clip, such as those described above, is disposed within the cavity with the tissue engaging portions disposed substantially distally.

The housing can be actuable for advancing the clip distally towards the distal end of the sheath, e.g., to deploy the clip from the cavity. For example, the apparatus may include an actuator coupled to the housing, the actuator configured for advancing the housing distally to deploy the clip. The actuator includes a spring mechanism for biasing the housing distally upon activation of the actuator. In addition, the apparatus may include a locator element for positioning the distal end of the sheath, such as a bleed back lumen or a mechanical locator.

During use, the distal end of the sheath, with the housing and clip near its proximal end, may be positioned through a patient's skin along a passage and into a body lumen via an opening in the wall of the body lumen. One or more instruments may be introduced through the lumen of the sheath into the body lumen. A diagnostic or therapeutic procedure may be performed using the instruments at a location accessed via the body lumen. For example, the body lumen is a peripheral blood vessel, such as a femoral artery, and the procedure may include angioplasty, atherectomy, stent delivery, delivery of a therapeutic agent, and/or tissue ablation.

The sheath may be manipulated, for example, with the aid of a locator element, to position the distal end with respect to the opening, e.g., to ensure that the clip engages a wall of the body lumen or other tissue proximal to the opening and is not advanced into the body lumen itself. The housing is advanced distally into the passage, e.g., until the tissue engaging portions of the clip substantially engage the wall of the body lumen or other tissue proximal to the opening in the wall of the body lumen. In addition, or alternatively, the clip may be deployed from the housing, for example, by an ejector within the housing. The sheath may then be withdrawn from the body lumen and passage, leaving the clip in the passage. As the distal end of the sheath is withdrawn through the clip, the tissue engaging portions automatically at least partially move towards the planar configuration to pull the engaged tissue together and substantially close the opening.

In one embodiment, the clip automatically expands to an enlarged cross-section when the clip is deployed from the housing. Thus, the clip may be compressed to facilitate loading into the housing, and thereby provide a reduced profile for the clip. This may be useful to allow the clip to be delivered through a smaller puncture.

A method according to the present invention may include causing a clip or other closure element to engage tissue, e.g., muscle, fat, fascia, and the like, that is proximal to the body lumen. Thus, unlike previously known methods, which are directed to closing the wall of a blood vessel using clips or sutures, the present invention may include deploying a closure element in the passage to cause it to engage intermediate tissue between the patient's skin and the wall of the body lumen. When performed in this manner, the need to precisely position a closure element may be avoided as is required when engaging the wall of a vessel. Instead, the closure element may be located and delivered at a range of locations along the length of the passage yet still close and/or seal the passage. In effect, extra-vascular tissue is engaged to close the passage and thereby cause sealing of the wound. When the closure element is deployed, it can be planar, e.g., extending substantially parallel to the surface of the patient's skin, although not necessarily so.

In one aspect of the present invention, a device for engaging tissue includes a generally annular-shaped body defining a plane and disposed about a central axis extending substantially normal to the plane. The body may be movable from a substantially planar configuration lying generally in the plane towards a transverse configuration extending out of the plane. The body may also include a plurality of looped elements including alternating first and second curved regions that define an inner and outer periphery of the body, respectively, in the planar configuration. A plurality of tines or other tissue-engaging elements may extend from the first curved regions, and may be oriented towards the central axis in the planar configuration, and substantially parallel to the central axis in the transverse configuration. The device may be biased towards the planar configuration, e.g., to bias the tines towards the central axis.

The looped elements of the device may generally define an endless zigzag pattern, e.g., a sinusoidal pattern, extending about the central axis. The looped elements may facilitating deforming the device between the planar and transverse configurations, e.g., by distributing stresses through the device and minimizing localized stresses in the curved regions. In addition, the looped elements may be expandable between expanded and compressed states for increasing and reducing a periphery of the body in the transverse orientation, respectively. The looped elements may be biased towards one of the compressed and expanded states.

Adjacent tines of the device may have a first curved region disposed between them. The first curved region between adjacent tines may include a substantially blunt element extending towards the central axis. The blunt element may have a length shorter than lengths of the adjacent tines.

In addition or alternatively, the tines of the device may include first and second primary tines, having a first length and a second length, respectively, which may be the same as or different than one another. The first and second primary tines may be disposed on opposing first curved regions, and may be oriented substantially towards each other in the planar configuration. In the planar configuration, the first and second primary tines may at least partially overlap. The tines may also include one or more secondary tines having a length substantially shorter than the first and second lengths of the primary tines. The secondary tines may be disposed on either side of the first and second primary tines.

In another aspect of the present invention, a device for engaging tissue includes a generally annular-shaped body defining a plane and disposed about a central axis extending substantially normal to the plane. The body may be movable from a substantially planar configuration lying generally in the plane towards a transverse configuration extending out of the plane. A first primary tine, having a first length, may extend from the body towards the central axis in the planar configuration, and may be deflectable out of the plane when the body is moved towards the transverse configuration. A second primary tine, having a second length, may extend from the body towards the first tine when the body is in the planar configuration, and may be deflectable out of the plane when the body is moved towards the transverse configuration. The lengths of the first and second primary tines may cause the primary tines to at least partially overlap in the planar configuration. The body may be biased towards the planar configuration to bias the tines generally towards the central axis.

The device may include a set of secondary tines having a length shorter than the first and second lengths. The secondary tines may extend from the body towards the central axis in the planar configuration, and may be deflectable out of the plane when the body is moved towards the transverse configuration. In an exemplary embodiment, a secondary tine may be disposed on either side of the first primary tine, and a secondary tine may be disposed on either side of the second primary tine.

Optionally, adjacent tines may have a first curved region disposed between them. The first curved region between adjacent tines may include a substantially blunt element extending towards the central axis. The blunt element may have a length shorter than lengths of the adjacent tines.

Also, the device may include a plurality of looped elements disposed around a periphery of the body. The looped elements may generally define an endless zigzag pattern extending about the central axis. The first primary tine and the second primary tine may extend from looped elements disposed opposite one another. The looped elements may be expandable between expanded and compressed states for increasing and reducing a periphery of the body in the transverse orientation, respectively. The looped elements may be biased towards one of the compressed and expanded states.

In another aspect of the present invention, a method is provided for manufacturing a clip from an elastic material, such as a sheet of superelastic alloy, e.g., a nickel-titanium alloy ("Nitinol"). The components of the clip, e.g., a generally-annular body, optionally including looped elements, and/or tines, may be formed by removing portions from the sheet. The portions may be removed, e.g., by laser cutting, chemical etching, photo chemical etching, stamping, electrical discharge machining, and the like. The clip may be polished using one or more processes, such as electropolishing, chemical etching, tumbling, sandblasting, sanding, and the like, and/or heat-treated to provide a desired finish and/or desired mechanical properties. Optionally, the body and tines may be coated with a therapeutic agent, e.g., a peptide coating and/or one or more clotting factors.

In addition or alternatively, the clip may be disposed in a planar configuration, e.g., upon forming the clip from the sheet, and heat treated to form a clip biased to the planar configuration. For example, the clip may be formed from a shape memory material, e.g., Nitinol, which may substantially recover the planar configuration when heated to a first predetermined temperature corresponding to an austenitic state, e.g., a temperature close to body temperature. The clip may be cooled to a second predetermined temperature corresponding to a martensitic state, e.g., a temperature at or below ambient temperature, and malleably manipulated. For example, the clip formed from the sheet may be deformed to a transverse configuration, such as that described above, e.g., by loading the clip onto a mandrel or directly onto a delivery device. If the clip includes looped elements formed from the body, the looped elements may be biased upon heat treatment towards an expanded state, but may be malleably deformed to a compressed state upon cooling, e.g., to facilitate loading onto the delivery device. Alternatively, the clip may be formed from a superelastic material, e.g., Nitinol, such that the clip may be resiliently deformed to the transverse configuration and/or compressed state, yet may automatically attempt to resume its planar configuration and/or expanded state upon release from external forces.

In still another aspect of the present invention, a method for closing an opening in a wall of a body lumen is provided. The distal end of an elongate member may be advanced through an opening in a patient's skin, along a passage through tissue, and into the body lumen. A distal portion of an obturator may be positioned distally beyond the distal end of the elongate member along the passage within the body lumen. One or more expandable elements on the distal portion of the obturator may be expanded transversely. The obturator may be withdrawn from the passage until the expandable elements contact the wall of the body lumen, thereby providing a tactile indication of a location of the wall of the body lumen between the elongate member and the plurality of expandable elements of the obturator.

A clip may be advanced into the passage over the elongate member until tines of the clip penetrate the wall of the body lumen, the tines and the expandable elements on the obturator being angularly offset from one another such that the tines penetrate the wall at locations between the expandable elements. The obturator may be collapsed, and the elongate member and/or obturator may be withdrawn from the body lumen and passage, leaving the clip to substantially close the opening in the wall of the body lumen. When the elongate member is withdrawn, the tines may automatically at least partially move towards a planar configuration to substantially close the opening.

The tines of the clip may include primary tines and secondary tines. Here, advancing the clip may include puncturing the wall of the body lumen with the primary tines until tips of the primary tines enter the body lumen, and puncturing the wall of the body lumen with the secondary tines. The primary tines and the secondary tines may puncture the walls without contacting the expandable elements of the obturator.

The present invention is also directed to methods for manufacturing tissue engaging clips in a manner in which a clip-precursor is first formed and such precursor is then reconfigured into the final shape of the clip. In one embodiment of the invention, a clip having an annular or hoop-shaped generally planar configuration with radially inwardly extending tines is manufactured by first forming a precursor with the tines extending radially outward and then reconfigured by inserting the precursor to its final shape with the tines extending radially inward and then heat setting the clip in this configuration. This permits the tines to be packed more closely together which enhances the sealing function of the clip and reduces the size of the clip's footprint. As will be explained in more detail herein, this manufacturing method overcomes the limitations of conventional methods in which the clip is manufactured in its final configuration.

In another embodiment, an annular or hoop-shaped planar clip precursor with radially inwardly extending tines is first manufactured in an oversize configuration and then has its lateral dimensions reduced to pack the tines closer together and to reduce the footprint of the clip and then heat set in that configuration.

The present invention is directed to vascular closure devices or clips having a design particularly suitable for closing a puncture in a wall of a blood vessel formed during a diagnostic or therapeutic procedure. According to the present invention, a device for engaging tissue includes a generally annular-shaped body defining a plane and disposed about a central axis extending substantially normal to the plane. The body may be movable from a substantially planar configuration lying generally in the plane towards a transverse configuration extending out of the plane. The body also includes a plurality of looped elements including alternating first and second curved regions that define an inner and outer periphery of the body, respectively, in the planar configuration. A plurality of tines or other tissue-engaging elements extend from the first curved regions, and are oriented towards the central axis in the planar configuration, and substantially parallel to the central axis in the transverse configuration. The device may be biased towards the planar configuration, e.g., to bias the tines towards the central axis.

The looped elements of the device may generally define an endless zigzag pattern, e.g., a sinusoidal pattern, extending about the central axis. The looped elements may facilitating deforming the device between the planar and transverse configurations, e.g., by distributing stresses through the device and minimizing localized stresses in the curved regions. In addition, the looped elements may be expandable between expanded and compressed states for increasing and reducing a periphery of the body in the transverse orientation, respectively. The looped elements may be biased towards one of the compressed and expanded states.

Adjacent tines of the device may have a first curved region disposed between them. The first curved region between adjacent tines may include a substantially blunt element extending towards the central axis. The blunt element may have a length shorter than lengths of the adjacent tines.

The tines of the device may include first and second primary tines, having a first length and a second length, respectively, which may be the same as or different than one another. The first and second primary tines may be disposed on opposing first curved regions, and may be oriented substantially towards each other in the planar configuration. In the planar configuration, the first and second primary tines may at least partially overlap the body or each other. The tines may also include one or more secondary tines having a length substantially shorter than the first and second lengths of the primary tines. The secondary tines may be disposed on either side of the first and second primary tines.

A first primary tine, having a first length, may extend from the body towards the central axis in the planar configuration, and may be deflectable out of the plane when the body is moved towards the transverse configuration. A second primary tine, having a second length, may extend from the body towards the first tine when the body is in the planar configuration, and may be deflectable out of the plane when the body is moved towards the transverse configuration. The lengths of the first and second primary tines may cause the primary tines to at least partially overlap in the planar configuration. The body may be biased towards the planar configuration to bias the tines generally towards the central axis.

The device may include a set of secondary tines having a length shorter than the first and second lengths. The secondary tines may extend from the body towards the central axis in the planar configuration, and may be deflectable out of the plane when the body is moved towards the transverse configuration. In an exemplary embodiment, a secondary tine may be disposed on either side of the first primary tine, and a secondary tine may be disposed on either side of the second primary tine.

Optionally, adjacent tines may have a first curved region disposed between them. The first curved region between adjacent tines may include a substantially blunt element extending towards the central axis. The blunt element may have a length shorter than lengths of the adjacent tines.

Also, the device may include a plurality of looped elements disposed around a periphery of the body. The looped elements may generally define an endless zigzag pattern extending about the central axis. The first primary tine and the second primary tine may extend from looped elements disposed opposite one another. The looped elements may be expandable between expanded and compressed states for increasing and reducing a periphery of the body in the transverse orientation, respectively. The looped elements may be biased towards one of the compressed and expanded states.

In any event, the primary tines of the clips of the present invention will be offset from the axis of symmetry of the loop from which they extend. The offsetting of the primary tines is achieved by simply relocating the primary tines which are directly attached to the loop to a location which is not on the axis of symmetry of the loop or providing an intermediate connecting element between the tines and the axis of symmetry of the curved region of the loop from which the tine extends. This connecting element is straight or linear, but may also be curved. The connecting element can be connected to a point or region on the axis of symmetry of the loop to enhance consistency of performance of the clip during deployment. The offsetting of the tines is believed to reduce any tendency to wander during deployment, which the tines might otherwise have.

In another aspect of the present invention, a method is provided for manufacturing a clip from an elastic material, such as a sheet of superelastic alloy, e.g., a nickel-titanium alloy ("Nitinol"). The components of the clip, e.g., a generally-annular body, optionally including looped elements, and/or tines, may be formed by removing portions from the sheet. The portions may be removed, e.g., by laser cutting, chemical etching, photo chemical etching, stamping, electrical discharge machining, and the like, or by the method disclosed in one or more of the incorporated by reference patents or patent applications. The clip may be polished using one or more processes, such as electro-polishing, chemical etching, tumbling, sandblasting, sanding, and the like, and/or heat-treated to provide a desired finish and/or desired mechanical properties. Optionally, the body and tines may be coated with a therapeutic agent, e.g., a peptide coating and/or one or more clotting factors.

In addition or alternatively, the clip may be disposed in a planar configuration, e.g., upon forming the clip from the sheet, and heat treated to form a clip biased to the planar configuration. For example, the clip may be formed from a shape memory material, e.g., Nitinol, which may substantially recover the planar configuration when heated to a first predetermined temperature corresponding to an austenitic state, e.g., a temperature close to body temperature. The clip may be cooled to a second predetermined temperature corresponding to a martensitic state, e.g., a temperature at or below ambient temperature, and malleably manipulated.

For example, the clip formed from the sheet may be deformed to a transverse configuration, such as that described above, e.g., by loading the clip onto a mandrel or directly onto a delivery device. If the clip includes looped elements formed from the body, the looped elements may be biased upon heat treatment towards an expanded state, but may be malleably deformed to a compressed state upon cooling, e.g., to facilitate loading onto the delivery device. Alternatively, the clip may be formed from a superelastic material, e.g., Nitinol, such that the clip may be resiliently deformed to the transverse configuration and/or compressed state, yet may automatically attempt to resume its planar configuration and/or expanded state upon release from external forces.

In still another aspect of the present invention, a method for closing an opening in a wall of a body lumen is provided. The distal end of an elongate member may be advanced through an opening in a patient's skin, along a passage through tissue, and into the body lumen. A distal portion of an obturator may be positioned distally beyond the distal end of the elongate member along the passage within the body lumen. One or more expandable elements on the distal portion of the obturator may be expanded transversely. The obturator may be withdrawn from the passage until the expandable elements contact the wall of the body lumen, thereby providing a tactile indication of a location of the wall of the body lumen between the elongate member and the plurality of expandable elements of the obturator.

A clip may be advanced into the passage over the elongate member until tines of the clip penetrate the wall of the body lumen, the tines and the expandable elements on the obturator being angularly offset from one another such that the tines penetrate the wall at locations between the expandable elements. The obturator may be collapsed, and the elongate member and/or obturator may be withdrawn from the body lumen and passage, leaving the clip to substantially close the opening in the wall of the body lumen. When the elongate member is withdrawn, the tines may automatically at least partially move towards a planar configuration to substantially close the opening. The clip may also be delivered to the desired site by using the apparatus and methods disclosed in U.S. patent application Ser. No. 10/356,214, filed Jan. 30, 2003 and Ser. No. 10/638,115, filed Aug. 8, 2003. The clip may also be manufactured according to the method set forth in U.S. patent application Ser. No. 10/335,075, filed Dec. 31, 2002.

Advancing the clip may include puncturing the wall of the body lumen with the primary tines until tips of the primary tines enter the body lumen, and puncturing the wall of the body lumen with the secondary tines. The primary tines and the secondary tines may puncture the walls without contacting the expandable elements of the obturator.

The present invention also relates to a method for closing an opening in a wall of a body lumen. The method can include advancing a distal end of an elongate member within the body lumen, the elongate member having a distal portion that assists in presenting the wall for receiving a clip having a plurality of tissue engaging portions having tips that point generally toward a central axis of the clip. Further, the method can include advancing the clip relative to the elongate member and the wall of the body lumen until the plurality of tissue engaging portions penetrate the wall of the body lumen. Optionally, the clip can be advanced until a distal end of the plurality of tissue engagement portions penetrate the wall but do not enter the body lumen. Stated another way, the method can include stopping advancement of the clip before the distal end of the plurality of tissue engagement portions enter the body lumen. Once the clip penetrates the wall, the elongate member can be withdrawn from the body lumen, leaving the clip to substantially close the opening in the wall of the body lumen.

According to another aspect, the method can include advancing a second elongate member relative to the elongate member, the clip slidably cooperating with the second elongate member. Withdrawing the second elongate member relative to the elongate member following penetration of the plurality of tissue engaging portions into the wall of the body lumen can enable the plurality of tissue engaging portions to automatically at least partially move towards a planar configuration to substantially close the opening.

The method can also related to closing a opening in a wall of a body lumen by (i) advancing a distal end of a first elongate member within the body lumen, the elongate member having a distal portion that assists in presenting the wall for receiving a clip having a plurality of tissue engaging portions symmetrically disposed about the clip, (ii) advancing the clip relative to the elongate member and the wall of the body lumen, as the distal portion of the elongate member assists with presenting the wall for receiving the clip, until the plurality of tissue engaging portions penetrate the wall of the body lumen, the tissue engaging portions and the distal portion of the elongate member being angularly offset from one another; and (iii) withdrawing the elongate member from the body lumen, leaving the clip to substantially close the opening in the wall of the body lumen.

To aid with positioning the clip relative to the wall, the method can further include positioning the distal portion of the first elongate member relative to the wall to assist in presenting the wall for receiving the clip to close the opening. In addition, the method can include moving the clip within a carrier assembly that moves relative to a second elongate member, toward the distal portion of the first elongate member until the clip deploys from within the carrier assembly.

Still another method of closing an opening in a wall of a body lumen can include advancing a distal end of a first elongate member within the body lumen, the elongate member having a distal portion that assists in presenting the wall for receiving a clip having a plurality of tissue engaging portions symmetrically disposed about the clip. The method can further include positioning a distal end of a second elongate member relative to the first elongate member, the second elongate member having a carrier assembly that receives the clip, and advancing the clip relative to the wall of the body lumen, as the distal portion of the first elongate member assists with presenting the wall for receiving the clip, until the plurality of tissue engaging portions penetrate the wall of the body lumen. Once the clip penetrates the wall, the method can include withdrawing the first elongate member and the second elongate member from the body lumen, leaving the clip to substantially close the opening in the wall of the body lumen.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1A:
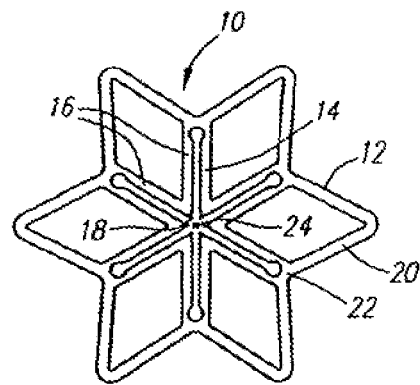
FIG. 1A illustrates a top view of a first embodiment of a clip including a plurality of tissue engaging portions in a planar orientation, in accordance with the present invention.

The present invention is directed to devices and methods for engaging tissue, e.g., to connect tissue segments together or to close and/or seal openings through tissue, such as in a wall of a body lumen. More particularly, the present invention is directed to vascular closure devices or clips for closing a puncture in a wall of a blood vessel formed during a diagnostic or therapeutic procedure, and to methods for making and using such devices.

Turning now to the drawings, FIGS. 1A-1D show a first embodiment of a closure device or clip 10 for closing an incision, puncture, or other passage communicating with a blood vessel or other body lumen (not shown). The clip 10 includes a peripheral body 12 and a plurality of tissue engaging portions 14. Each tissue engaging portion 14 includes a pair of legs 16 terminating in a tine 18 configured for penetrating or otherwise engaging tissue. The tines 18 may include a variety of known pointed tips, such as a bayonet tip, and/or may include barbs (not shown) along an edge or planar surface of the tine 18. The tissue engaging portions 14 are disposed substantially symmetrically about a central axis 24. The body 12 also can include a plurality of expandable cells 20 that are connected by hinged regions 22 that also connect adjacent tissue engaging portions 14.

In another embodiment, the body 12 and tissue engaging portions 14 are integrally formed from a single sheet of material, such as a superelastic alloy, such as a nickel-titanium ("Nitinol") alloy. Portions of the sheet may be removed using conventional methods, such as laser cutting, chemical etching, and the like, to form the clip 10. FIG. 1A shows the clip 10 with the tissue engaging portions 14 in a substantially planar configuration lying in a plane defined by the sheet. The clip 10 may include one or more radiopaque markers or other markers visible using external imaging, such as fluoroscopy. For example, the entire clip 10 may be coated with radiopaque material, or one or more discrete markers may be provided at predetermined locations on the clip 10.

Figure 1B:
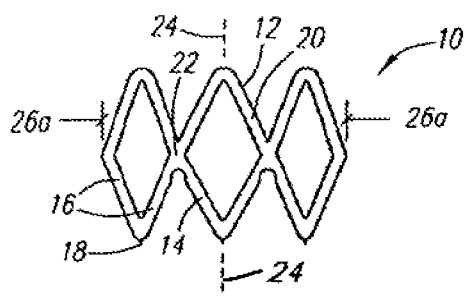
FIGS. 1B and 1C illustrate side views of the clip of FIG. 1A, with the tissue engaging portions oriented substantially transversely from the planar orientation, in reduced and expanded diameters, respectively.
Figure 1C:
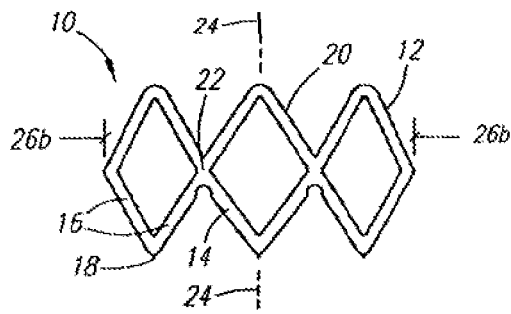
Figure 1D:
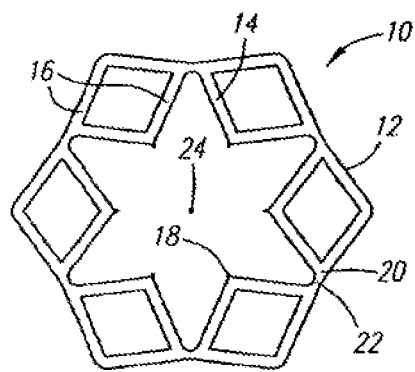
FIG. 1D illustrates a top view of the clip of FIG. 1A with the tines oriented substantially transversely from the planar orientation.

As shown in FIGS. 1B and 1D, the tissue engaging portions 14 may be deflected such that they extend from the body 12 substantially transversely with respect the plane defined by the sheet. The tissue engaging portions 14 can be oriented substantially parallel to the axis 24 to define a transverse configuration, as shown in FIG. 1B. Alternatively, the tissue engaging portions 14 may define an angle with respect to the axis 24, as shown in FIG. 1D. In the clip's transverse configuration, the body 12 has a generally annular shape, e.g., a hexagonal shape as shown in FIG. 1D. The body 12 is sufficiently flexible such that the clip 10 assumes a generally circular or elliptical shape (not shown), e.g., conforming to an exterior surface of a delivery device (not shown) used to delivery the clip 10.

The tissue engaging portions 14 can be biased from the transverse configuration towards one another, i.e., towards the planar configuration of FIG. 1A. Thus, with the tissue engaging portions 14 in the transverse configuration, the tines 18 may be engaged with tissue, e.g. adjacent to a puncture site. When the clip 10 is released, the tissue engage portions 14 may attempt to return to the planar configuration, thereby drawing the engaged tissue together and substantially closing and/or sealing the puncture site.

In addition, the expandable cells 20 may be expandable from a compressed state, shown in FIG. 1B, to an expanded state, shown in FIG. 1C. The expandable cells 20 can be biased to the expanded state, but may be compressed to the compressed state, e.g., by constraining the clip 10. In one embodiment, the clip 10 is formed with the expandable cells 20 in the expanded state. With the clip in its transverse configuration, the expandable cells 20 may be circumferentially and/or radially compressed to the compressed state such that the clip 10 defines a first diameter 26a, shown in FIG. 1B. The clip 10 may be constrained at the first diameter, e.g., by loading the clip 10 into a delivery device (not shown), as described further below. When released from the constraint, e.g., when deployed from the delivery device, the clip 10 may automatically expand to a second diameter 26b, shown in FIG. 1C. Thus, the expandable cells 20 may reduce the profile of the clip 10 during delivery, e.g., to facilitate introduction of the clip 10 through a smaller puncture or other passage.

In an alternative embodiment, the clip 10 may be formed from a shape memory alloy, e.g., Nitinol, with the expandable cells in the compressed state. With the clip 10 in the transverse configuration, the clip 10 may be expanded, e.g., by applying a force radially outwards against an inner surface of the clip 10, thereby expanding the expandable cells 20 to the expanded state and expanding the clip 10 to the second diameter 26b. The expandable cells 20 may then be heat treated to cause the expandable cells 20 to "remember" the expanded state, as is known to those skilled in the art. It may also be necessary to subsequently heat treat the clip 10 further, e.g. with the tissue engaging portions 14 in the planar configuration to cause the tissue engaging portions 14 to "remember" and be biased to the planar configuration, as is known to those skilled in the art.

Figure 2:
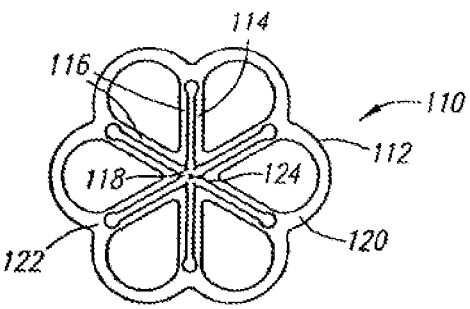
FIG. 2 illustrates a top view of another embodiment of a clip, in accordance with the present invention.

Turning to FIG. 2, another embodiment of a clip 110 is shown that includes a peripheral body 112 and a plurality of tissue engaging portions 114. Each tissue engaging portion 114 includes a pair of legs 116 terminating in a tine 118. The tissue engaging portions 114 are disposed substantially symmetrically about a central axis 124. The body 112 also can include a plurality of expandable cells 120 that are connected by hinged regions 122 that also connect adjacent tissue engaging portions 114, similar to the first embodiment described above.

The tissue engaging portions 114 may be deflected such that they extend substantially transversely from the body 112 (not shown). The tissue engaging portions 114 may be oriented substantially parallel to the axis 124 to define a transverse configuration such that the body 112 has a generally annular shape. The tissue engaging portions 114 can be biased from the transverse configuration towards one another, i.e., towards the planar configuration of FIG. 2, similar to the previous embodiment.

The expandable cells 120 have a generally arcuate shape that may be expandable from a first width to a second wider width (not shown), behaving similarly to the diamond-shaped cells of the previous embodiment. Thus, the expandable cells 120 may be biased to the expanded state, but may be compressed to the compressed state, as described above.

Figure 3:
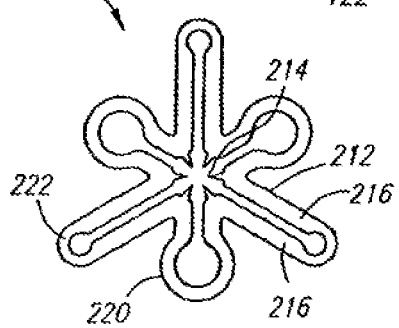
FIG. 3 illustrates a top view of another embodiment of a clip, in accordance with the present invention.

Turning to FIG. 3, another embodiment of a clip 210 is shown that includes a peripheral body 212 including a plurality of arms 216 extending between tissue engaging portions or tines 214; expandable cells 220, and hinged regions 222. The clip 210 can be formed from a single sheet of material, similar to the embodiments described above, with the tines 214 biased to a planar configuration, as shown. The body 212 is deflectable to a transverse configuration (not shown) such that the tines 212 are oriented substantially transversely with respect to the plane of the sheet. The body 212, and particularly the arms 216, are sufficiently flexible such that the clip 210 may assume a generally annular shape in the transverse configuration, e.g., to facilitate loading of the clip 210 onto a delivery device (not shown).

The expandable cells 220 are substantially enclosed loops that may at least partially open from a compressed state (shown in FIG. 2), to an expanded state (not shown). The loops can be biased to the expanded state, similar to the embodiments described above, thereby allowing the clip 210 to assume a reduced diameter and an expanded diameter.

Figure 4:
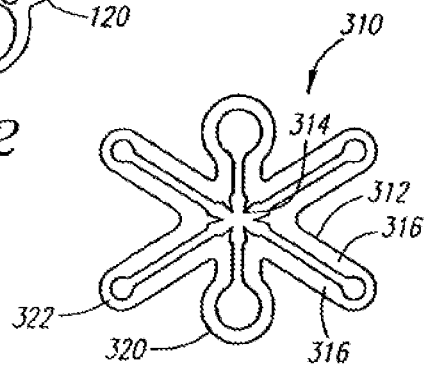
FIG. 4 illustrates a top view of another embodiment of a clip, in accordance with the present invention.

Turning to FIG. 4, another embodiment of a clip 310 is shown, that is similar to the embodiment shown in FIG. 3, except that the clip 310 includes only two expandable cells 320. The expandable cells 320 are still disposed in a substantially symmetrical arrangement to facilitate expansion of the clip 310 in a generally uniform manner. As will be appreciated by those skilled in the art, a clip in accordance with the present invention may have a variety of configurations, including two or more tissue engaging portions or tines, and including one or more expandable cells (or optionally no expandable cells). The tissue engaging portions and/or expandable cells can be arranged in a substantially symmetrical configuration, for example, about a central axis.

Figure 5:
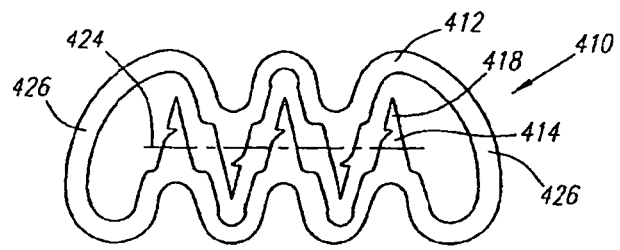
FIG. 5 illustrates a top view of another embodiment of a clip, in accordance with the present invention.

Turning to FIG. 5, another embodiment of a clip 410 is shown that includes a peripheral body 412 and a plurality of tissue engaging portions 414 terminating in tines 418. The clip 410 may be formed from a single sheet of material, such as Nitinol, similar to the embodiments described above.

Figure 6:
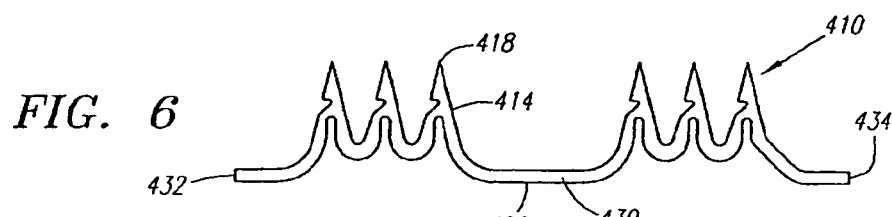
FIG. 6 illustrates a top view of the clip of FIG. 5 with the clip unwound from its annular shape.

Alternatively, as shown in FIG. 6, the clip 410 may be formed from an elongate wire 430, e.g., a solid rod or hollow tube, such as a length of hypotube. The tube 430 can be semi-rigid or flexible, thereby accommodating deflection of the clip 410 between its planar and transverse configurations, as described further below. The tube 430 may be bent and tines 418 may be formed therein using conventional methods. Alternatively, tines 418 may be formed separately and attached to the tube 430, for example, by welding. The tube 430 may then be wound into an enclosed loop and the ends 432, 434 may be connected together, e.g., by welding, to provide a clip 410, such as that shown in FIG. 5.

In this embodiment, the tissue engaging regions 414 are disposed in opposing sets along an axis of symmetry 424 extending between looped regions 426, defining a substantially planar configuration. The tissue engaging portions 414 may be directed substantially transversely with respect to a plane defined by the planar configuration, but can be biased to return towards the planar configuration, similar to the embodiments described above.

Figure 7A:
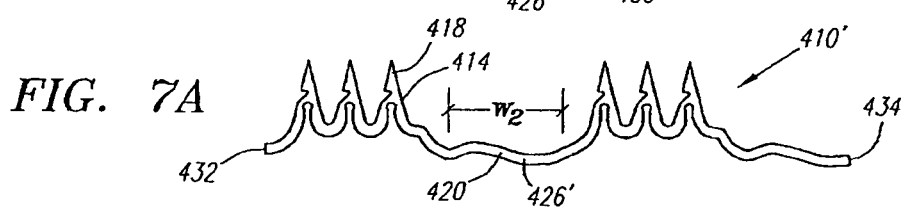
FIGS. 7A and 7B illustrate top views of an alternative embodiment of the clip of FIG. 5, the clip shown unwound and including expandable elements shown in their expanded and compressed states, respectively.
Figure 7B:
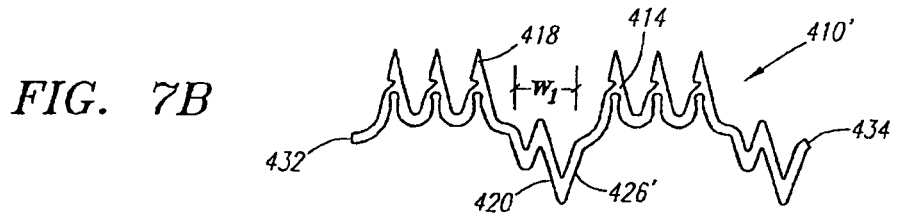
Figure 8A:
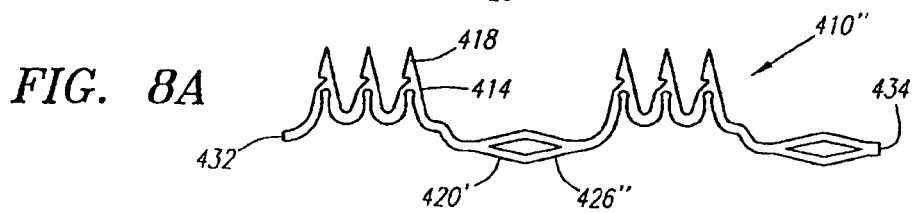
FIGS. 8A and 8B illustrate top views of another alternative embodiment of the clip of FIG. 5, the clip shown unwound and including expandable cells shown in their expanded and compressed states, respectively.
Figure 8B:
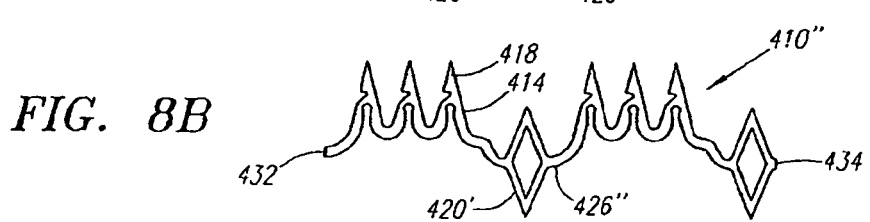

In an alternative embodiment, shown in FIGS. 7A and 7B, the regions 426' between the tissue engaging portions 414 include expandable elements 420, having a zig-zag shape, that are expandable between a compressed state and an expanded state. Thus, when the tube 412' is wound to form a clip (not shown), the zig-zag elements 420 are disposed at the looped regions 426' of the clip. The zig-zag elements 420 have a first width $w_2$ in the compressed state (FIG. 7B) and a second width $w_2$ in the expanded state that is larger than the first width (FIG. 7A). In a further alternative embodiment, shown in FIGS. 8A and 8B, the expandable elements are substantially enclosed cells 420', optionally having a diamond shape. Thus, similar to the embodiments described above, the expandable elements or cells allow the clip 410" to assume first and second diameters.

Figure 9:
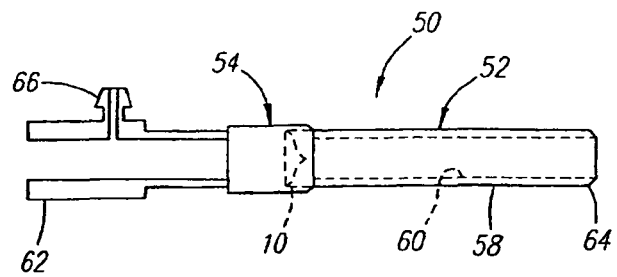
FIG. 9 illustrates a side view of an apparatus for delivering a clip, including an introducer sheath and an actuator assembly, in accordance with the present invention.

Turning to FIG. 9, an apparatus 50 is shown that may be used to deliver a clip, such as any of the embodiments described above. Generally, the apparatus 50 includes an introducer sheath 52, and a housing 54 slidably disposed on the sheath 52. The sheath 52 includes a substantially flexible or semi-rigid tubular body 58 including a lumen 60 extending between its proximal and distal ends 62, 64. The distal end 64 has a size and shape to facilitate insertion into a blood vessel, e.g., having a tapered tip for facilitating substantially atraumatic introduction through the passage and at least partially into the vessel. The lumen 60 has a size for accommodating insertion of one or more devices therethrough, such as a catheter, guidewire, and the like (not shown). The sheath 52 also can include a seal (not shown), such as a hemostatic valve, within the lumen 60 at or near the proximal end 62 that provides a fluid-tight seal, yet accommodates insertion of one or more devices into the lumen 60 without fluid passing proximally from the sheath 52.

Optionally, the sheath 52 may include a side port 66 that communicates with the lumen 60, for example, to allow the infusion of fluids into the lumen 60, through the sheath 52. Alternatively, or in addition, the side port 66 may be used to provide a "bleed back" indicator, such as that disclosed in U.S. Pat. No. 6,626,918, entitled "Apparatus and Methods for Positioning a Vascular Sheath," which is assigned to the assignee of the present invention, and the disclosures of which, and any references therein, are incorporated herein in their entirety by this reference. Alternatively, the apparatus 50 may include a mechanical locator (not shown), such as that disclosed in U.S. Pat. No. 6,780,197, filed on the same day with U.S. Pat. No. 6,719,777, entitled "Apparatus and Method for Delivering a Closure Device," the disclosures of which, and any references therein, are incorporated herein in their entirety by this reference.

The housing 54 is slidably disposed on an exterior of the sheath 52, the housing 54 configured for releasably holding the clip 10, e.g., within an annular cavity therein (not shown). The housing may be substantially permanently attached to the sheath 52 or, alternatively, the housing 54 may be attachable to the sheath 52, e.g., using an outer sleeve (not shown). This outer sleeve may have the housing thereon, and the sleeve may be advanced over the sheath 52, and coupled thereto at any time during its use. Exemplary embodiments of a housing for use with an apparatus in accordance with the present invention are disclosed in U.S. Pat. Nos. 6,197,042, 6,461,364, and 6,391,048, the disclosures of which, and any references therein, are incorporated herein in their entirety by this reference.

The housing 54 is actuable from the proximal end 62 of the sheath 52, for example, by a housing actuator assembly (not shown), for advancing the clip 10 distally during deployment. A rod, cable, or other control wire (not shown) may couple the housing 54 to the actuator assembly. The housing actuator assembly may be detachable from the sheath 52, e.g., to facilitate introduction of devices into the lumen 60. In one embodiment, the actuator may be biased to advance the housing 54 upon activation. Thus, when activated, the housing 54 may be advanced towards the distal end of the sheath 52 to deploy the clip 10.

Turning to FIGS. 10A-10D, the apparatus 50 may be used to deliver a clip 10, e.g., to close and/or seal an incision, puncture, or other passage 92 that extends from a patient's skin 94 through intervening tissue 96, and a wall 98 of the vessel 90. Alternatively, the apparatus 50 may be used to deliver any of the clips disclosed herein to engage tissue in other procedures, e.g., to connect tissue segments together or otherwise to secure tissue structures engaged by the clip with respect to one another. For example, the apparatus and clip may be used to attach an anastomosis during a bypass procedure. It will be appreciated by those skilled in the art that a clip and/or apparatus in accordance with the present application may be useful in a variety of procedures, including tubal ligations, and the like.

Generally, the clip 10 is pre-loaded in the housing 54 before the procedure. The clip 10 may be constrained in its substantially transverse configuration and then introduced over the distal end 64 of the sheath 52 and into the cavity or otherwise loaded in the housing 54. Because the tissue engaging portions (not shown) of the clip 10 are biased to a planar configuration, they may engage an inner wall (not shown) of the housing 54 or an outer surface of the sheath 52, thereby constraining the clip 10 in its transverse configuration. Alternatively, the clip 10 may be directed over the distal end 64 of the sheath 62, thereby causing the tissue engaging portions to deflect transversely from the planar configuration towards a substantially axial or distal configuration.

Figure 10A:
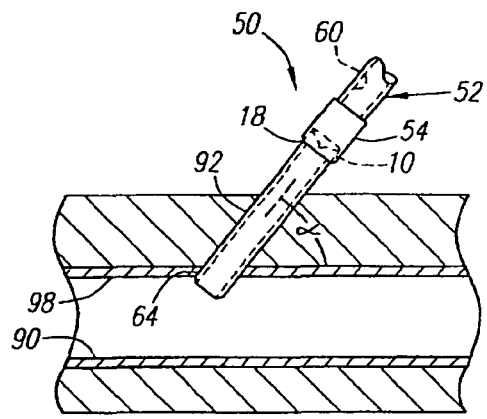
FIGS. 10A-10D illustrates cross-sectional views of a blood vessel, showing a method for delivering a closure device into a passage communicating with the vessel such that the closure device engages the vessel wall.

As shown in FIG. 10A, the sheath 52 may be inserted or otherwise positioned within the blood vessel 90, i.e., through the passage 92. The sheath 52 can be provided with the housing 54 in its proximal position, e.g., without the housing actuator assembly (not shown) attached. Alternatively, the housing actuator assembly may be provided attached to the sheath 52 as long as the lumen 60 may be accessed. In a further alternative, the housing 54 may be provided separately from the sheath 62 with the clip 10 preloaded therein. For example, the housing 54 may be provided on an elongate member, such as a tubular or U-shaped sleeve (not shown), that may be advanced over and coupled to the sheath 52 at any time before deployment of the clip 10. The housing actuator may be coupled to the sleeve and/or may be attachable to the sleeve.

The sheath 52 may be advanced over a guidewire or other rail (not shown) previously positioned through the passage 92 into the blood vessel 90 using a conventional procedure. The blood vessel 90 can be a peripheral vessel, such as a femoral, radial, or carotid artery, although other body lumens may be accessed using the sheath 52, as will be appreciated by those skilled in the art.

The passage 92, and consequently the sheath 52, may be oriented at a substantially acute angle "alpha" with respect to the vessel 90, thereby facilitating introduction of devices through the lumen 60 of the sheath 52 into the vessel 90 with minimal risk of damage to the vessel 90. One or more devices, such as a guide wire, a catheter, and the like (not shown), may be inserted through the sheath 52 and advanced to a desired location within the patient's body. For example, the devices may be used to perform a therapeutic or diagnostic procedure, such as angioplasty, atherectomy, stent implantation, and the like, within the patient's vasculature.

After the procedure is complete, the device(s) may be removed from the sheath 52. The sheath 52 may be manipulated to position the distal end 64 with respect to the opening 92, e.g., to ensure that the housing 54 is advanced to properly deploy the clip 10 in the wall 98 of the vessel 90. Bleed back or mechanical locators may be used to facilitate this positioning.

Figure 10B:
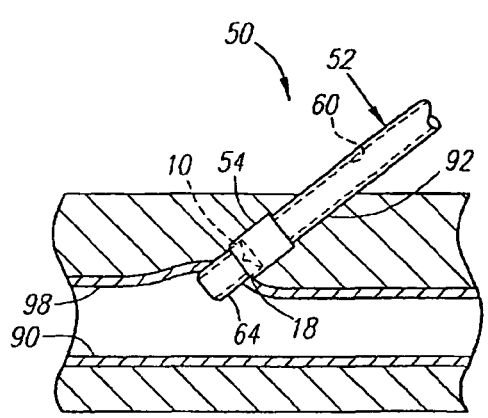

As shown in FIG. 10B, with the sheath 52 properly positioned, the housing 54 may be actuated, for example, to advance the housing 54 distally into the passage 92 to deliver the clip 10. Movement of the housing 54 with respect to the distal end 64 of the sheath 52 can be limited, e.g., by the actuator assembly. Thus, the housing 54 may only be advanced a fixed distance such that the clip 10 substantially engages the wall 98 of the blood vessel 90, e.g., until the tines 18 penetrate but do not pass completely through the wall 98. Once the clip 10 is successfully deployed within the passage 92, i.e., into the wall 98 of the vessel 90, the apparatus 50 may be withdrawn from the passage 92.

In addition, as the clip 10 is deployed from the housing 54, the clip 10 may expand radially to an enlarged diameter (not shown), for example, if the clip 10 includes expandable elements (not shown), such as those described above. Thus, the clip 10 may be compressed into the housing 54, e.g., thereby allowing a smaller profile housing 54 to be used. The clip 10 may be expanded upon deployment to engage a larger area of tissue adjacent the opening in the wall 98 of the vessel 90.

Figure 10C:
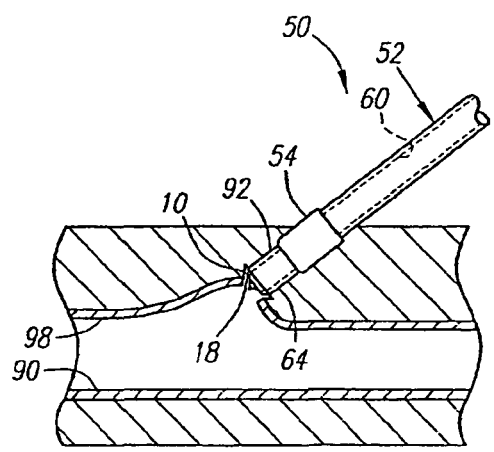
Figure 10D:
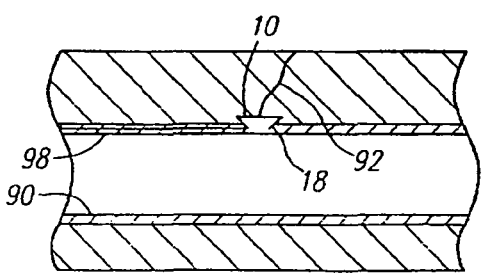

As shown in FIG. 10C, as the distal end 64 of the sheath 52 is withdrawn proximally from around the clip 10, the tines 18 of the clip 10 are free to return towards the planar configuration. Thus, the tines 18 begin automatically to move from a substantially axial configuration to a less transverse configuration. Because the tines 18 are engaged to the tissue, however, they may not return completely to the planar configuration. Because of the bias to the planar configuration, however, the tines 18 automatically pull the tissue together, thereby closing and/or sealing the passage 92, as shown in FIG. 10D. In addition, if desired a sealant or other material may be introduced into the passage 92 in conjunction with or separate from delivery of the clip 10 to further seal the passage 92, as is known to those skilled in the art.

Figure 11A:
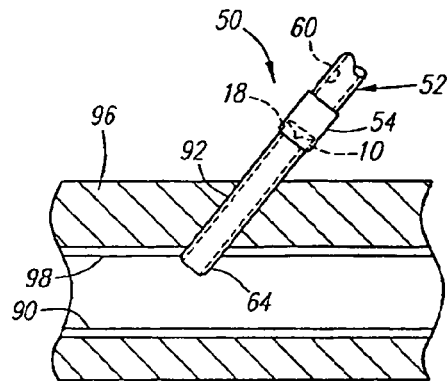
FIGS. 11A-11D illustrate cross-sectional views of a blood vessel, showing another method for delivering a closure device into a passage communicating with the vessel such that the closure device engages extra-vascular tissue proximal to the vessel wall.
Figure 11B:
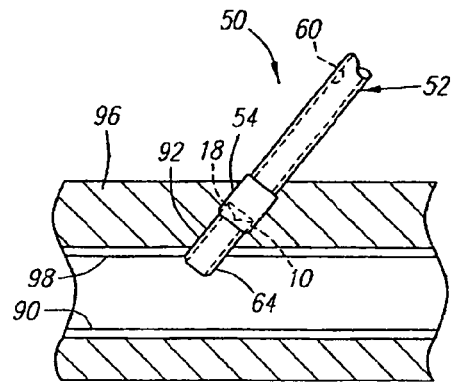
Figure 11C:
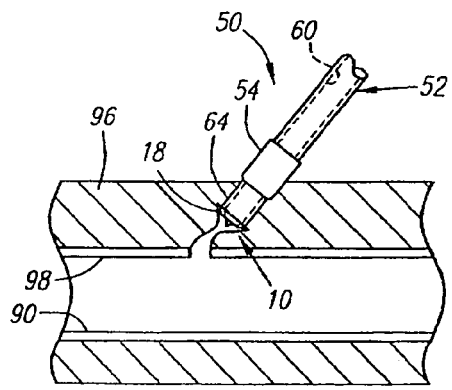
Figure 11D:
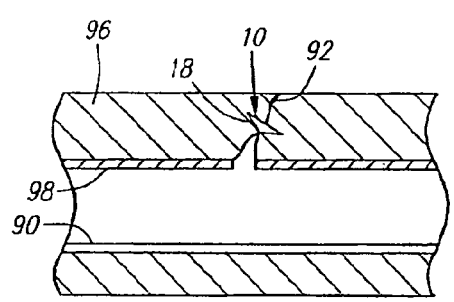

Turning to FIGS. 11A-11C, another method is shown in which the apparatus 50 may be used to deliver a clip 10, e.g., to engage intervening tissue 96 to close and/or seal an incision, puncture, or other passage 92 that extends from a patient's skin 94 through the intervening tissue 96, to a wall 98 of the vessel 90. As shown in FIG. 11A, the sheath 52 may be inserted or otherwise positioned within the blood vessel 90, i.e., through the passage 92. One or more devices (not shown) may be inserted through the sheath 52 to perform a procedure within the patient's body. After the procedure is complete, the device(s) may be removed from the sheath 52, and the sheath 52 may be manipulated to position the distal end 64 within the passage 92.

Turning to FIG. 11B, with the sheath 52 properly positioned, the housing 54 may be actuated, for example, to advance the housing 54 distally into the passage 92 to deliver the clip 10 to a location between the patient's skin 94 and the vessel wall 98. The clip 10 may be deployed from the housing 54, thereby substantially engaging fascia or other intervening tissue 96 with the tines 18. Once the clip 10 is successfully deployed within the passage 92, the apparatus 50 may be withdrawn from the passage 92.

As shown in FIG. 11C, as the distal end 64 of the sheath 52 is withdrawn proximally from around the clip 10, the tines 18 of the clip 10 are free to return towards the planar configuration. Because of the bias to the planar configuration, the tines 18 automatically pull the tissue together, thereby closing and/or sealing the passage 92, as shown in FIG. 10D.

Figure 12:
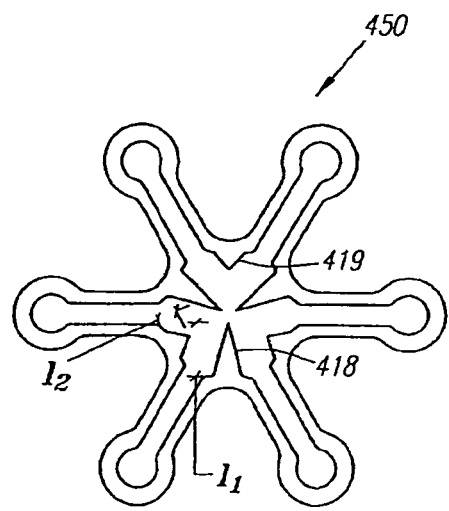
FIG. 12 illustrates a top view of an alternative embodiment of a clip, in accordance with the present invention.

In a further alternative, shown in FIG. 12, a clip 450 may be provided that includes a first set of tines 418 having a first length $l_1$, and a second set of tines 419 having a second length $l_2$ substantially shorter than the first length $l_1$. During use, similar to one of the methods described above, the clip 450 may be deployed such that the first set of tines 418 penetrate into and/or engage the wall of a blood vessel or other body lumen (not shown), while the second set of tines 418 engage extra-vascular tissue, i.e., tissue between the vessel wall and the patient's skin. Thus, the clip 450 may simultaneously close both the opening in the vessel wall and the passage through the intervening tissue.

Figure 13:
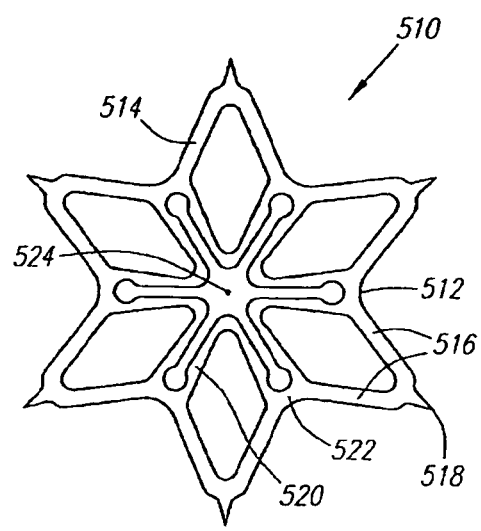
FIGS. 13-15 illustrate top views of additional embodiments of a clip, in accordance with the present invention.

Turning to FIG. 13, another embodiment of a clip 510 is shown for engaging tissue, in accordance with the present invention. The clip 510 includes a peripheral body 512 and a plurality of tissue engaging portions 514. Each tissue engaging portion 514 includes a pair of legs 516 terminating in a tine 518 configured for penetrating or otherwise engaging tissue. The tissue engaging portions 514 are disposed substantially symmetrically about a central axis 524. The body 512 also can include a plurality of expandable cells 520 that are connected by hinged regions 522 that also connect adjacent tissue engaging portions 514, the cells 520 behaving similar to the embodiments described above.

In another embodiment, the body 512 and tissue engaging portions 514 are integrally formed from a single sheet of material, such as a Nitinol, similar to the embodiments described above. The clip 510 is shown in a relaxed state with the tissue engaging portions 514 disposed radially outward in a substantially planar configuration. Similar to the previous embodiments, the tissue engaging portions 514 may be deflected such that they extend from the body 512 substantially transversely with respect the plane defined by the sheet (similar to FIG. 1B).

The tissue engaging portions 514 can be biased from the transverse configuration away from one another, i.e., towards the planar configuration. Thus, with the tissue engaging portions 514 in the transverse configuration, the tines 518 may be engaged with tissue. When the clip 510 is released, e.g., from within a delivery device, the tissue engage portions 514 may attempt to return to the planar configuration, thereby securing the tissue with respect to the clip 510.

In addition, the clip 510 may include expandable cells 520 that are expandable from a compressed state to an expanded state (similar to FIG. 1C), similar to the previous embodiments. The expandable cells 520 can be biased to the expanded state, but may be compressed to the compressed state, e.g., by constraining the clip 510. Alternatively, any of the clips described herein may be biased to the compressed state but may be expanded to the expanded state, e.g., by constraining the clip over a sheath or other elongate member.

Figure 14:
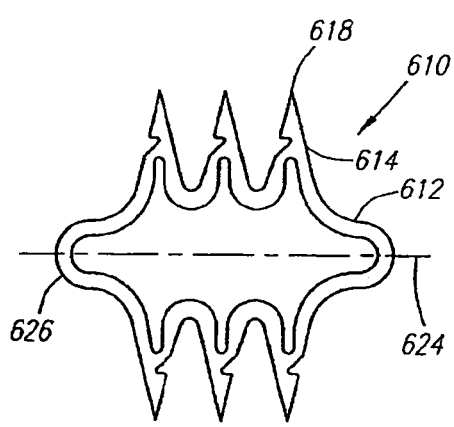

Turning to FIG. 14, yet another embodiment of a clip 610 is shown that includes a peripheral body 612 and a plurality of tissue engaging portions 614 terminating in tines 618. The clip 610 may be formed from a single sheet of material, such as Nitinol or may be formed from a wire, rod or tube (not shown), similar to the embodiments described above. The tissue engaging regions 614 are disposed in opposing sets oriented away from one another along an axis of symmetry 624, defining a substantially planar configuration.

The tissue engaging portions 614 may be directed substantially transversely with respect to a plane defined by the planar configuration, for example, by loading the clip 614 into a housing or lumen of a delivery device (not shown). The tissue engaging portions 614 can be biased to move away from one another, i.e., towards the planar configuration. In an alternative embodiment, the looped regions 626 or other regions of the body 612 may include expandable elements (not shown), e.g., having a zig-zag shape, a diamond shape, and the like.

Figure 15:
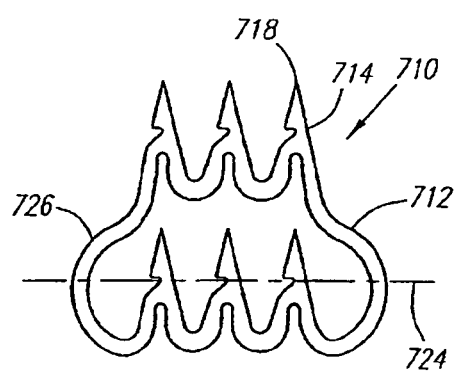

Turning to FIG. 15, still another embodiment of a clip 710 is shown that includes a peripheral body 712 and a plurality of tissue engaging portions 714 terminating in tines 718. The clip 710 is similar to the previous embodiment, except that the tissue engaging regions 714 are disposed in opposing sets along an axis of symmetry 724, but are oriented in a common direction. The tissue engaging portions 714 may be directed substantially transversely with respect to a plane defined by the planar configuration. The tissue engaging portions 714 can be biased to return towards the planar configuration shown. In an alternative embodiment, the looped regions 726 or other regions of the body 712 may include expandable elements (not shown), e.g., having a zig-zag shape, a diamond shape, and the like, similar to the previous embodiments.

The clip 710 may be constrained on a delivery apparatus (not shown), similar to that described above, such that the tissue engaging portions 714 are all directed substantially transversely, and optionally distally, to facilitate their engagement into tissue during deployment, as will be appreciated by those skilled in the art. Unlike previous embodiments, which may close tissue around an opening, this embodiment may be useful when it is desired to maintain the relative position of tissue being engaged by the clip 710.

Figure 16A:
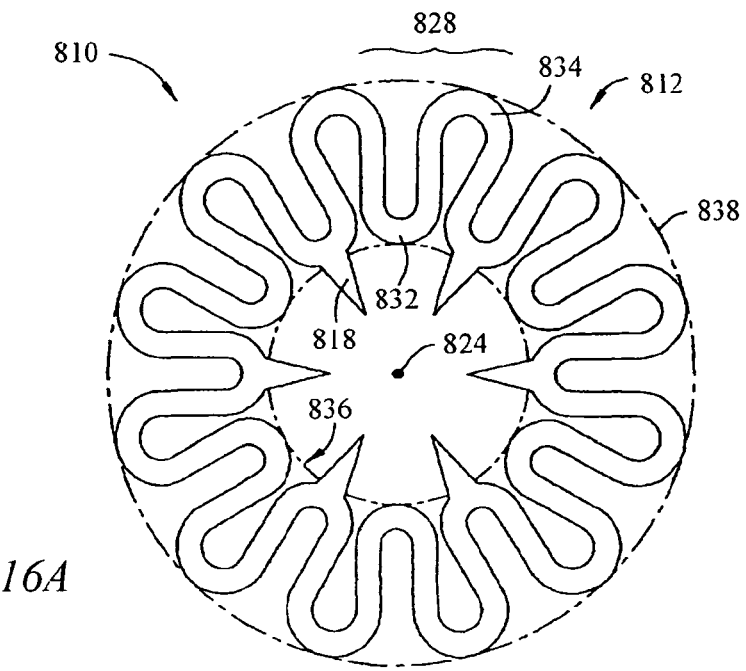
FIG. 16A illustrates a top view of another embodiment of a clip including a plurality of tines in a planar orientation, in accordance with the present invention.
Figure 16B:
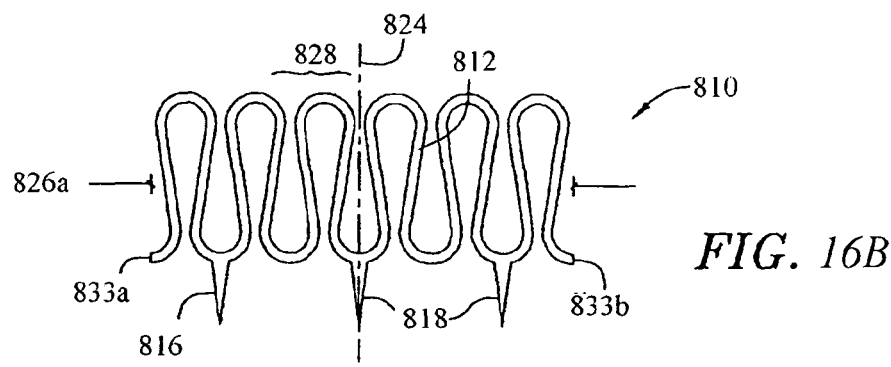
FIGS. 16B and 16C illustrate side views of the clip of FIG. 16A, with the tines oriented substantially transversely from the planar orientation, in compressed and expanded states, respectively.
Figure 16C:
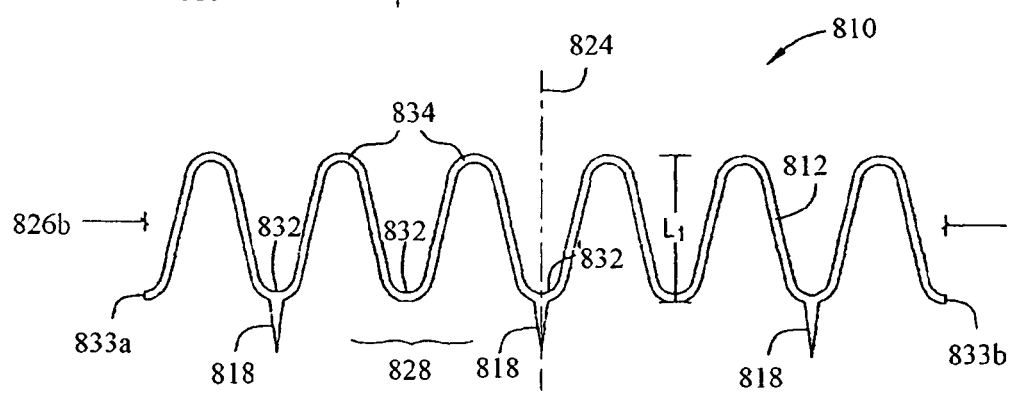

Turning now to the drawings, FIGS. 16A-16C show another embodiment of a closure device or clip 810 for closing an incision, puncture, or other passage through tissue, e.g., communicating with a blood vessel or other body lumen (not shown). The clip 810 includes a body 812, which may be generally annular in shape and surrounds a central axis 824, and a plurality of tines 818 extending from the body 812. As used herein, an "annular-shaped body" includes any hollow body, e.g., including one or more structures surrounding an opening, whether the body is substantially flat or has a significant thickness or depth. Thus, although an annular-shaped body may be circular, it may include other noncircular shapes as well, such as elliptical or other shapes that are asymmetrical about a central axis.

The body 812 may include a plurality of looped or curved elements 828 that are connected to one another to form the body 812. Each looped element 828 may include an inner or first curved region 832 and an outer or second curved region 34. In another embodiment, the first and second curved regions 832, 834 are out of phase with one another and are connected alternately to one another, thereby defining an endless sinusoidal pattern. Alternatively, other generally zigzag patterns may be provided that repeat periodically, e.g., saw tooth or square tooth patterns (not shown), instead of a sinusoidal pattern, thereby defining inner and outer regions that alternate about the body 812. When the clip 810 is in a substantially planar configuration, as shown in FIG. 16A, the first curved regions 832 may define an inner periphery 836 of the body 812 and the clip 810, and the second curved regions 834 may define an outer periphery 838.

The plurality of tines 818 may be biased to extend generally inwardly, e.g., towards one another and/or towards the central axis 824. The tines 818 may be disposed on the first curved regions 832, and oriented toward the central axis 824 when the clip 810 is in the planar configuration. In another embodiment, the tines 818 may be provided in pairs opposite from one another or provided otherwise symmetrically with respect to the central axis 824.

The tines 818 may include a variety of pointed tips, such as a bayonet tip, and/or may include barbs (not shown) for penetrating or otherwise engaging tissue. For example, to increase the penetration ability of the clip 810 and/or to lower the insertion force required to penetrate tissue, each tine 818 may include a tapered edge (not shown) extending towards the tip along one side of the tine 818. Alternatively, each tine 818 may be provided with a tapered edge on each side of the tine 818 extending towards the tip.

Additionally, as shown in FIGS. 16A-16C, the tines 818 may be disposed on alternating first curved regions 832. Thus, at least one period of a zigzag pattern may be disposed between adjacent tines 818, which may enhance flexibility of the clip 810, as explained further below.

As shown in FIGS. 16B and 16C (where opposite ends 833a, 833b are connected to one another), the body 812 and/or the tines 818 may be deflected such that the tines 818 extend transversely with respect to the plane defined in the planar configuration, thereby defining a transverse configuration for the clip 810. The tines 818 can be oriented substantially parallel to the central axis 824 in the transverse configuration, as shown in FIG. 16B. In the transverse configuration, the body 812 may have a generally annular shape defining a length, $L_1$, which extends generally parallel to the central axis 824, and corresponds generally to an amplitude of the zigzag pattern. The body 812 can be sufficiently flexible such that the clip 810 may assume a generally circular or elliptical shape (not shown), e.g., conforming to an exterior surface of a delivery device (not shown) used to deliver the clip 810.

In another embodiment, the tines 818 and/or body 812 are biased to move from the transverse configuration towards the planar configuration of FIG. 16A. Thus, with the tines 818 in the transverse configuration, the tines 818 may penetrate and/or be engaged with tissue at a puncture site. When the clip 810 is released, the tines 818 may attempt to return towards one another as the clip 810 moves towards the planar configuration, thereby drawing the engaged tissue together and substantially closing and/or sealing the puncture site, as explained further below.

The looped elements 828 may distribute stresses in the clip 810 as it is deformed between the planar and transverse configurations, thereby minimizing localized stresses that may otherwise plastically deform, break, or otherwise damage the clip 810 during delivery. In addition, when the clip 810 is in the transverse configuration, the looped elements 828 may be movable between a compressed state, such as that shown in FIG. 16B, and an expanded state, such as that shown in FIG. 16C. The looped elements 828 can be biased towards the expanded state, but may be compressed to the compressed state, e.g., by constraining the clip 810. Alternatively, only a portion of the looped elements 828 may be biased towards the expanded state, e.g., the first curved regions 832, and/or the looped elements 828 may be biased towards the compressed state. Furthermore, the looped elements 828 reduce the force required to be exerted on the clip 810 to transition the clip 810 from the planar configuration to the transverse configuration before loading onto a delivery device (not shown).

With the clip 810 in the transverse configuration, the looped elements 828 may be circumferentially and/or radially compressed to the compressed state until the clip 810 defines a first diameter or circumference 826a, such as that shown in FIG. 16B. The clip 810 may be constrained in the compressed state, e.g., by loading the clip 10 onto a carrier assembly of a delivery device (not shown), as described further below. When released from the constraint, e.g., when deployed from the carrier assembly, the clip 810 may automatically expand towards the expanded state, such as that shown in FIG. 16C, thereby defining a second diameter or circumference 826b. Thus, the looped elements 828 may facilitate reducing the profile of the clip 810 during delivery, e.g., to facilitate introducing the clip 10 through a smaller puncture or passage. Once the clip 810 is deployed entirely from the delivery device, the looped elements 828 may resiliently expand as the clip 810 returns towards the planar configuration, as explained further below.

To manufacture the clip 810 (or, similarly, any of the other clips described herein), the body 812 and the tines 818 may be integrally formed from a single sheet of material, e.g., a superelastic alloy, such as a nickel-titanium alloy ("Nitinol"). Portions of the sheet may be removed using conventional methods, such as laser cutting, chemical etching, photo chemical etching, stamping, using an electrical discharge machine (EDM), and the like, to form the clip. The tines 818 may be sharpened to a point, i.e., tips may be formed on the tines 818 using conventional methods, such as chemical etching, mechanical grinding, and the like.

The clip 810 may be polished to a desired finish using conventional methods, such as electro-polishing, chemical etching, tumbling, sandblasting, sanding, and the like. Polishing may perform various functions depending on the method used to form the clip 810. For a clip formed by laser cutting or using an EDM, polishing may remove heat affected zones (HAZ) and/or burrs from the clip. For a clip formed by photo chemical etching, polishing may create a smoother surface finish. For a clip formed by stamping, polishing may remove or reduce burrs from the bottom side of the clip, and/or may smooth the "roll" that may result on the topside of the clip from the stamping process.

In addition or alternatively, the clip 810 may be formed from a shape memory alloy, e.g., Nitinol, with the looped elements 828 formed initially in the compressed state and/or the clip 810 in the planar configuration. With the clip 810 deformed to the transverse configuration, the clip 810 may be expanded, e.g., by applying a force radially outwards against an inner surface of the clip 810, thereby expanding the looped elements 30 to the expanded state. The looped elements 828 may then be heat treated, e.g., by heating the clip 10 to an austenitic state, to cause the looped elements 828 to "remember" the expanded state, as is known to those skilled in the art. It may also be necessary to further heat treat the clip 810 further, e.g., with the tines in the planar configuration to cause the body 812 and/or tines 818 to "remember" and be biased towards the planar configuration, as is known to those skilled in the art. The clip 810 may then be cooled, e.g., to a martensitic state, which may be at or close to ambient temperature, and manipulated, e.g., malleably deformed to the transverse configuration, for example, by loading the clip 810 onto a delivery device (not shown), as described below. Thus, if the clip 810 is subsequently heated to a predetermined temperature, e.g., at or below body temperature, the material may remember the planar configuration and/or expanded state and become biased towards them.

Figure 17A:
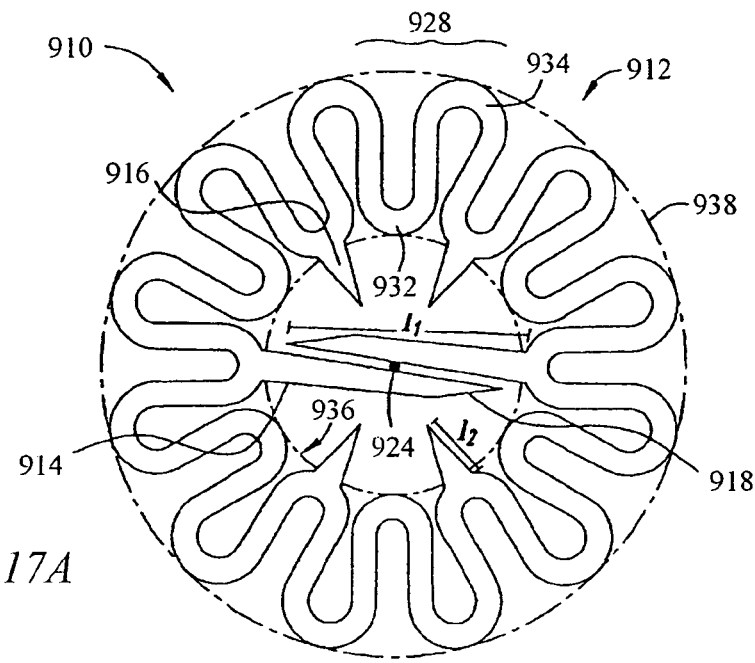
FIG. 17A illustrates a top view of yet another embodiment of a clip including a plurality of tines in a planar orientation, in accordance with the present invention.
Figure 17B:
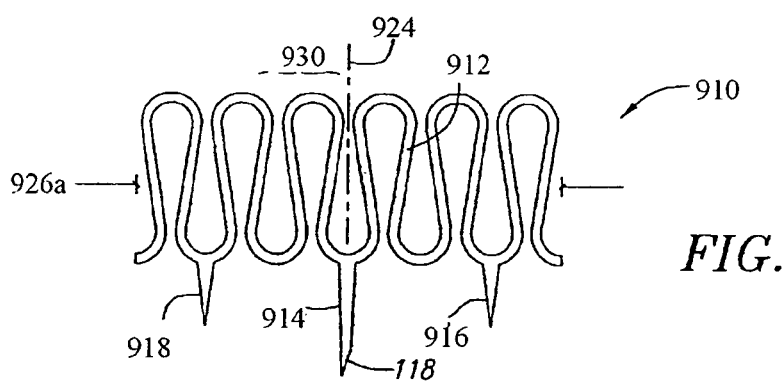
FIGS. 17B and 17C illustrate side views of the clip of FIG. 17A, with the tines oriented substantially transversely from the planar orientation, in compressed and expanded states, respectively.
Figure 17C:
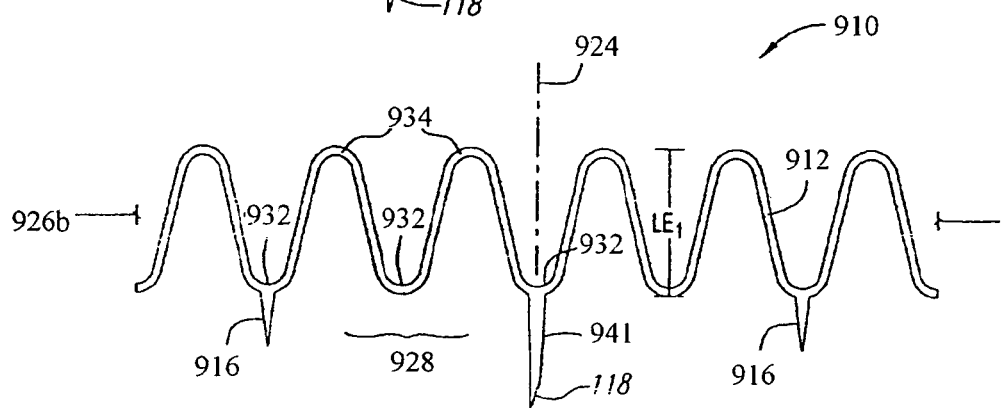

FIGS. 17A-17C show another embodiment of a closure device or clip 910 that includes a generally annular-shaped body 912 defining a plane and disposed about a central axis 9124 extending through the plane. The body 912 can include a plurality of looped elements 928 that are connected to one another to form the body 912, similar to the previous embodiment. Each looped element 928 includes an inner or first curved region 932 and an outer or second curved region 934. Similar to the previous embodiment, the first and second curved regions 932, 934 may form an endless sinusoidal pattern or other generally zigzag pattern. When the clip 910 is in a substantially planar configuration, as shown in FIG. 17A, the first curved regions 932 may define an inner periphery 936, and the second curved regions 934 may define an outer periphery.

Unlike the previous embodiment, the clip 910 includes a plurality of primary tines 916 and a plurality of secondary tines 918. Each of the primary and secondary tines 916, 918 may include a variety of known pointed tips, similar to the previous embodiment.

Each of the primary tines 914 may have a length $l_1$, although alternatively each of the primary tines 914 may have a different length than one another. The primary tines 914 may be disposed in one or more opposing pairs, e.g., on opposing first curved regions 932, and may be oriented towards and/or across the central axis 924 in the planar configuration. In the planar configuration, the lengths $l_1$ may be sufficiently long such that the primary tines 914 at least partially overlap one another, i.e., extend across the central axis 924 towards an opposing tine 914. Therefore, the tips of the primary tines 914 may extend past the central axis 924 and/or the primary tines 914 in each pair may lie substantially parallel to each other when the clip 910 is in the planar configuration.

Each of the secondary tines 916 may be disposed on a first or inner curved region 932, e.g., such that one or more secondary tines 916 may be provided between opposing pairs of primary tines 914. Each of the secondary tines 916 may have a length 1.sub.2 that is substantially less than the length $l_1$ of the primary tines 914.

A secondary tine 916 can be is disposed on either side of each primary tine 914. For example, the clip 910 shown in FIGS. 17A-17C has first and second primary tines 914, and each of the first and second primary tines 914 has a secondary tine 916 on either side of it. Thus, the clip 910 may have a total of two primary tines 914 and four secondary tines 916. Optionally, the secondary tines 916 may be disposed substantially symmetrically about the central axis 924. The tines 914, 916 may be provided on every other first curved regions 932. For example, a first curved region 932 having neither a primary tine 914 nor a secondary tine 916 may separate each adjacent tine, e.g., between two adjacent secondary tines 916, or between a secondary tine 916 and a primary tine 914.

As shown in FIGS. 17B and 17C, the body 912 and/or the tines 914, 916 may be deflected such that they extend transversely with respect to the plane defined in FIG. 17A. The primary tines 914 and secondary tines 916 can be oriented substantially parallel to the central axis 924 to define a transverse configuration, as shown in FIG. 16B. In the transverse configuration, the body 912 has a generally annular shape defining a length, $LE_1$, which extends generally parallel to the central axis 924, and corresponds generally to an amplitude of the sinusoidal pattern. The body 912 can be sufficiently flexible such that the clip 910 may assume a generally circular or elliptical shape (not shown), e.g., conforming to an exterior surface of a delivery device (not shown).

The tines 914, 916 may be biased towards one another and/or towards the central axis 924, i.e., due to the bias of the clip 910 towards the planar configuration of FIG. 17A, similar to the previous embodiment. With the clip 910 in the transverse configuration, the clip 910 may be delivered such that the primary tines 914 entirely penetrate the wall of a blood vessel or other body lumen, while the secondary tines 916 only partially penetrate the wall due to their relative lengths, as explained further below.

The looped elements 928 may be expandable between a compressed state, as shown in FIG. 17B, and an expanded state, as shown in FIG. 17C, similar to the previous embodiment. The looped elements 928 can be biased to the expanded state, but may be resiliently compressed to the compressed state, e.g., by constraining the clip 910.

Figure 18:
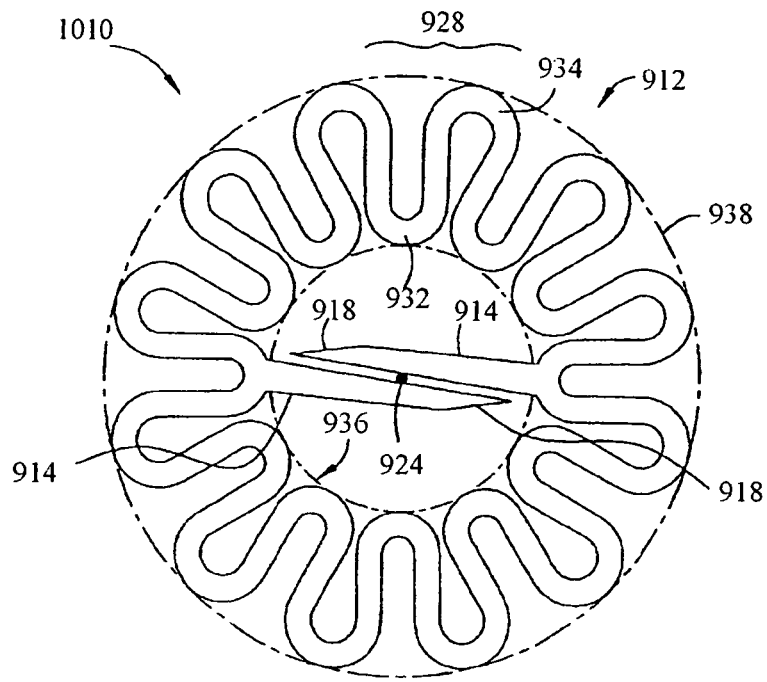
FIG. 18 illustrates a top view of another embodiment of a clip, in accordance with the present invention.

Turning to FIG. 18, an alternative embodiment of a clip 1010 is shown that includes a body 912 including looped elements 930, and primary tines 914, similar to the previous embodiment, but has no supplemental or secondary tines 916. The reference numbers for elements of the clip 1010 are consistent with like elements used for the clip 910.

Any of the clips of the present invention may include one or more radiopaque markers or other markers visible using external imaging, such as fluoroscopy. For example, using the clip 910 of FIGS. 17A-17C as an example, the entire clip 910 may be coated with radiopaque material, which may be a high density material such as gold, platinum, platinum/iridium, and the like.

Alternatively, the clip 910 may be partially coated with radiopaque material by using masking techniques. For example, the entire clip 910 may first be coated with radiopaque material. The clip 910 may then be masked at locations where the radiopaque coating is desired. For example, the looped elements 928 of the clip 910 may be left unmasked during this process if it is desired to leave the looped elements 928 uncoated by radiopaque material. This may be desirable, e.g., to prevent radiopaque material from adversely affecting the flexibility of the looped elements 928. The clip 910 may then be treated to remove the radiopaque material from the unmasked areas, in this example, the looped elements 928. The masking may then be removed using conventional processes, leaving the rest of the clip 910 coated with radiopaque material.

Figure 19:
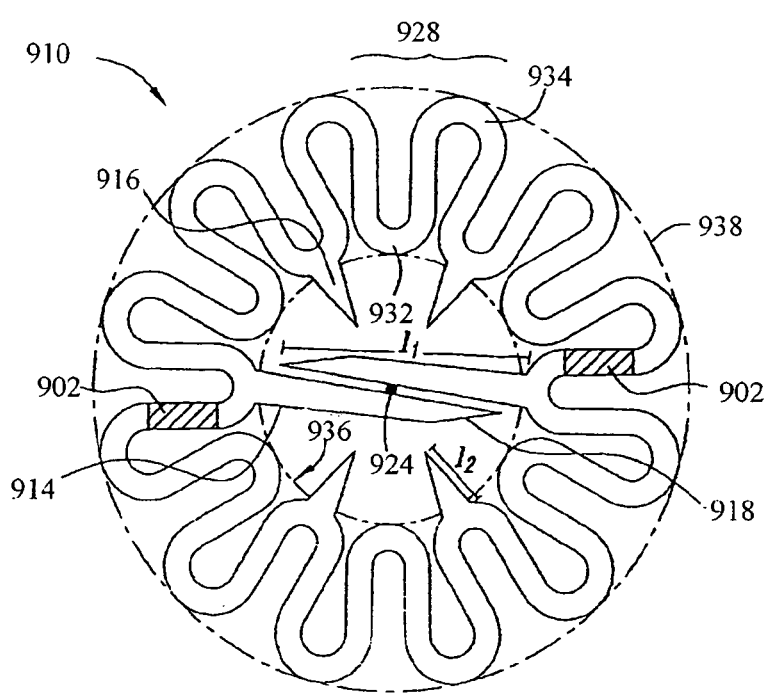
FIG. 19 illustrates a top view of an embodiment of a clip having radiopaque markers thereon.
Figure 20:
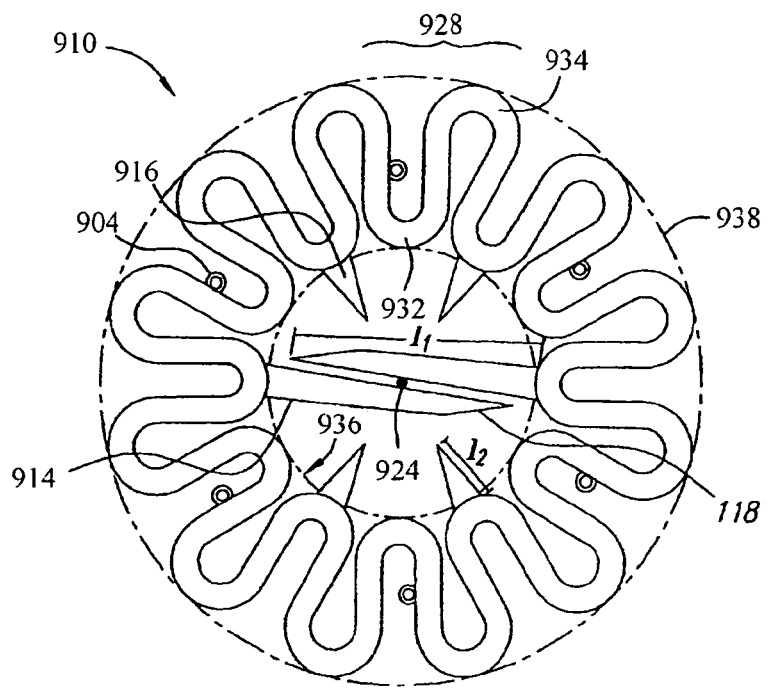
FIG. 20 illustrates a top view of an embodiment of a clip having pockets for holding radiopaque markers therein.

Turning to FIG. 19, in another alternative, one or more discrete markers 902 may be provided at predetermined locations on the clip 910. For example, high density or radiopaque material 902 may be crimped or otherwise secured onto opposing double looped or circular regions 928. In another embodiment, shown in FIG. 20, a plurality of pockets 904 may be provided on the looped elements 928 into which high density plugs (not shown) may be bonded or otherwise secured. These various radiopaque markers may also be incorporated in any of the embodiments described herein.

Figure 21:
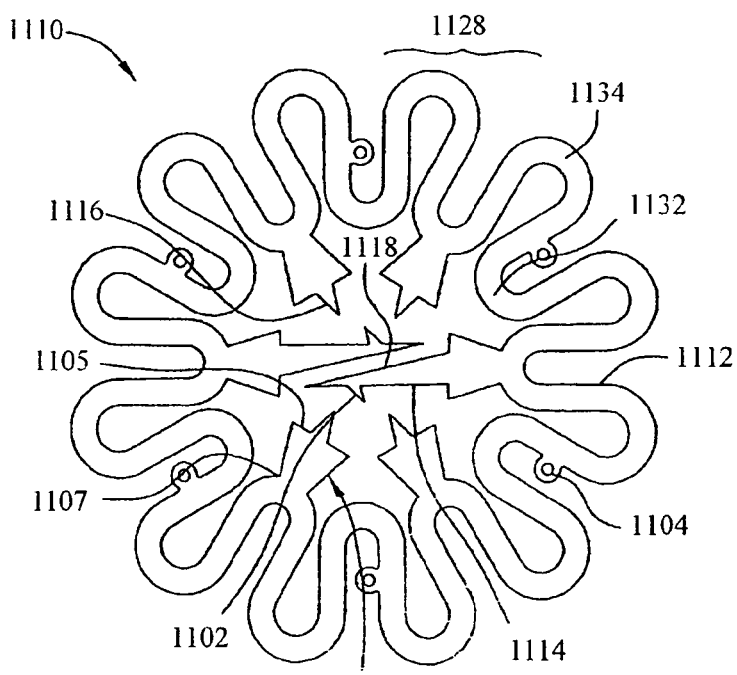
FIG. 21 illustrates a top view of another embodiment of a clip including stop elements, in accordance with the present invention.

Turning to FIG. 21, another embodiment of a clip 1110 is shown that, similar to clip 910, may include a plurality of looped elements 1128 that interconnect to form a body 1112. Each looped element 1128 may have a first or inner curved region 1132 and a second or outer curved region 1134. Primary tines 1114 may be disposed on opposing first curved regions 1132, which, optionally, may include a barb 1102 thereon to enhance engagement with tissue. Secondary tines 1116 may be provided on first curved regions 1132 on either side of each primary tine 1114. In addition, a first curved region 1132 without a tine 1114, 1116 may separate adjacent tines, as described above with regard to the previous embodiments.

The clip 1110 also includes stop members 1106 on one or more of the tines 1114, 1116, e.g., adjacent the respective first curved region 1132. Each stop member 1106 may be blunt-shaped, e.g., generally triangularly with an apex 1107 of the stop member 1106 extending from the first curved region 1132, and the tine 1114, 1116 extending from a wide or blunt base 1107 of the stop member 1106. During use, the blunt bases 1107 may limit penetration of the respective tines 1114, 1116 into tissue by reducing an effective length of the respective tine 1114, 1116. For example, when the tines 1114, 1116 are driven into tissue, the tines 1114, 1116 may penetrate the tissue until the blunt bases 1107 contact the tissue, whereupon the tines 1114, 1116 may be prevented from penetrating further into the tissue.

Figure 22:
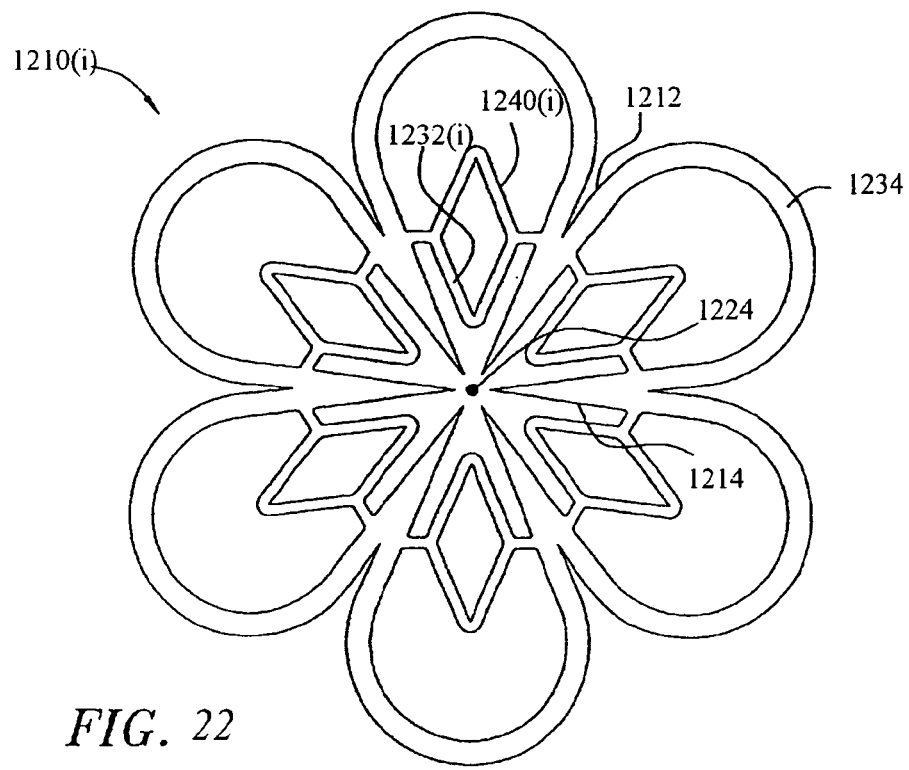
FIG. 22 illustrates a top view of yet another embodiment of a clip including stop elements, in accordance with the present invention.

Turning to FIG. 22, another embodiment of a clip 1210(i) is shown that includes a body 1212, a plurality of tines 1214, and a plurality of spring elements 1240(i) that interconnect between adjacent tines 1214. The body 1212 includes outer curved regions 1234 that extend between adjacent tines 414, thereby defining an outer periphery for the clip 1210(i). The clip 1210(i) may be moveable between a substantially planar configuration such as that shown in FIG. 22, and a transverse configuration (not shown), and can be biased towards the planar configuration, similar to the previous embodiments.

In the embodiment shown, the spring elements 1240(i) generally are hollow diamond shaped elements, including curved inner regions 1232(i) oriented towards the central axis 1224 of the body 1212 when the clip 1210(i) is in the planar configuration. The spring elements 1240(i) may serve multiple purposes. First, the spring elements 1240(i) may bias the clip 1210(i), e.g., allowing the clip 410(i) to at least partially expand resiliently. For example, when the clip 1210(i) is deflected into the transverse configuration (not shown), the spring elements 1240(i) may allow the tines 1214 to be moved away from the central axis 1224 and/or one another. Thus, during deployment, the tines 1214 may be deflected radially outwardly or otherwise expanded to engage a larger area of tissue.

As the tines 414 are expanded, the spring elements 1214(i) may deform to become wider (along a dimension extending generally between the adjacent tines 1214) and shorter (along a dimension extending generally parallel to the tines 1214). Once a force causing the tines 1214 to expand is removed, the spring elements 1214(i) may resiliently try to return towards their original shape, thereby pulling the tines 1214 closer towards one another.

In addition, the curved inner regions 1232(i) of the spring elements 1214(i) may provide stops limiting penetration of the tines 1214 into tissue, similar to the stop members described above. For example, when the clip 1210(i) is in the transverse configuration and the spring elements 1214(i) are expanded, the curved inner regions 1232(i) may be become more oblique, possibly becoming generally linear. Thus, when the tines 1214 are driven into tissue, the curved inner regions 1232(i) may limit penetration of the tines 1214.

Finally, after the clip 1210(i) is deployed, e.g., the tines 1214 are penetrated into tissue, the curved inner regions 1232(i) may return towards their original shape, and may pinch or otherwise engage tissue between the inner curved regions 1232(i) and the adjacent tines 1214. Thus, contracting the spring elements 1240(i) may enhance the ability of the clip 1210(i) to seal a puncture site, e.g., by pulling engaged tissue inwardly towards the central axis 1224 of the clip 1210(i).

Figure 23:
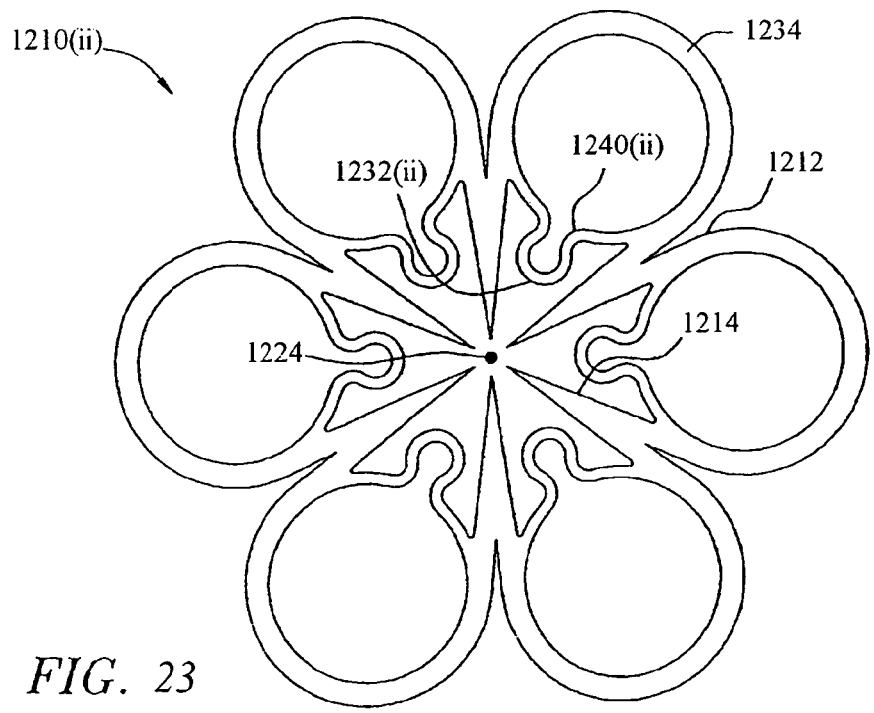
FIG. 23 illustrates a top view of still another embodiment of a clip including stop elements, in accordance with the present invention.

Turning to FIG. 23, an alternative embodiment of a clip 1210(ii) is shown that is substantially similar to the clip 1210(i) shown in FIG. 22, with the exception of the shape of the spring elements 1240(ii). Rather than diamond shaped elements, the spring elements 1240(ii) are looped elements generally defining a circular shape.

Figure 27:
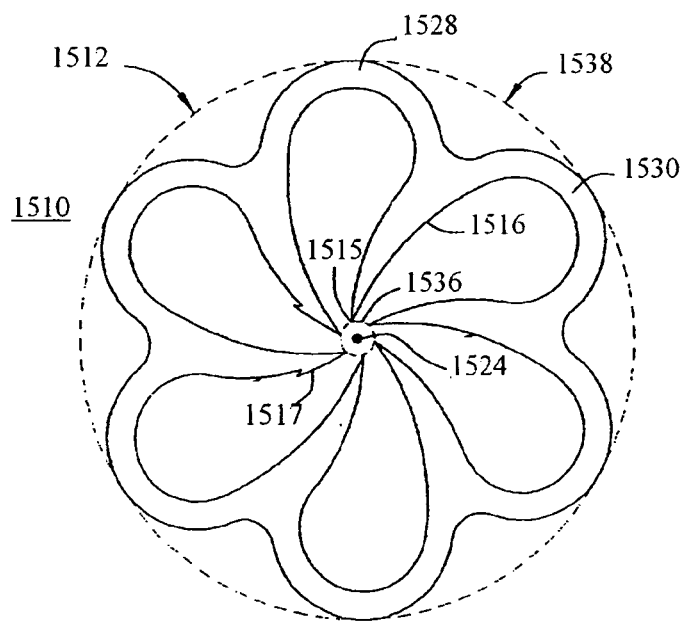
FIG. 27 illustrates a top view of an embodiment of a clip having arcuate tines, in accordance with the present invention.

Turning now to FIG. 27, another embodiment of a clip 1510 of the present invention is illustrated. Similar to the previous embodiments, the clip 1510 includes a generally annular-shaped body 1512 that defines a plane. The body 1512 is disposed about a central axis 1524 that extends through the plane. The body 1512 can include a plurality of outer curved elements 1528 that extend between adjacent tines 1516 and are connected to each other to form the body 1512. When the clip 1510 is in a substantially planar configuration, as shown in FIG. 27, the curved elements 1528 define an outer periphery 1538 of the clip 1510.

The tines 1516 are curved or arcuately shaped and include distal tips 1515 that extend toward the central axis 1524 when the clip 1510 is in the substantially planar configuration. Optionally, one or more of the tines 1516 may include barbs 1517, similar to the previous embodiments. The curve of the tines 1516 can all be in phase with one another such that the tines 1516 spiral about the central axis 1524. This may allow a length of the tines 1516 to be maximized for a given diameter of the body 1512.

For example, the tines 1516 may have a length that is greater than a radius of the body 1512 without the distal tips 1515 of the tines 1516 touching one another. Thus, due to the arcuate shape of each tine 1516, the tines 1516 of clip 1510 may be generally longer than the straight tines of the previous clips having comparable diameters. The tines 1516 may, therefore, penetrate deeper into tissue than the tines of the other clips.

As with the previous embodiments, the body 1512 and/or the tines 1516 of clip 1510 may be deflected until the tines 1516 extend transversely with respect to the plane defined in the planar configuration, thereby defining a transverse configuration. In the transverse configuration, the tines 1516 may be oriented substantially parallel to the central axis 1524. Additionally, as with the previous embodiments, the tines 1516 and/or body 1512 may be biased to move from the transverse configuration towards the planar configuration. The clip 1510 may be delivered in substantially the same manner as will be described with respect to other clips of the present invention.

Any of the clips of the present invention may be coated with a substance that enhances hemostasis and/or healing of a blood vessel, e.g., by increasing a rate of regeneration of endothelium on the interior surface of the vessel, or by decreasing inflammatory response at the treatment site. In one embodiment, a suitable synthetic peptide coating may be applied to a clip to attract endothelial cells to the surface. An exemplary synthetic peptide coating may, for example, attach to the same cell binding sites as collagen. In another embodiment, a clip may be coated with a combination of clotting factors in order to promote hemostasis. For example, one side of the clip may be coated with Factor III and an endopeptidase, such as PTA, to accelerate the intrinsic clotting pathway. On the opposite side of the clip, a combination of a protein cofactor proaccelerin (Factor V) and an activated endopeptidase, such as serum prothrombin conversion accelerator (SPCA), cothromboplastin, and the like, may be applied to accelerate the extrinsic clotting pathway. The clips of the present invention may also be coated with any suitable hydrophilic polymer that swells in the presence of bodily fluids in order to reduce, minimize, or stop blood flow, thereby aiding the hemostasis process.

Figure 24:
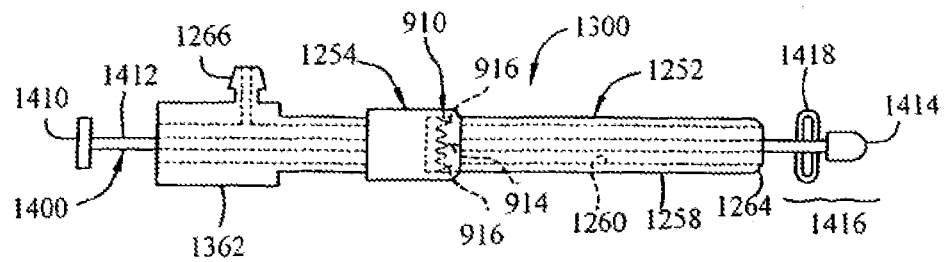
FIG. 24 illustrates a side view of an apparatus, including an introducer sheath and an obturator, suitable for delivering a clip of the present invention.

The clips of the present invention may be delivered using various apparatus and methods. An exemplary apparatus 1300 suitable for delivering a clip of the present invention is shown in FIG. 24. Other suitable apparatus that may be used to deliver a clip of the present invention are disclosed in U.S. Pat. No. 6,942,674, which is assigned to the assignee of the present application, the disclosures of which, and any references therein, are incorporated herein in their entirety by this reference.

Generally, the apparatus 1300 includes an introducer sheath 1352, and a housing or carrier assembly 1354 slidably disposed on the sheath 1352. The sheath 1352 includes a substantially flexible or semi-rigid tubular body 1358 including a lumen 1360 extending between its proximal and distal ends 1362, 1364. The distal end 1364 has a size and shape configured to facilitate insertion into a blood vessel, e.g., having a tapered tip for facilitating substantially atraumatic introduction through the passage and at least partially into the vessel. The lumen 1360 has a size for inserting one or more devices therethrough, such as a catheter, guidewire, and the like (not shown). The sheath 1352 also can include one or more seals (not shown), such as a hemostatic valve, within the lumen 1360 at or near the proximal end 1362 that provides a fluid-tight seal, yet accommodates inserting one or more devices into the lumen 1360 without fluid passing proximally from the sheath 1352.

Optionally, the sheath 1352 may include a side port 1366 that communicates with the lumen 1360, for example, to deliver fluids into the lumen 1360. Alternatively, or in addition, the side port 1366 may be used to provide a "bleed back" indicator. An exemplary "bleed back" indicator and related methods of use are disclosed in U.S. Pat. No. 6,626,918, which is assigned to the assignee of the present application, the disclosures of which, and any references therein, are incorporated herein in their entirety by this reference.

The apparatus 1300 may also include a mechanical locator or obturator 1400, such as that disclosed in U.S. application Ser. No. 10/081,723, now U.S. Pat. No. 6,942,674, the disclosures of which, and any references therein, are incorporated herein in their entirety by this reference, that may be part of an actuator assembly that is attachable to the proximal end of the sheath 1352. Alternatively, the mechanical locator or obturator 1400 may be a separate device that is insertable into the lumen 1360, e.g., through the actuator assembly. Generally, the obturator 1400 is an elongate member including a distal tip 1414 and a distal portion 1416. The distal tip 1414 may be substantially soft and/or flexible such that the distal tip 1414 may substantially atraumatically enter the vessel 1390 (not shown, see FIGS. 25A-25D). The distal portion 1416 generally includes one or more wings or other expandable elements 1418 for providing tactile feedback, as described further below.

The carrier assembly 1354 is slidably disposed on an exterior of the sheath 1352, and is configured for releasably carrying a clip 910 (shown in phantom), which may any of the clips described herein. The carrier assembly 1354 may be substantially permanently attached to the sheath 1352 and/or may be actuated from the proximal end 1362 of the sheath 1352, for example, by the actuator assembly (not shown), to advance the clip 910 distally during deployment. Alternatively, the clip 910 may be carried by an actuator assembly, as disclosed in co-pending U.S. application Ser. No. 10/081,725, now U.S. Pat. No. 6,749,621, filed on the same day as the present application and entitled "Sheath Apparatus and Methods for Delivering a Closure Device," which is assigned to the assignee of the present application, the disclosures of which, and any references therein, are incorporated herein in their entirety by this reference.

Turning to FIGS. 25A-D, the apparatus 1300 may be used to deliver the clip 910 to close and/or seal an incision, puncture, or other passage 1392 that extends from a patient's skin 1394, through intervening tissue 1396, and into a wall 1398 of a vessel 1390 or other body lumen. Alternatively, the apparatus 1300 may be used to deliver the clip 910 to engage tissue in other procedures, e.g., to connect tissue segments together or otherwise to secure tissue structures with respect to one another. For example, the apparatus 1300 and clip 910 may be used to attach an anastomosis during a bypass procedure. It will be appreciated by those skilled in the art that the clip 910 and/or apparatus 1300 may be useful in a variety of procedures.

Figure 25A:
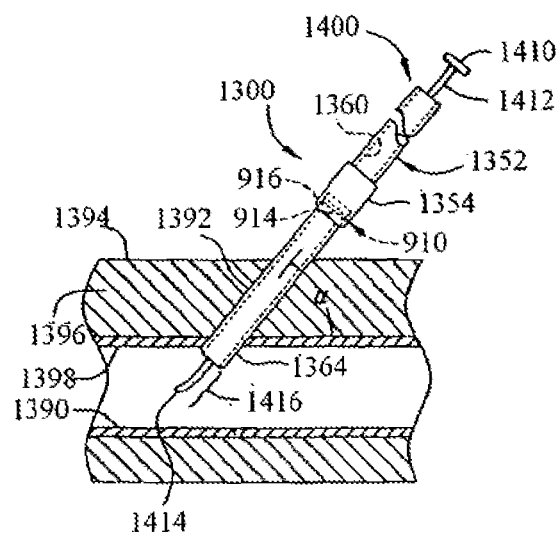
FIGS. 25A-25D illustrate cross-sectional views of a blood vessel, showing a method for delivering a clip into a passage communicating with the vessel using the apparatus of FIG. 24.

As shown in FIG. 25A, the sheath 1352 may be inserted or otherwise positioned within the vessel 1390, i.e., through the passage 1392. The sheath 1352 may be advanced over a guidewire or other rail (not shown) previously positioned through the passage 1392 into the vessel 1390 or advanced in conjunction with a pointed stylet directly through tissue using conventional procedures. The vessel 1390 can be a peripheral vessel, such as a femoral, radial, or carotid artery, although other body lumens may be accessed using the sheath 1352, as will be appreciated by those skilled in the art.

The passage 1392, and consequently the sheath 1352, may be oriented at an angle "alpha" with respect to the vessel 1390, thereby facilitating introducing devices through the lumen 1360 of the sheath 1352 into the vessel 1390 with minimal risk of damage to the vessel 1390. One or more devices, such as a guide wire, a catheter, and the like (not shown), may be inserted through the sheath 1352 and advanced to a desired location within the patient's body. For example, the devices may be used to perform a therapeutic or diagnostic procedure, such as angioplasty, atherectomy, stent implantation, and the like, within the patient's vasculature.

After the procedure is complete, any devices used during the procedure may be removed from the sheath 1352, and the obturator 1400 may be inserted into the lumen 1360. For example, the obturator 1400 may be part of an actuator assembly (not shown), and may be advanced through the lumen when the actuator assembly is attached to the proximal end of the sheath 1352. Alternatively, the actuator assembly and obturator 1400 may be coupled separately to the sheath 1352.

When the obturator 1400 is fully inserted within the sheath 1352, the distal portion 1416 of the obturator 1400 may extend beyond the distal end 1364 of the sheath 1352. In an alternative embodiment, the obturator 1400 may be attached to an exterior surface (not shown) of the sheath 1352, for example, along a track, e.g., including cooperating slots, grooves, and the like (not shown) in the sheath 1352 and obturator 1400.

Figure 25B:
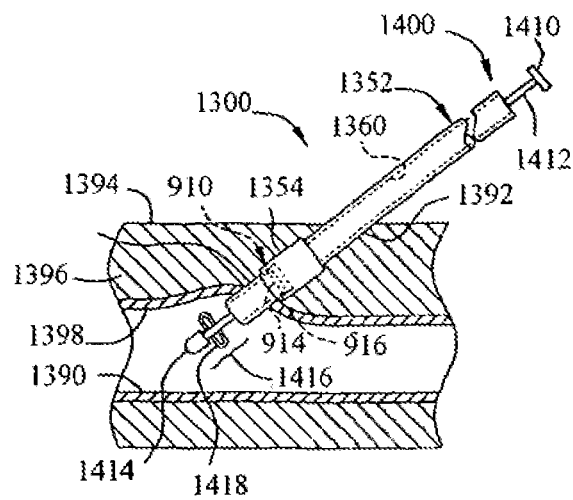

Turning to FIG. 25B, the expandable elements 1418 on the distal portion of the obturator 1400 may then be directed to their expanded configuration, for example, by activating a switch on the proximal end (not shown) of the obturator 1400. With the sheath 1352 and obturator 1400 coupled to one another, the sheath 1352 and obturator 1400 may be moved in conjunction with one another.

Figure 25C:
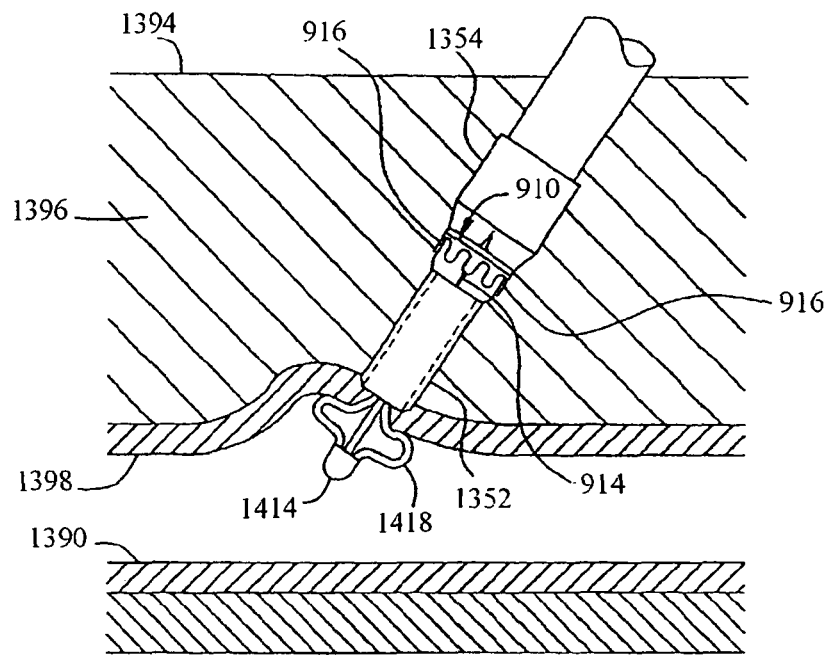

As shown in FIG. 25C, the sheath 1352 may be partially withdrawn from the vessel 1390, until the expandable elements 1418 contact the wall 1398 of the vessel 1390. Thus, the expandable elements 1418 may provide a tactile indication of the position of the sheath 1352 with respect to the wall 1398 of the vessel 1390. In addition, the expandable elements 1418 may assist in "presenting" the wall 1398 of the vessel 1390, e.g., for receiving the clip 910.

Generally, the clip 910 is carried by the carrier assembly 1354 before the procedure. The clip 910 may be constrained in its transverse configuration on the carrier assembly 1354, and the carrier assembly 1354 may be provided on or adjacent the proximal end of the sheath 1352. Because the tines, which may include primary and secondary tines 914, 916 may be biased towards one another, the tines 914, 916 may slidably contact an inner surface (not shown) of the carrier assembly 1354 or an outer surface of the sheath 1352, thereby constraining the clip 910 in its transverse configuration.

Figure 25D:
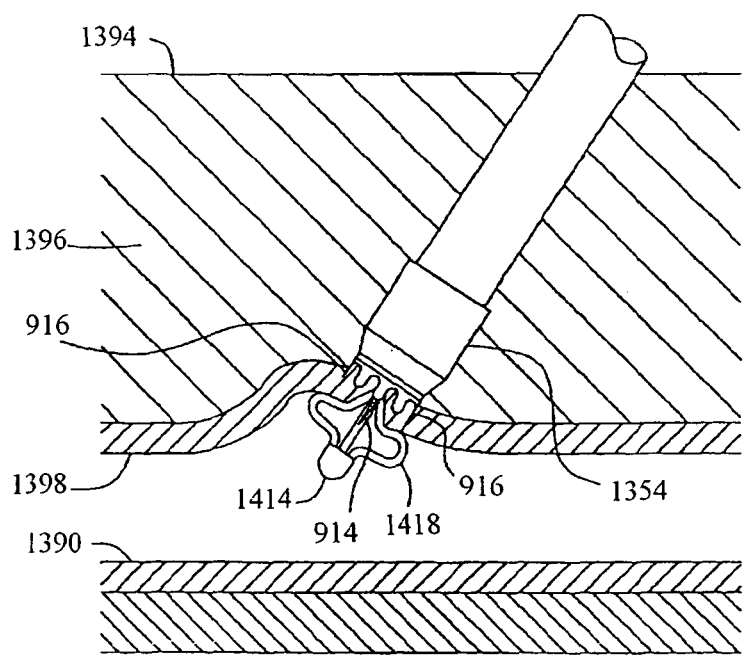

Turning to FIG. 25D, with the sheath 1352 properly positioned, the carrier assembly 1354 may then be actuated, for example, to advance the carrier assembly 1354 distally over the sheath 1352 to deliver the clip 910. The carrier assembly 1354 may only be advanced a predetermined fixed distance relative to the distal end of the sheath 1352, and consequently, the expandable elements 1418 of the obturator 1400, such that the clip 910 substantially engages the wall 1398 of the blood vessel 1390. This predetermined distance may facilitate properly deploying the clip 910 with respect to the wall 1398 of the vessel 1390, e.g., to prevent advancing the clip 910 too far, i.e., into the vessel 1390.

As the clip 910 is deployed from the carrier assembly 1354, the clip 910 may be expanded to an enlarged diameter. For example, a distal end of the carrier assembly 1354 may include a ramped region (not shown) that may deflect the tines 914, 916, and/or the body of the clip 910 radially outwardly. As the clip 910 is advanced over the ramped region, the tines 914, 916 may be deflected radially outwardly as they are being driven into the surrounding tissue, thereby engaging a larger region of tissue than if the tines 914, 916 had been maintained substantially axially.

Alternatively, the clip 910 may include expandable looped elements and/or spring elements (not shown), such as those described above, that may facilitate expanding the clip 910 as it is deployed from the carrier assembly 1354 and/or the sheath 1352. For example, the looped elements of the clip 910 may be compressed when the clip 910 is loaded into the carrier assembly 1354, e.g., thereby allowing a relatively smaller profile carrier assembly 1354 to be used. The clip 910 may automatically expand upon deployment from the carrier assembly 1354 to engage a larger region of tissue surrounding the opening, such as an arteriotomy 1391 in the wall 1398 of the vessel 1390 (see FIG. 26A).

Figure 26A:
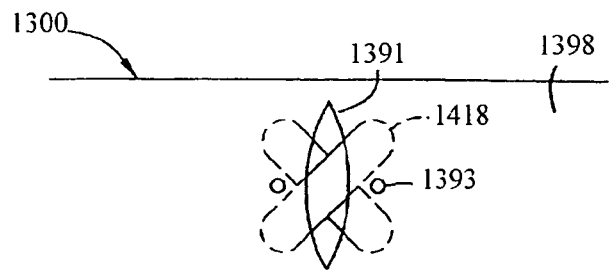
FIG. 26A illustrates a top view of the blood vessel of FIGS. 25A-25D, showing the orientation of the expandable elements of the obturator and openings produced by primary tines of the clip relative to an arteriotomy in the vessel.
Figure 26B:
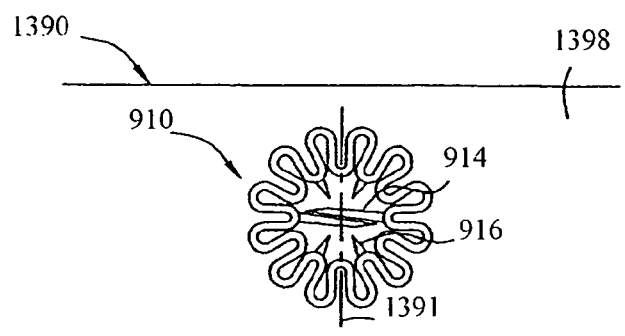
FIG. 26B illustrates Figure a top view of the blood vessel of FIG. 26A, showing the arteriotomy being closed by the clip.

Once the clip 910 is deployed entirely or otherwise released from the sheath 1352, the clip 910 may resiliently move towards its substantially planar configuration, such as that shown in FIG. 26B.

During delivery of the clip 910, radiopaque markers (not shown) on the clip 910, the carrier assembly 1354, and/or the expandable members 1418 may be monitored, e.g., using fluoroscopy, to facilitate observing and/or positioning the apparatus 1300. Thus, a relative position of the clip 910 with respect to the expandable elements 1418, and consequently to the wall 1398 of the vessel 1390, may be ascertained before the clip 910 is deployed from the carrier assembly 1354.

Turning to FIGS. 26A and 26B, in another embodiment, the expandable elements 1418 of the obturator 1400 may be rotationally offset from the one or more tines 914 on the clip 910. For example, if the clip 910 includes primary tines (such as those shown in FIGS. 17A and 18), the obturator 600 and clip 910 may have a predetermined relative angular orientation about the central axis 924. The clip 910 can be loaded onto the carrier assembly 1354 in a predetermined angular orientation and the obturator 600 is receivable in the sheath 1352 only in a predetermined angular orientation that is offset such that the tines 914, 916 are out of axial alignment with the expandable elements 1418, as shown in FIG. 26A.

This predetermined rotational orientation may substantially minimize the possibility of the primary tines 914 contacting and/or damaging the expandable elements 1418. For example, with particular reference to FIG. 26A, a relative angular orientation of the clip 910 and obturator 1400 is shown relative to an arteriotomy 591 in the wall 598 of the vessel 590. Here, the expandable elements 618 are oriented to crisscross diagonally the arteriotomy 591 within the interior of the vessel 590. Generally, because of the natural structure of the tissue in the wall of a vessel, an arteriotomy generally tends to adopt an elongate shape that extends transversely to the direction of flow (i.e., across the circumference of the vessel wall).

The primary tines 914 are oriented such that the primary tines 914 pierce the wall 1398 of the vessel 1390 on either side of the arteriotomy 1391, as shown. With the expandable elements 1418 crisscrossing diagonally, risk of contact with the primary tines 914 is substantially reduced. Thus, the primary tines 914 may be sufficiently long to extend entirely through the wall 1398 of the vessel 1390 while avoiding the expandable elements 618.

The expandable elements 1418 may then be collapsed and/or withdrawn into the distal end 1364 of the sheath 1352. As the clip 910 is released entirely from the sheath 1352, the primary tines 914 may partially overlap, as shown in FIG. 26B, thereby pulling the arteriotomy 1391 closed, similar to a single-thread suture. For example, the expandable elements 1418 may be automatically collapsed immediately before or after the clip 910 is deployed from the carrier assembly 1354 or when the carrier assembly 1354 reaches its extreme distal position. The distal portion 1416 of the obturator 1400 can be collapsed and retracted into the sheath 1354 after the primary tines 914 have pierced the wall 1398 of the vessel 1390, but before the clip 910 is entirely released from the sheath 1352.

In addition, if the clip 910 includes secondary tines 916 (such as those shown in FIG. 17A), the secondary tines 916 may partially penetrate the wall 1398 of the vessel 1390 during deployment of the clip 910. The lengths of the secondary tines 916 can be relatively short or stop members (not shown) may be provided that prevent the secondary tines 916 from piercing entirely through the wall 1398. When the clip 910 is released, the secondary tines 916 may pull the tissue inwardly, behaving somewhat similarly to a purse-string suture, to enhance closing the arteriotomy 1391.

Once the clip 910 is successfully deployed into the wall 1398 of the vessel 1390, e.g., on either side of an arteriotomy 1391, the apparatus 1300 may be withdrawn from the passage 1392. The entire apparatus 1300 may be removed in one step, or alternatively, the obturator 1400 may first be withdrawn from the sheath 1352 before withdrawing the sheath 1352, thereby leaving the clip 910 in place to close the arteriotomy 1391 and/or seal the passage 1392. In addition, if desired, a sealant or other material may be introduced into the passage 1392 in conjunction with or separate from delivery of the clip 910 to further seal the passage 1392, as is known to those skilled in the art.

According to another aspect, the clips described herein can be manufactured in various manners. These clips can be useful for engaging tissue so as to connect tissue segments together or to close and/or seal openings through tissue such as a puncture wound in a body lumen. These clips may be used by deforming them from their generally planar configuration such that the tines are pointing in a direction generally transverse to the plane, holding the clip in this deformed condition, deploying the clip proximal to the tissue to be engaged and removing the deforming force such that the clip engages the tissue and attempts to return to its original generally planar configuration. The methods and apparatus disclosed in the above-mentioned U.S. patent application Ser. Nos. 10/081,726 and 09/732,178, now U.S. Pat. Nos. 6,623,510 and 6,719,777 can be used to deploy the clips of the present invention to engage tissue and close or seal an opening.

In such use, the deformation of the clip causes the tines to be directed generally axially away from the body of the clip and it is the elastic property of the deformed clip which causes it to attempt to return to its original generally planar configuration. The body of the device may comprise a series of looped elements which generally define an endless zigzag pattern, e.g., a sinusoidal pattern, extending about a central access. The looped elements are believed to facilitate deforming the device between the planar and transverse configurations, e.g., by distributing stresses through the device and minimizing localized stresses in the curved regions.

Figure 28A:
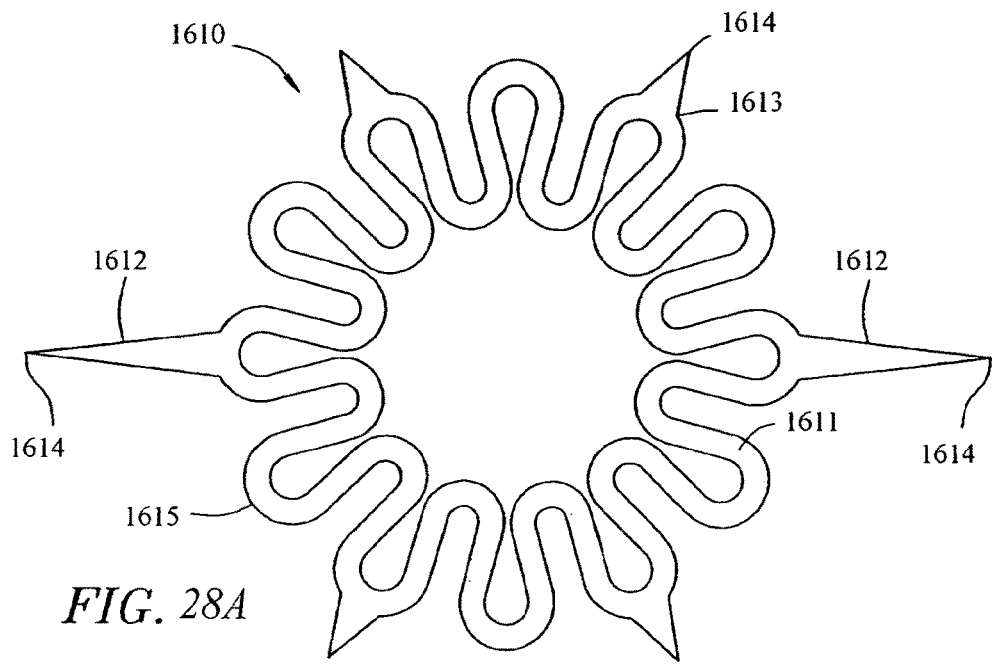
FIGS. 28A and 28B illustrate the before and after configuration of a clip manufactured according to one embodiment of this invention.

In another embodiment of the present invention, a clip precursor is first formed from a sheet of material, such as a superelastic alloy, such as a nickel-titanium alloy ("Nitinol") alloy. The property of superelasticity and of certain alloys which possess that property is disclosed in U.S. Pat. No. 4,665,906, the disclosures of which, and any references therein, are incorporated herein in their entirety by this reference. This forming can be done by removing portions of the material by cutting, chemical etching, laser cutting, photochemical etching, stamping, electrical discharge machining and the like to produce a precursor such as that shown in FIG. 28A which has radially outward extending tines. The precursor can then be polished using one or more processes such as electropolishing, tumbling, sand blasting, sanding and the like or such polishing can be done as a final step after the clip is formed. Forming of a precursor in this manner does not require working to tolerances as close as those which would be required if the clip was to be manufactured in its final configuration shown in FIG. 28B because the radially outwardly extending tines of the precursor shown in FIG. 28A are easily accessible by the forming tool whereas attempting to directly form the clip with radially inwardly extending tines which are closely spaced requires difficult high precision metal cutting. Thus, manufacture of a precursor which is then reconfigured to final clip shape permits the achievement of closer spacing between the elements of the final clip than would otherwise be achievable with conventional methods.

The precursor 1610 comprises a hoop-shaped planar body 1611 which has outwardly extending primary (longer) tines 1612 and secondary (shorter) tines 1613. For example, the primary trials may be 0.070 to 0.105 inches in length and the secondary tines may be 0.025 to 0.035 inches in length. Each of the tines terminates in a point 1614. When the precursor 1610 has been reconfigured into clip 1616 shown in FIG. 28B, the tines 1612 and 1613 become the tissue engaging portions of the clip. The tines may be sharpened or given a shape, e.g., barbs (not shown), while the device is in the precursor state. The body 1611 may compromise connecting links such as loops 1615. These links may have any suitable shape provided that such shape does not interfere with inversion of the precursor 1610.

The precursor 1610 is then inverted to reconfigure it into the shape of clip 1616. In this embodiment in which the precursor is formed from a sheet of nickel-titanium alloy, the inverted precursor is then heat set, e.g., by heating to a temperature of 510° C., and then quenched to cool to room temperature. The clip 1616 will now be in the austenitic state.

Heat setting and quenching are essential to successful practice of the invention with superelastic alloys. As explained in more detail in U.S. Pat. No. 4,665,906, the disclosures of which, and any references therein, are incorporated herein in their entirety by this reference, a superelastic alloy such as nickel-titanium exists in two states, the austenitic state and the martensitic state. Such alloys will initially be in the austenitic state, e.g., when the precursor is formed. However, when the precursor is inverted to take the shape of the final clip, the stress experienced by the alloy during the inversion will cause the alloy to be partially or wholly converted to the martensitic state. Such a martensitic state is commonly referred to as stress-induced martensite. Such martensite structure has the property of superelasticity and the inverted precursor would revert to its original shape if not held in the inverted configuration.

Figure 28B:
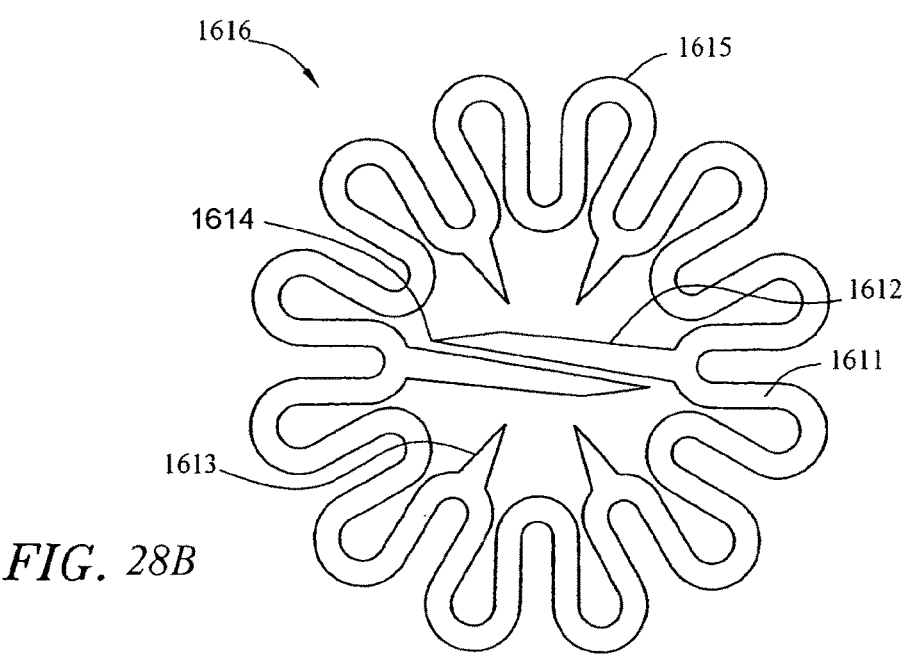

Since, if the inverted precursor was left in the martensitic state, it would want to elastically revert to its original uninverted state, it must be converted back to austenite. Thus, heating and quenching are required to convert the inverted precursor from the martensitic state to the austenitic state such that the clip is stable in its planar configuration as shown in FIG. 28B and will retain that configuration.

The times and temperatures for heat setting of superelastic alloys of various compositions can be determined from existing literature or can be determined empirically without any difficulty. The clips are small in size and the heating and quenching may be done with any conventional heating and quenching equipment. For example, once inverted, the inverted precursor can be held in that configuration and placed in a fixture which will hold it in the inverted configuration during heat setting.

Figure 31:
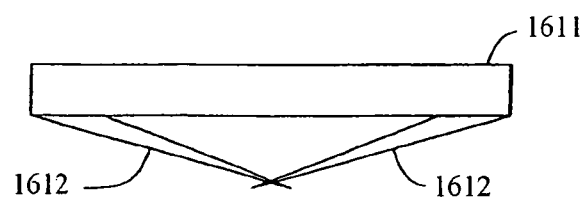
FIG. 31 illustrates a clip which, while generally planar, has tines which extend radially inwardly at an angle to the plane defined by the body.

When clips are manufactured according to the present invention, the space between the tines may actually be eliminated, i.e., after inverting the precursor, the tines may be in contact with each other, in either a side-by-side or an over-and-under relationship. The number, length and spacing of the tines may be varied according to the desires of the manufacturer. Furthermore, while use of a planar precursor is a convenience in manufacturing, a planar configuration is not required. For example, the precursor could be bent along a diameter or major or minor axis of the precursor and could be heat set in such a bent configuration. Alternatively, the clip, while generally planar, may have the tines extending at an acute angle to the plane defined by the body as shown in FIG. 31 in which the body 1611 and tines 1612 are shown. Furthermore, manufacturing from a sheet of material is a convenience, but other manufacturing techniques, including joining of components such as the tines to the body, can be accomplished by welding, brazing, or other known methods of joining materials. In such cases, one or more of such components may be circular in cross-section or tubular in configuration.

Still further, the clip need not be fabricated from a single material, e.g., the tines may be manufactured from a different material than the body. In such cases, a portion of the clip such as the tines may be bioabsorbable provided that the final clip is capable of elastic recovery after being deformed. An advantage of the present invention is that it permits the production of clips with tines that are 30 to 40% or more longer than those which could be made with prior direct cutting methods, because there is no limit on the length of the tine which is formed on the precursor. Thus, after the precursor is inverted, the tines may overlap the annular body.

Figure 29A:
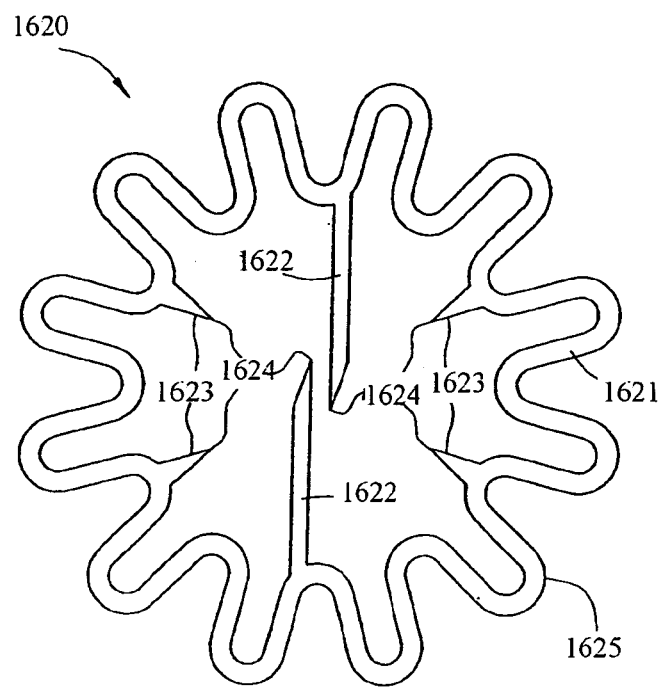
FIGS. 29A and 29B illustrate the before and after-configuration of a clip manufactured according to another embodiment of the invention.
Figure 29B:
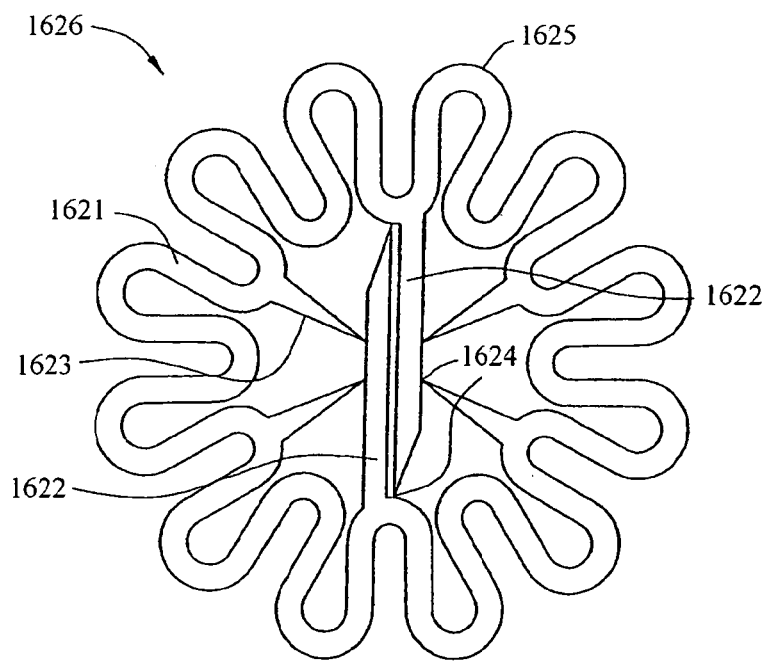

In the alternative embodiment of this invention illustrated in FIGS. 29A and 29B, the precursor 1620 is manufactured in an expanded oversize configuration to provide space for removing material from a sheet of material, such as a superelastic alloy, such as nickel-titanium, by conventional methods such as cutting, chemical etching, photochemical etching, stamping, electric discharge machining, laser cutting or the like.

The precursor 1620 is reconfigured by imposing radially inwardly directed force on body 1621 such that precursor 1620 takes a smaller planar shape such as one of those shown in FIG. 29B. The precursor 20 has a planar body 1621, tines 1622 and 1623 having points 1624 and such tines are connected by links 1625 as previously described with regard to FIG. 28A. The reconfigured precursor is then heat set and quenched as described above to complete the manufacture of clip 1626.

Figure 30A:
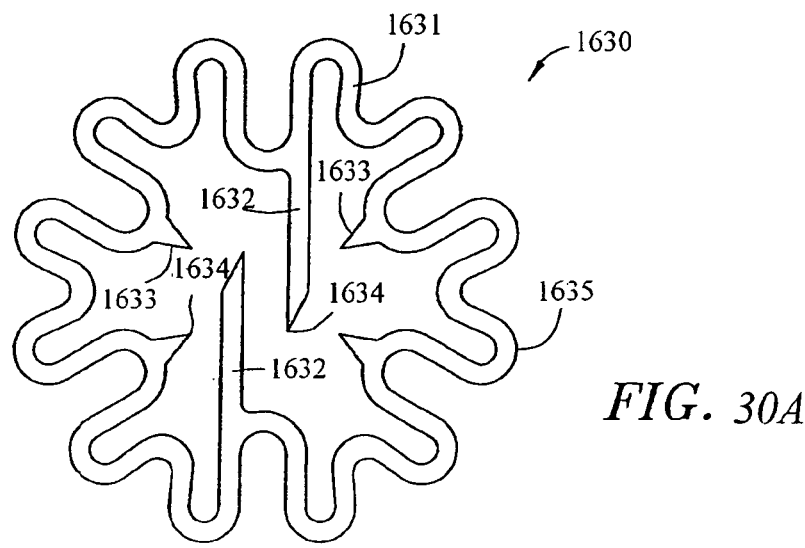
FIGS. 30A, 30b, and 30C illustrate alternate before and after-configurations of clips manufactured according to the method of this invention.
Figure 30B:
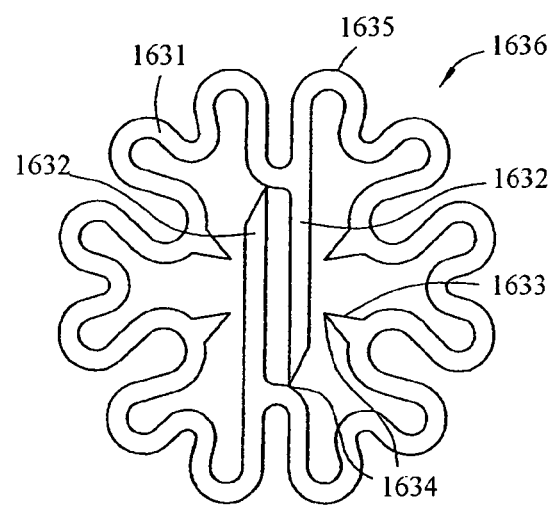
Figure 30C:
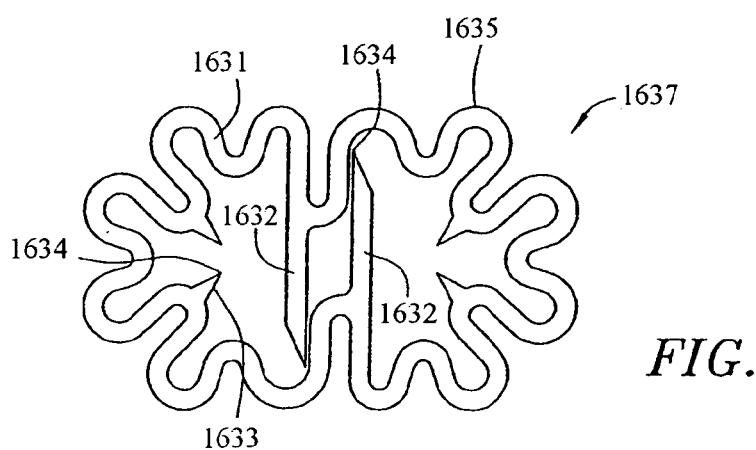

Clips of still other configurations can be manufactured in the manner of clip 1626 by starting with a differently shaped precursor such as precursor 1630 shown in FIG. 30A. Precursor 1630 can be reconfigured by being subjected to radially inward deforming forces as shown in FIG. 30B or by opposed laterally inward forces as shown in FIG. 30C. In each case, the planar body 1631 having tines 1632 and 1633 with points 1634 and links 1635 will be caused to take a smaller dimension and will be heat set as described above to form clips 1636 and 1637. Clips manufactured according to the method of the present invention can have a multitude of configurations other than those shown in FIGS. 28B, 29B, and 30C and 30D. For example, the configurations shown in U.S. patent application Ser. Nos. 09/732,178 and 10/081, 726, now U.S. Pat. Nos. 6,719,777 and 6,623,510, could be manufactured according to the present invention.

Figure 34:
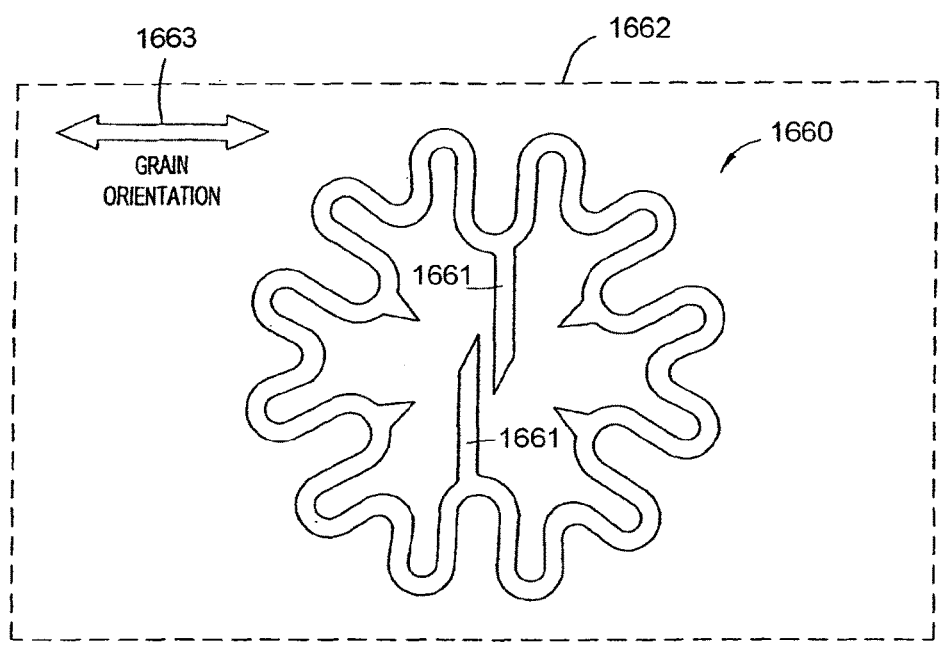
FIG. 34 illustrates one relationship between the grain orientation of a Nitinol sheet and the primary tines of a clip precursor.

It has been found that Nitinol sheet is stronger in one direction than in others, which may be the result of crystal orientation in the Nitinol. The clip precursors can be formed such that the primary tines are aligned with the strongest orientation of the Nitinol. It has been found, as shown in FIG. 7, that the greatest strength of the primary tines is achieved if those tines are transverse to the grain orientation of the Nitinol. Thus, FIG. 34 illustrates clip precursor 1660 having primary tines 1661 as the precursor would be cut from sheet 1662. The grain orientation of sheet 1662 is shown by the double-headed arrow 1663. Typically, a plurality of precursors 1660 would be cut from the same sheet, each with its primary tines transverse to the grain orientation of the sheet. In addition, even if clips are formed directly without using precursors, it is desirable that their primary tines be transverse to the grain orientation.

Figure 32:
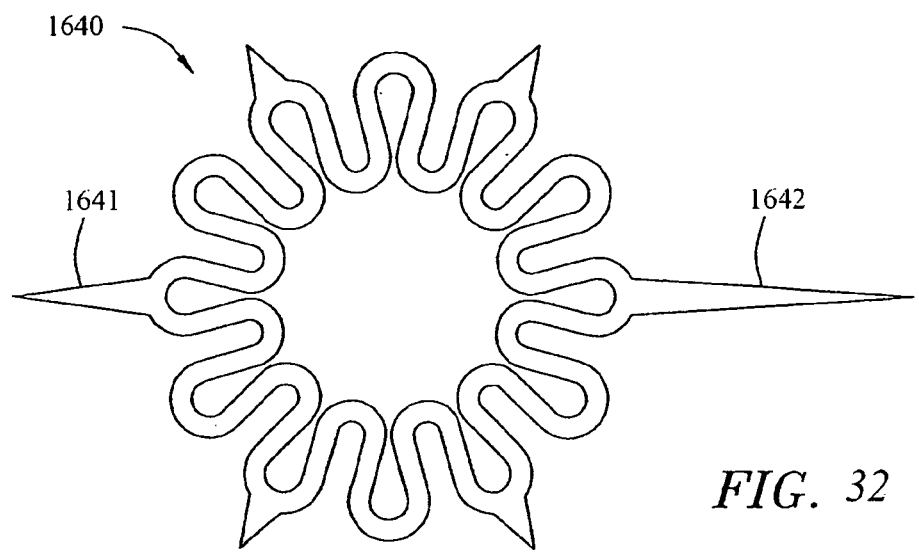
FIGS. 32 and 33 illustrate clip precursors in which radially opposed primary tines have different lengths.
Figure 33:
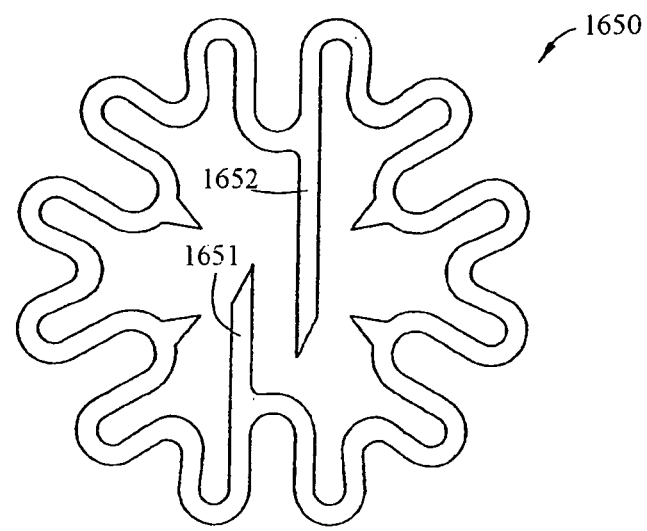

The clips of the present invention may have primary or secondary tines which have the same or different lengths and the tines may be straight or curved. For example, radially opposed tines may have one tine at "12 o'clock" which is longer than the opposing tine at "6 o'clock." Exemplary configurations of clip precursors with primary tines of different length are shown in FIGS. 32 and 33. In FIG. 32, clip precursor 1640 is shown with a primary tine 1641 which is shorter than primary tine 1642. Similarly, in FIG. 33, a clip precursor is shown which has a primary tine 1651 which is shorter than primary tine 1652.

The clips of the present invention may also be delivered using the apparatus and methods described in U.S. patent application Ser. No. 10/081,723, filed Feb. 21, 2002, now U.S. Pat. No. 6,942,674, which is assigned to the assignee of the present application, the disclosures of which, and any references therein, are incorporated herein in their entirety by this reference. Similarly, the apparatus and methods disclosed in U.S. patent application Ser. No. 10/081,717, filed Feb. 21, 2002, now U.S. Pat. No. 6,695,867, which is assigned to the Assignee of the present application, the disclosures of which, and any references therein, are incorporated herein in their entirety by this reference.

Other features can be added to the clips including radioopaque markers, and/or porous surfaces to promote tissue ingrowth or the clip may be coated in whole or in part with a bioabsorbable material and/or coated with a material containing a substance which is delivered to the patient for therapeutic, diagnostic or other purposes. Such coatings may comprise peptides, clotting factors or other materials designed to benefit the patient.

While the principal object of the present invention is to provide a manufacturing method which facilitates the production of clips having a small footprint, the present invention can also be used to make clips of larger dimensions since, no matter what methods are used to cut the precursor from a sheet of material, the ease of manufacture of even larger size clips is facilitated. Thus, the advantages of the present invention may be realized with regard to clips having larger sizes and clips having a variety of configurations.

Figure 35A:
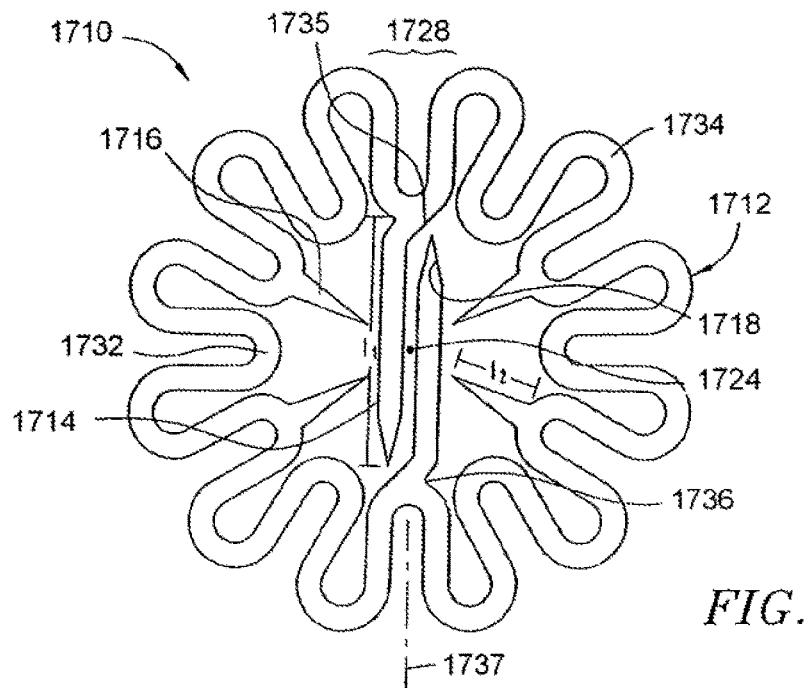
FIG. 35A illustrates a top view of a clip including a plurality of tines in a planar orientation, in which the primary tines are offset from the axis of symmetry of the loop from which they extend and are connected to a curved region of the loop by a straight connecting element in accordance with the present invention.
Figure 35B:
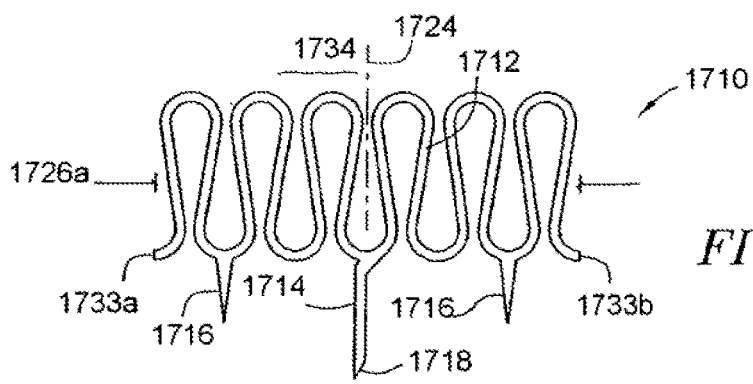
FIGS. 35B and 35C illustrate side views of the clip of FIG. 35A, with the tines oriented substantially transversely from the planar orientation, in compressed and expanded states, respectively.
Figure 35C:
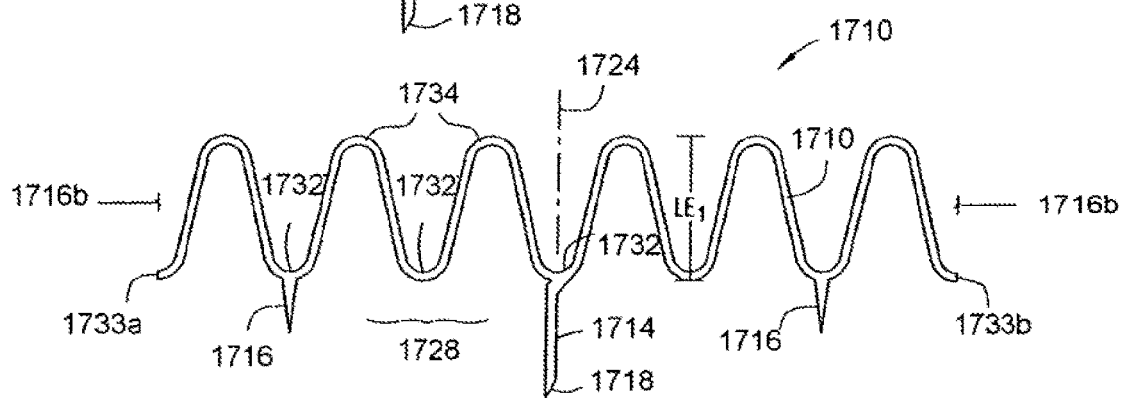

Turning now to the drawings, FIGS. 35A-35C show another embodiment of a closure device or clip 1710 for closing an incision, puncture, or other passage through tissue, e.g., communicating with a blood vessel or other body lumen (not shown). The clip 1710 includes a body 1712, which may be generally annular in shape and surrounds a central axis 1724, a plurality of primary tines 1714 and a plurality of secondary tines 1716 extending from the body 1712. As used herein, an "annular-shaped body" includes any hollow body, e.g., including one or more structures surrounding an opening, whether the body is substantially flat or has a significant thickness or depth. Thus, although an annular-shaped body may be circular, it may include other noncircular shapes as well, such as elliptical or other shapes that are asymmetrical about a central axis.

The body 1712 includes a plurality of looped or curved elements 1728 that are connected to one another to form the body 1712. Each looped element 1728 may include an inner or first curved region 1732 and an outer or second curved region 1734. In another embodiment, the first and second curved regions 1732, 1734 are out of phase with one another and are connected alternately to one another, thereby defining an endless sinusoidal pattern. Alternatively, other generally zigzag patterns may be provided that repeat periodically, e.g., saw tooth or square tooth patterns (not shown), instead of a sinusoidal pattern, thereby defining inner and outer regions that alternate about the body 1712.

The plurality of tines 1714 and 1716 may be biased to extend generally inwardly, e.g., towards one another and/or towards the central axis 1724. The tines 1714 and 1716 may be disposed on the first curved regions 1732, and oriented toward the central axis 1724 when the clip 1710 is in the planar configuration. The primary tines 14 are offset from the axis of symmetry 1737 of the loops from which they extend and are connected to a first curved region 1732 by a straight connecting element having a longer side 1735 and a shorter side 1736. In another embodiment, the tines 14 and 1716 may be provided in pairs opposite from one another or provided otherwise symmetrically with respect to the central axis 1724.

The tines 1714 and 1716 may include a variety of pointed tips, such as a bayonet tip, and/or may include barbs (not shown) for penetrating or otherwise engaging tissue. For example, to increase the penetration ability of the clip 1710 and/or to lower the insertion force required to penetrate tissue, each primary tine 1714, as shown in FIG. 35A as element 1718, and each secondary tine 1716 may include a tapered edge (not shown) extending towards the tip along one side of the tine 1714 or 1716. Alternatively, as shown in FIGS. 35A-35C, each tine 1714 or 16 may be provided with a tapered edge on each side of the tine 1714 or 1716 extending towards the tip.

Additionally, as shown in FIGS. 35A-35C, the tines 1714 and 1716 may be disposed on alternating first curved regions 1732. Thus, at least one period of a zigzag pattern may be disposed between adjacent tines 1714 and 1716, which may enhance flexibility of the clip 1710, as explained further below.

As shown in FIGS. 35B and 35C (where opposite ends 1733a, 1733b are connected to one another), the body 1712 and/or the tines 1714 and 1716 may be deflected such that the tines 1716 extend transversely with respect to the plane defined in the planar configuration, thereby defining a transverse configuration for the clip 1710. The tines 1714 and 1716 can be oriented substantially parallel to the central axis 1724 in the transverse configuration, as shown in FIG. 35B. In the transverse configuration, the body 1712 may have a generally annular shape defining a length, $LE_1$, that extends generally parallel to the central axis 1724, and corresponds generally to an amplitude of the zigzag pattern. The body 1712 can be sufficiently flexible such that the clip 1710 may assume a generally circular or elliptical shape (not shown), e.g., conforming to an exterior surface of a delivery device (not shown) used to deliver the clip 1710.

In another embodiment, the tines 1714 and 1716 and/or body 1712 are biased to move from the transverse configuration towards the planar configuration of FIG. 35A. Thus, with the tines 14 and 16 in the transverse configuration, the tines 1714 and 1716 may penetrate and/or be engaged with tissue at a puncture site. When the clip 1710 is released, the tines 1714 and 1716 may attempt to return towards one another as the clip 1710 moves towards the planar configuration, thereby drawing the engaged tissue together and substantially closing and/or sealing the puncture site, as explained further below.

The looped elements 1728 may distribute stresses in the clip 1710 as it is deformed between the planar and transverse configurations, thereby minimizing localized stresses that may otherwise plastically deform, break, or otherwise damage the clip 1710 during delivery. In addition, when the clip 1710 is in the transverse configuration, the looped elements 1728 may be movable between a compressed state, such as that shown in FIG. 35B, and an expanded state, such as that shown in FIG. 35C. The looped elements 1728 can be biased towards the expanded state, but may be compressed to the compressed state, e.g., by constraining the clip 1710. Alternatively, only a portion of the looped elements 1728 may be biased towards the expanded state, e.g., the first curved regions 1732, and/or the looped elements 1728 may be biased towards the compressed state. Furthermore, the looped elements 1728 reduce the force required to be exerted on the clip 1710 to transition the clip 1710 from the planar configuration to the transverse configuration before loading onto a delivery device (not shown).

With the clip 1710 in the transverse configuration, the looped elements 1728 may be circumferentially and/or radially compressed to the compressed state until the clip 1710 defines a first diameter or circumference 1726a, such as that shown in FIG. 35B. The clip 1710 may be constrained in the compressed state, e.g., by loading the clip 1710 onto a carrier assembly of a delivery device (not shown), as described further below. When released from the constraint, e.g., when deployed from the carrier assembly, the clip 1710 may automatically expand towards the expanded state, such as that shown in FIG. 35C, thereby defining a second diameter or circumference 1726b. Thus, the looped elements 1728 may facilitate reducing the profile of the clip 1710 during delivery, e.g., to facilitate introducing the clip 1710 through a smaller puncture or passage. Once the clip 1710 is deployed entirely from the delivery device, the looped elements 1728 may resiliently expand as the clip 1710 returns towards the planar configuration, as explained further below.

To manufacture the clip 1710 (or, similarly, any of the other clips described herein), the body 1712 and the tines 1714 and 1716 may be integrally formed from a single sheet of material, e.g., a superelastic alloy, such as Nitinol. Portions of the sheet may be removed using conventional methods, such as laser cutting, chemical etching, photo chemical etching, stamping, using an electrical discharge machine (EDM), and the like, or the method disclosed in U.S. patent application Ser. No. 10/335,075, filed Dec. 31, 2002, to form the clip. The tines 1714 and 1716 may be sharpened to a point, i.e., tips may be formed on the tines 1714 and 1716 using conventional methods, such as chemical etching, mechanical grinding, and the like.

The clip 1710 may be polished to a desired finish using conventional methods, such as electro-polishing, chemical etching, tumbling, sandblasting, sanding, and the like. Polishing may perform various functions depending on the method used to form the clip 1710. For a clip formed by laser cutting or using an EDM, polishing may remove heat affected zones (HAZ) and/or burrs from the clip. For a clip formed by photo chemical etching, polishing may create a smoother surface finish. For a clip formed by stamping, polishing may remove or reduce burrs from the bottom side of the clip, and/or may smooth the "roll" that may result on the topside of the clip from the stamping process.

In addition or alternatively, the clip 1710 may be formed from a shape memory alloy, e.g., Nitinol, with the looped elements 1728 formed initially in the compressed state and/or the clip 1710 in the planar configuration. With the clip 1710 deformed to the transverse configuration, the clip 1710 may be expanded, e.g., by applying a force radially outwards against an inner surface of the clip 1710, thereby expanding the looped elements 1728 to the expanded state. The looped elements 1728 may then be heat treated, e.g., by heating the clip 1710 to an austenitic state, to cause the looped elements 1728 to "remember" the expanded state, as is known to those skilled in the art. It may also be necessary to further heat treat the clip 1710 further, e.g., with the tines in the planar configuration to cause the body 1712 and/or tines 1714 and 1716 to "remember" and be biased towards the planar configuration, as is known to those skilled in the art. The clip 1710 may then be cooled, e.g., to a martensitic state, which may be at or close to ambient temperature, and manipulated, e.g., malleably deformed to the transverse configuration, for example, by loading the clip 1710 onto a delivery device (not shown), as described below. Thus, if the clip 1710 is subsequently heated to a predetermined temperature, e.g., at or below body temperature, the material may remember the planar configuration and/or expanded state and become biased towards them.

Each of the primary tines 1714 may have a length $l_1$, although alternatively, as shown in FIG. 35A, each of the primary tines 1714 may have a different length than one another. The primary tines 1714 may be disposed in one or more opposing pairs, e.g., on opposing first curved regions 1732, and may be oriented towards and/or across the central axis 1724 in the planar configuration. In the planar configuration, the lengths $l_1$ may be sufficiently long such that the primary tines 1714 at least partially overlap one another, i.e., extend across the central axis 1724 towards an opposing tine 1714. Therefore, the tips of the primary tines 1714 may extend past the central axis 1724 and/or the primary tines 14 in each pair may lie substantially parallel to each other when the clip 1710 is in the planar configuration.

Each of the secondary tines 16 may be disposed on a first or inner curved region 32, e.g., such that one or more secondary tines 16 may be provided between opposing pairs of primary tines 14. Each of the secondary tines 16 may have a length $l_2$ that is substantially less than the length $l_1$ of the primary tines 14.

A secondary tine 1716 can be disposed on either side of each primary tine 1714. For example, the clip 1710 shown in FIGS. 35A-35C has first and second primary tines 1714, and each of the first and second primary tines 1714 has a secondary tine 1716 on either side of it. Thus, the clip 1710 may have a total of two primary tines 1714 and four secondary tines 1716. Optionally, the secondary tines 1716 may be disposed substantially symmetrically about the central axis 1724. The tines 1714, 1716 may be provided on every other first curved regions 1732. For example, a first curved region 1732 having neither a primary tine 1714 nor a secondary tine 1716 may separate each adjacent tine, e.g., between two adjacent secondary tines 16, or between a secondary tine 16 and a primary tine 1714.

With the clip 1710 in the transverse configuration, the clip 1710 may be delivered such that the primary tines 1714 entirely penetrate the wall of a blood vessel or other body lumen, while the secondary tines 1716 only partially penetrate the wall due to their relative lengths, as explained further below.

As shown in FIG. 35A, primary tines 1714 are connected to curved regions 1732 by linear regions 1735 and 1736 which are of different lengths. Thus, primary tines 1714 are offset from the axis of symmetry 1737 of the loops having the curved regions to which they are attached. The offsetting of primary tines is also disclosed in parent application Ser. No. 10/335,075, filed Dec. 31, 2002, which discloses the use of curved configurations to connect the primary tines to the curved regions of the clip. It has been found desirable to use linear, or straight, regions, as shown as elements 1735 and 1736 in FIG. 35A to connect the primary tines 1714 of the present invention to the curved regions 1732.

Figure 36:
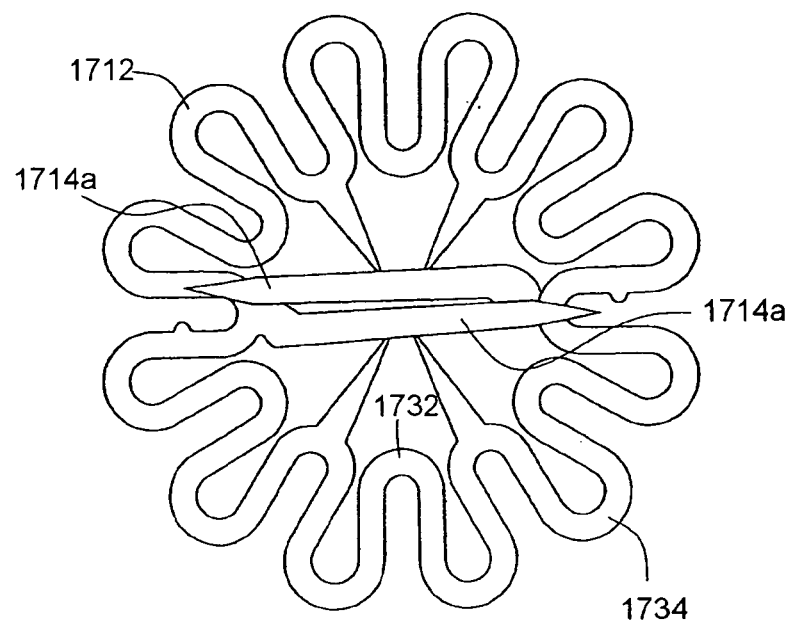
FIG. 36 illustrates a clip according to the present invention in which the primary tines overlap with the body of the clip.

FIG. 36 illustrates a clip of the same general type as that of FIG. 35A, but in a somewhat different embodiment in which primary tines 1714*a* overlap body 1712 at locations comprising first curved regions 1732.

Figure 37A:
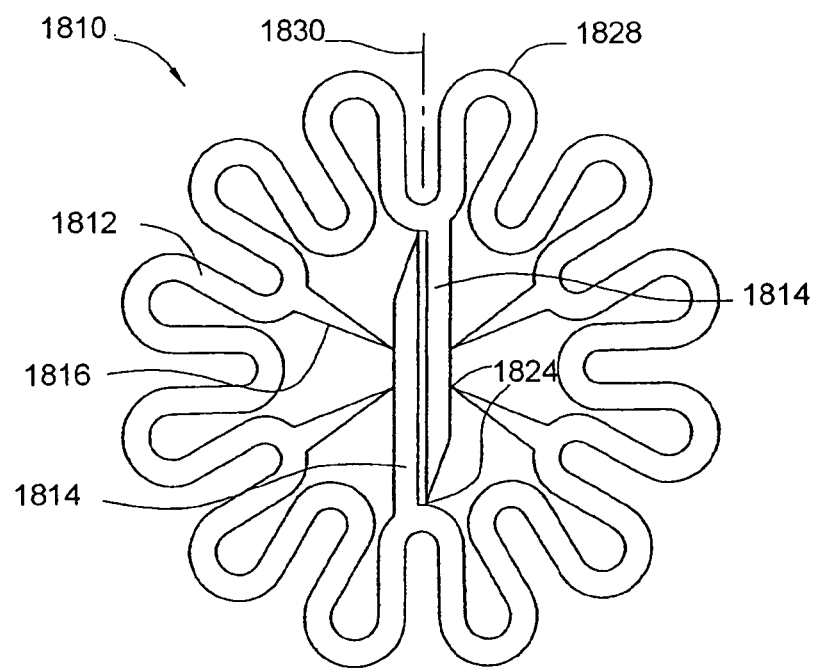
FIGS. 37A-37C illustrates top views of clips in which the primary tines are offset from the axis of symmetry of the loop from which they extend by a connecting element which is at least partially curved.
Figure 37B:
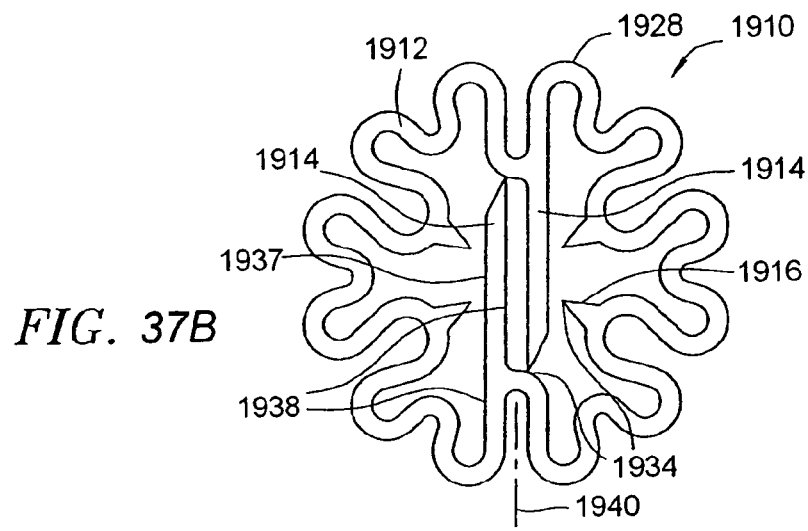
Figure 37C:
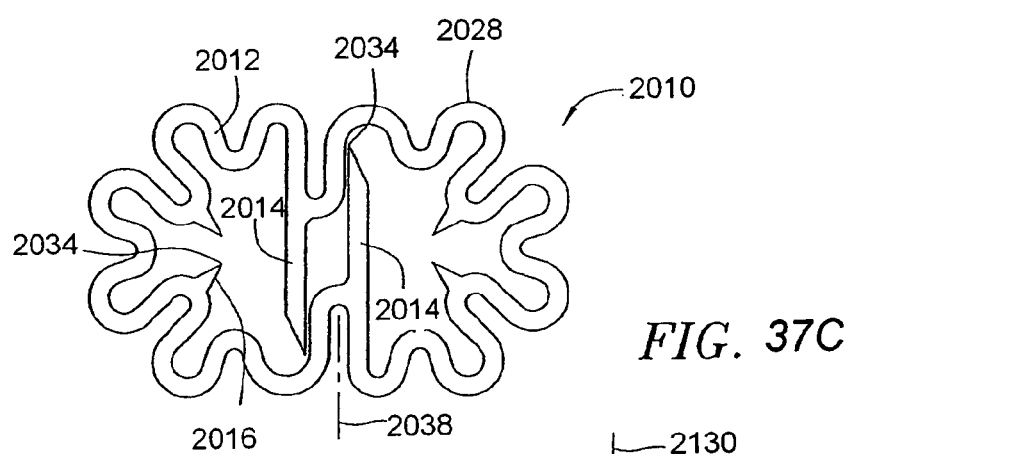

FIGS. 37A-37C illustrate various designs of clips configured according to the present invention in which the primary tines, which are offset from the axis of symmetry of the loop from which they extend, are connected directly to a first curved region or are connected to the curved region by extending one side of the curved region to form one side of the primary tine and connecting the other side of the primary tine with a curved connecting element.

Turning to FIGS. 37A-37C in more detail, FIG. 37A illustrates clip 1826 has body 1821, primary tines 1822, secondary tines 1823 and loops 1825. Each loop has an axis of symmetry such as that indicated by 1827. The tines are provided with point 1824. In this embodiment, the primary tines 1822 are offset from the axis of symmetry of the loop from which they extend and are connected directly to the first curved section of such loop.

In FIG. 37B, the clip 1936 has body 1931 having primary tines 1932 and secondary tines 1933 is illustrated. The body 1931 is provided with loops 1935 and the primary tines 1932 comprise a first side 1937 which is an extension of a side of the loop 1938 from which tine 1937 extends and another side 1939 which is connected directly to the loop from which it extends. The primary tines are offset from the axis of symmetry, indicated by 1940 of the loop from which they extend.

The clip of FIG. 37C is similar in some respects to the clip of 37B, but is generally elliptical in shape rather than generally circular in shape. Thus, clip 2037 comprises body 2031 which has loops 2035, primary tines 2032, secondary tines 2033 which tines have points 2034. In this embodiment, the primary tines 2032 extend beyond the innermost reach of the first curved regions which are opposite the first curved regions from which the primary tines extend. The primary tines are offset from the axis of symmetry 2038 of the loop from which they extend. The primary tines of the clip of FIG. 37C are connected to the loops from which they extend in the same manner as those of FIG. 37B.

Figure 38:
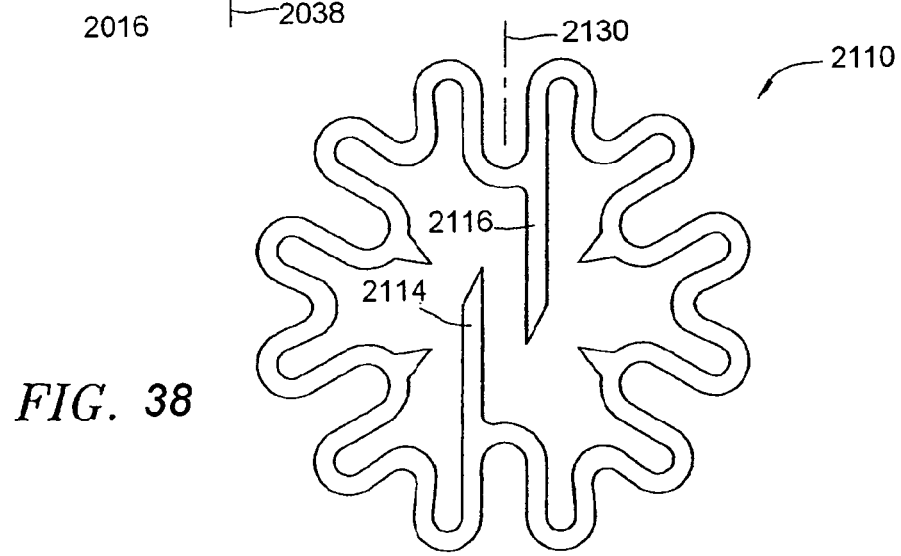
FIG. 38 illustrates a clip in which the primary tines have different lengths.

FIG. 38 illustrates a clip 2110 in which the primary tines 2114 and 2116 are of different lengths. The primary tines 2114 and 2116 are offset from the axis of symmetry 2130 of the loop from which they extend and are connected to the loop in the same manner as the primary tines of FIG. 37B.

Any of the clips of the present invention may include one or more radiopaque markers or other markers visible using external imaging, such as fluoroscopy. For example, using the clip 1710 of FIGS. 35A-35C as an example, the entire clip 1710 may be coated with radiopaque material, which may be a high density material such as gold, platinum, platinum/iridium, and the like.

Alternatively, the clip 1710 may be partially coated with radiopaque material by using masking techniques. For example, the entire clip 1710 may first be coated with radiopaque material. The clip 1710 may then be masked at locations where the radiopaque coating is desired. For example, the looped elements 1728 of the clip 1710 may be left unmasked during this process if it is desired to leave the looped elements 1728 uncoated by radiopaque material. This may be desirable, e.g., to prevent radiopaque material from adversely affecting the flexibility of the looped elements 1728. The clip 1710 may then be treated to remove the radiopaque material from the unmasked areas, in this example, the looped elements 1728. The masking may then be removed using conventional processes, leaving the rest of the clip 1710 coated with radiopaque material.

In another alternative, one or more discrete markers may be provided at predetermined locations on the clip 1710. For example, high density or radiopaque material may be crimped or otherwise secured onto opposing double looped or circular regions 1728. In another embodiment, a plurality of pockets may be provided on the looped elements 1728 into which high density plugs (not shown) may be bonded or otherwise secured. These various radiopaque markers may also be incorporated in any of the embodiments described herein.

Any of the clips of the present invention may be coated with a substance that enhances hemostasis and/or healing of a blood vessel, e.g., by increasing a rate of regeneration of endothelium on the interior surface of the vessel, or by decreasing inflammatory response at the treatment site. In one embodiment, a suitable synthetic peptide coating may be applied to a clip to attract endothelial cells to the surface. An exemplary synthetic peptide coating may, for example, attach to the same cell binding sites as collagen. In another embodiment, a clip may be coated with a combination of clotting factors in order to promote hemostasis. For example, one side of the clip may be coated with Factor III and an endopeptidase, such as PTA, to accelerate the intrinsic clotting pathway. On the opposite side of the clip, a combination of a protein cofactor proaccelerin (Factor V) and an activated endopeptidase, such as serum prothrombin conversion accelerator (SPCA), cothromboplastin, and the like, may be applied to accelerate the extrinsic clotting pathway. The clips of the present invention may also be coated with any suitable hydrophilic polymer that swells in the presence of bodily fluids in order to reduce, minimize, or stop blood flow, thereby aiding the hemostasis process.

As described herein, the clips of the present invention may be delivered using various apparatus and methods. Suitable apparatus that may be used to deliver a clip of the present invention are disclosed in U.S. application Ser. No. 10/081,723, filed on Feb. 21, 2002, now U.S. Pat. No. 6,942,674, and entitled "Apparatus and Methods for Delivering a Closure Device" and in U.S. application Ser. No. 10/356,214, filed Jan. 30, 2003, and Ser. No. 10/638,115, filed Aug. 8, 2003, and Ser. No. 10/081,725, filed Feb. 2, 2001, now U.S. Pat. No. 6,749,621, which are assigned to the assignee of the present application, the disclosures of which, and any references therein, are incorporated herein in their entirety by this reference.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims. For example, and not by way of limitation, the features and structures of one clip can be used with any other clip described herein. Similarly, the structures and methods useable to deploy a clip can be used to deploy other clips, including, but not limited to, those clips described herein.

What is claimed is:

1. A method comprising:
   locating an opening in tissue by advancing a member through the opening in tissue; and
   following locating the opening, deploying a medical device to aid with sealing the opening, including releasing engagement between the member and the medical device so that a portion of the medical device engages tissue and closes the opening, the medical device comprising:
   a plurality of strut members generally biased to a deployed configuration to form a plurality of generally diamond-shaped openings in an annular shaped structure with the generally diamond-shaped openings extending generally longitudinally relative to a longitudinal axis of medical device; and
   a plurality of tissue engaging portions, each tissue engaging portion being disposed between adjacently positioned generally diamond-shaped openings.

2. The method of claim 1, wherein deploying the medical device further comprises releasing the medical device from the member.

3. The method of claim 1, wherein deploying the medical device comprises proximally moving the member to allow the medical device to expand.

4. The method of claim 1, wherein deploying the medical device further comprises advancing the medical device along the member until the medical device disengages from the member.

5. The method of claim 1, further comprising removing the member from the opening in tissue.

6. The method of claim 1, wherein deploying the medical device further comprises advancing the medical device to move the plurality of tissue engaging portions with the plurality of struts, the plurality of struts forming a plurality of spring elements.

7. The method of claim 1, wherein the plurality of struts are biased to position the plurality of tissue engaging portions for tissue engagement.

8. The method of claim 1, wherein locating the tissue further comprises positioning a locator through the opening in tissue.

9. A method comprising:
   locating an opening in tissue by advancing a member through the opening in tissue; and
   following locating the opening, deploying a medical device to penetrate tissue, including releasing engagement between the member and the medical device so that a portion of the medical device engages tissue and closes the opening, the medical device comprising:
   a plurality of generally diamond-shaped openings formed from a plurality of looped elements generally biased to a deployed configuration to, the plurality of looped elements being configured to position the plurality of generally diamond-shaped openings in an annular arrangement; and
   a plurality of tissue engaging portions, each tissue engaging portion being disposed between adjacently positioned generally diamond-shaped openings and extending from a junction of adjacent looped elements of the plurality of looped elements at a location spaced apart from an apex of the generally diamond-shaped openings.

10. The method of claim 9, further comprising monitoring a position of the medical device.

11. The method of claim 10, wherein monitoring the position of the medical device comprising monitoring one or more radiopaque markers using fluoroscopy.

12. The method of claim 11, further comprising monitoring a relative position of the medical device to a distal tip of a locator locating the opening in tissue.

13. The method of claim 9, wherein deploying the medical device further comprises releasing the medical device from the member.

14. The method of claim 9, wherein deploying the medical device further comprises advancing the medical device along the member until the medical device disengages from the member.

15. The method of claim 9, further comprising removing the member from the opening in tissue.

16. The method of claim 9, the medical device further comprising a plurality of strut members, wherein deploying the medical device further comprises advancing the medical device to move the plurality of tissue engaging portions with the plurality of struts, the plurality of struts forming a plurality of spring elements.

17. The method of claim 9, the medical device further comprising a plurality of strut members, wherein the plurality of struts are biased to position the plurality of tissue engaging portions for tissue engagement.

18. The method of claim 9, wherein locating the tissue further comprises positioning a locator through the opening in tissue.

* * * * *